US010874726B2

(12) United States Patent
Darrah et al.

(10) Patent No.: US 10,874,726 B2
(45) Date of Patent: Dec. 29, 2020

(54) AUTOIMMUNE ANTIGENS AND CANCER

(71) Applicant: The Johns Hopkins University, Baltimore, MD (US)

(72) Inventors: Erika Darrah, Baltimore, MD (US); Ami A. Shah, Ellicot City, MD (US); Livia A. Casciola-Rosen, Pikesville, MD (US); Antony Rosen, Pikesville, MD (US); Christine Joseph, Baltimore, MD (US); Bert Vogelstein, Baltimore, MD (US); Kenneth W. Kinzler, Baltimore, MD (US); Nickolas Papadopoulos, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 191 days.

(21) Appl. No.: 15/101,174

(22) PCT Filed: Dec. 4, 2014

(86) PCT No.: PCT/US2014/068635
§ 371 (c)(1),
(2) Date: Jun. 2, 2016

(87) PCT Pub. No.: WO2015/085099
PCT Pub. Date: Jun. 11, 2015

(65) Prior Publication Data
US 2016/0303209 A1 Oct. 20, 2016

Related U.S. Application Data

(60) Provisional application No. 61/911,626, filed on Dec. 4, 2013.

(51) Int. Cl.
*A61K 39/00* (2006.01)
*A61K 38/00* (2006.01)

(52) U.S. Cl.
CPC .......... *A61K 39/0008* (2013.01); *A61K 38/00* (2013.01); *A61K 2039/585* (2013.01)

(58) Field of Classification Search
CPC .................. A61K 2039/585; A61K 39/0008
See application file for complete search history.

(56) References Cited

FOREIGN PATENT DOCUMENTS

WO 2012-061481 A2 5/2012

OTHER PUBLICATIONS

Burrows et al (Trends in Immunology, 2006, vol. 27, pp. 11-16) (Year: 2006).*
Purcell et al (Nature Reviews Drug Discovery, 2007, vol. 6, pp. 404-414) (Year: 2007).*
Hacohen et al, Cancer Immunology Research, 2013, vol. 1, pp. 11-15 (Year: 2013).*
A. Gabrielli, et al., Scleroderma. The New England journal of medicine 360, 1989 (2009).
M. L. Harris, A. Rosen, Autoimmunity in scleroderma: the origin, pathogenetic role, and clinical significance of autoantibodies. Current opinion in rheumatology 15, 778 (2003).
A. A. Shah, A. Rosen et al., Close temporal relationship between onset of cancer and scleroderma in patients with RNA polymerase I/III antibodies. Arthritis and rheumatism 62, 2787 (2010).
A. A. Shah, A. Rosen, Cancer and systemic sclerosis: novel insights into pathogenesis and clinical implications. Current opinion in rheumatology 23, 530 (2011).
A. G. Knudson, Hereditary cancer: two hits revisited. Journal of cancer research and clinical oncology 122, 135 (1996).
Y. Kim, et al., Immune epitope database analysis resource. Nucleic acids research 40, W525 (2012).
P. Wang et al., A systematic assessment of MHC class II peptide binding predictions and evaluation of a consensus approach. PLoS computational biology 4, e1000048 (2008).
P. Wang et al., Peptide binding predictions for HLA DR, DP and DQ molecules. B}.fC bioinformatics 11, 568 (2010).
Z. C. Ding et al., Cytotoxic chemotherapy and CD4+ effector T cells: an emerging alliance for durable antitumor effects. Clinical & developmental immunology 2012, 890178 (2012).
I. Mellman et al., Cancer immunotherapy comes of age. Nature 480, 480 (2011).
P. K. Chattopadhyay et al., A live-cell assay to detect antigen-specific CD4−;−T cells with diverse cytokine profiles. Nature medicine 11, 1113 (2005).
M. Frentsch, et al., Direct access to CD4+ T cells specific for defined antigens according to CD154 expression. Nature medicine 11, 1118 (2005).
G. T. Nepom et al., HLA class II tetramers: tools for direct analysis of antigen-specific CD4+ T cells. Arthritis and rheumatism 46, 5 (2002).
K. J. Jackson et al., The Shape of the Lymphocyte Receptor Repertoire: Lessons from the B Cell Receptor. Frontiers in immunology 4, 263 (2013).
M. G. McHeyzer-Williams et al., Antigen-specific development of primary and memory T cells in vivo. Science 268, 106 (1995).
R. Buchbinder et al., Incidence of malignant disease in biopsy-proven inflammatory myopathy. A population-based cohort study. Annals of internal medicine 134, 1087 (2001).
S. A. Forbes et al., COSMIC: mining complete cancer genomes in the Catalogue of Somatic Mutations in Cancer. Nucleic acids research 39, D945 (2011).
H. A. Doyle, M. J. Mamula, Posttranslational modifications of self-antigens Annals of the New York Academy of Sciences 1050, 1 (2005).

(Continued)

*Primary Examiner* — Karen A. Canella
(74) *Attorney, Agent, or Firm* — Fish & Richardson P.C.

(57) ABSTRACT

Autoimmune diseases are thought to be initiated by exposures to foreign antigens that cross-react with endogenous molecules. Analyses of peripheral blood lymphocytes and serum suggested that mutations in autoimmune antigen targets sparked cellular immunity and cross-reactive humoral immune responses. Acquired immunity to autoimmune antigens can help control naturally occurring cancers.

15 Claims, 22 Drawing Sheets
Specification includes a Sequence Listing.

(56) References Cited

OTHER PUBLICATIONS

M. J. Mamula et al., Isoaspartyl post-translational modification triggers autoimmune responses to selfproteins. The Journal of biological chemistry 274, 22321 (1999).
R.H. Lin et al., Induction of autoreactive B cells allows priming of autoreactive T cells. The Journal of experimental medicine 173, 1433 (1991).
M. J. Mamula et al., B cells process and present lupus autoantigens that initiate autoimmune T cell responses. Journal of immunology 152, 1453 (1994).
M. L. Albert, R. B. Darnell, Paraneoplastic neurological degenerations: keys to tumour immunity. Nature reviews. Cancer 4, 36 (2004).
C. Gaudin, F. Kremer, E. Angevin, V. Scott, F. Triebel, A hsp70-2 mutation recognized by CTL on a human renal cell carcinoma. Journal of immunology 162, 1730 (1999).
R. F. Wang, X. Wang, A. C. Atwood, S. L. Topalian, S. A. Rosenberg, Cloning genes encoding MHC class II-restricted antigens: mutated CDC27 as a tumor antigen. Science 284, 1351 (1999).
T. Wolfel, M. Hauer, J. Schneider, M. Serrano, C. Wolfel, E. Klehmann-Hieb, E. De Plaen, T. Haill::eln, K. H. Meyer zum Buschenfelde, D. Beach, A pl6INK4ainsensitive CDK4 mutant targeted by cytolytic T lymphocytes in a human melanoma. Science 269, 1281 (1995).
M. E. Engelhorm, J. A. Guevara-Patino, G. Noffz, A. T. Hooper, 0. Lou, J. S. Gold, B. J. Kappel, A. N. Houghton, Autoimmunity and tumor immunity induced by immune responses to mutations in self. Nature medicine 12, 198 (2006).
L. Casciola-Rosen, K. Nagaraju, P. Plotz, K. Wang, S. Levine, E. Gabrielson, A. Corse, A. Rosen, Enhanced autoantigen expression in regenerating muscle cells in idiopathic inflammatory myopathy. The Journal of experimental medicine 201, 591 (2005).
R. D. Schreiber, L. J. Old, M. J. Smyth, Cancer immunoediting: integrating immunity's roles in cancer suppression and promotion. Science 331, 1565 (2011).
S. Bernatsky, J. F. Boivin, L. Joseph, R. Rajan, A. Zoma, S. Manzi, E. Ginzler, M. Urowitz, D. Gladman, P.R. Fortin, M. Petri, S. Edworthy, S. Barr, C. Gordon, S. C. Bae, J. Sibley, D. Isenberg, A. Rahman, C. Aranow, M.A. Dooley, K. Steinsson, 0. Nived, G. Sturfelt, G. Alarcon, J. L. Senecal, M. Zummer, J. Hanly, S. Ensworth, J. Pope, H. El-Gabalawy, T. McCarthy, Y. St Pierre, R. Ramsey-Goldman, A. Clarke, An international cohort study of cancer in systemic lupus erythematosus. Arthritis and rheumatism 52, 1481 (2005).
E. Tatsis, E. Reinhold-Keller, K. Steindorf, A. C. Feller, W. L. Gross, Wegener's granulomatosis associated with renal cell carcinoma. Arthritis and rheumatism 42, 751 (1999).
B. Vogelstein, N. Papadopoulos, V. E. Velculescu, S. Zhou, L.A. Diaz, K. W. Kinzler, Cancer Genome Landscapes. Science 339, 1546 (2013).
M. Burnet, Cancer—A Biological Approach. BMJ 1, 841 (1957).
S. A. Quezada, K. S. Peggs, Exploiting CTLA-4, PD-1 and PD-LI to reactivate the host immune response against cancer. British journal of cancer 108, 1560 (2013).
M. DuPage, C. Mazumdar, L. M. Schmidt, A. F. Cheung, T. Jacks, Expression of tumour-specific antigens underlies cancer immunoediting. Nature 482, 405 (2012).
H. Matsushita, M. D. Vesely, D. C. Koboldt, C. G. Rickert, R. Uppaluri, V. J. Magrini, C. D. Arthur, J.M. White, Y. S. Chen, L. K. Shea, J. Hundal, M. C. Wendl, R. Demeter, T. Wylie, J.P. Allison, M. J. Smyth, L. J. Old, E. R. Mardis, R. D. Schreiber, Cancer exome analysis reveals a T-cell-dependent mechanism of cancer immunoediting. Nature 482, 400 (2012).
Preliminary criteria for the classification of systemic sclerosis (scleroderma). Subcommittee for scleroderma criteria of the American Rheumatism Association Diagnostic and Therapeutic C1iteria Committee Arthritis and rheumatism 23, 581 (1980).
P. J. Clements, P.A. Lachenbruch, J. R. Seibold, B. Zee, V. D. Steen, P. Brennan, A. J. Silman, N. Allegar, J. Varga, M. Massa, et al., Skin thickness score in systemic sclerosis: an assessment of interobserver variability in 3 independent studies. The Journal of rheumatology 20, 1892 (1993).
E. C. LeRoy, C. Black, R. Fleischmajer, S. Jablonska, T. Krieg, T. A. Medsger, Jr., N. Rowell, F. Wollheim, Scleroderma (systemic sclerosis): classification, subsets and pathogenesis. The Journal ofrheumatology 15, 202 (1988).
J. Wu, H. Matthaei, A. Maitra, M. Dal Molin, L. D. Wood, J. R. Eshleman, M. Goggins, M. I. Canto, R. D. Schulick, B. H. Edil, C. L. Wolfgang, A. P. Klein, L.A. Diaz, P. J. Allen, C. M. Schmidt, K. W. Kinzler, N. Papadopoulos, R.H. Hruban, B. Vogelstein, Recurrent GNAS Mutations Define an Unexpected Pathway for Pancreatic Cyst Development. Science Translational Medicine 3, 92ra66 (2011).
D.S. Herman, G. K. Hovingh, 0. Iartchouk, H. L. Rehm, R. Kucherlapati, J. G. Seidman, C. E. Seidman, Filter-based hybridization capture of subgenomes enables resequencing and copy-number detection. Nat. ~Methods 6, 507 (2009).
I. Kinde, J. Wu, N. Papadopoulos, K. W. Kinzler, B. Vogelstein, Detection and quantification of rare mutations with massively parallel sequencing. Proceedings of the National Academy of Sciences of the United States of Anierica 108, 9530 (2011).
L.A. Casciola-Rosen, A. F. Pluta, P.H. Plotz, A. E. Cox, S. Morris, F. M. Wigley, M. Petri, A. C. Gelber, A. Rosen, The DNA mismatch repair enzyme PMS 1 is a myositisspecific autoantigen. Arthritis and rheumatism 44, 389 (2001).
Hu et al., "Characterization of Human RNA Polymerase III Indentifies" vol. 22 No. 22. pp. 8044-8055 (2002).
International Search Report for PCT/US2014/068635, dated Mar. 5, 2015.
Ng et al., 'Increased noncanonical splicing of autoantigen transcripts provides the structural basis for expression of untolerized epitopes', Journal of Allergy and Clinical Immunology, vol. 114, No. 6, pp. 1463-1470 (2004).
Caspi, 'Immunotherapy of autoimmunity and cancer: the penalty for success', Nature Reviews Immunology, vol. 8, No. 12, pp. 970-976 (internal pp. 1-16) (2008).
Pardoll, 'Inducing autoimmune disease to treat cancer', PNAS, vol. 96, No. 10, pp. 5340-5342 (1999).
Saitoh et al., 'CENP-C, an autoantigen in scleroderma, is a component of the human inner kinetochore plate', Cell, vol. 70, No. 1, pp. 115-125 (1992).
Jackson et al., "The Central Role Played by Peptides in the Immune Response and the Design of Peptide-Based Vaccines Against Infectious Diseases and Cancer," Current Drug Targets, 2002, 3:175-196.
Lipman et al., "Monoclonal Versus Polyclonal Antibodies: Distinguishing Characteristics, Applications, and Information Resources," ILAR Journal, 2005, 46(3):258-268.
Purcell et al., "Dissecting the Role of Peptides in the Immune Response: Theory, Practice and the Application to Vaccine Design," Journal of Peptide Science, 2003, 9:255-281.

\* cited by examiner

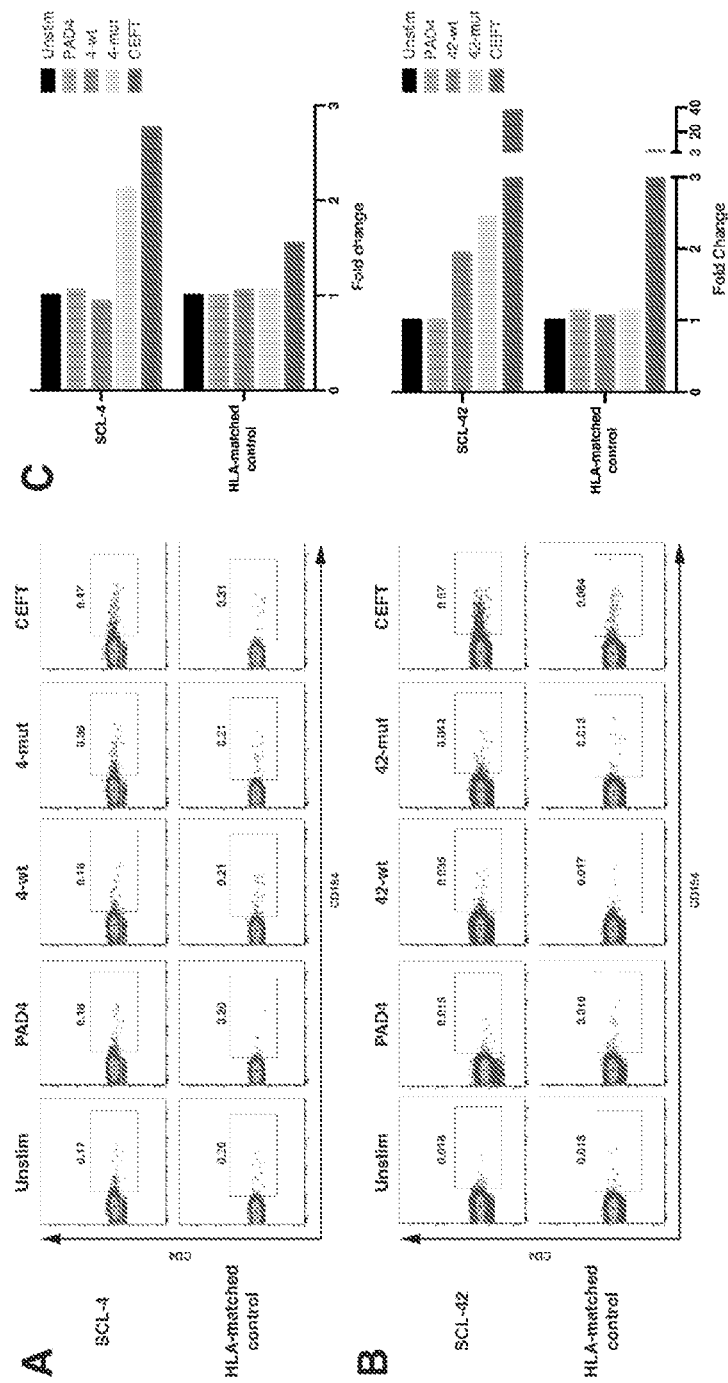
Fig. 1A-C

Table 1 - Selected clinical and genetic characteristics of the scleroderma patients evaluated in this study

| Patient # | Scleroderma duration at diagnosis of cancer (yrs) | Auto-antibodies to: | Age at diagnosis of cancer | Cancer Type | Cancer Subtype | Cancer Stage | POLR3A mutation - % mutant alleles | POLR3A Mutation - genomic position on chr 10 | POLR3A Mutation - amino acid change | POLR3A Loss of heterozygosity (LOH) |
|---|---|---|---|---|---|---|---|---|---|---|
| SCL-1 | -0.2 | RPC1 | 51 | Breast cancer | Invasive ductal | Stage 1A | No mutation detected | NA | NA | LOH |
| SCL-2 | -0.1 | RPC1 | 42.3 | Lung cancer | Small cell carcinoma | Stage 1 or II* | 26% | 79414962C>G | p.E1072Q | LOH |
| SCL-4 | -0.4 | RPC1 | 44 | Ovarian cancer | Adenocarcinoma | Stage IIIC | 4.3% | 79407320C>G | p.K1365N | No LOH |
| SCL-13 | 0.3 | RPC1 | 51.1 | Breast Cancer | Invasive ductal | Stage IIB | No mutation detected | NA | NA | LOH |
| SCL-35 | -2 | RPC1 | 50.9 | Breast cancer | Ductal carcinoma in-situ | Stage 0 | No mutation detected | NA | NA | No LOH |
| SCL-42 | 1.5 | RPC1 | 47.5 | Breast cancer | Invasive ductal | Stage IIA | (31%) | 79455393A>G | p.I104T | LOH |
| SCL-81 | -4.2 | RPC1 | 54.6 | Colorectal cancer | Adenocarcinoma | Stage III | No mutation detected | NA | NA | LOH |
| SCL-82 | 2.5 | RPC1 | 51.1 | Breast cancer | Ductal carcinoma in-situ | Stage 0 | No mutation detected | NA | NA | No LOH |
| SCL-5 | 9.2 | TOP1 | 74.6 | Lung cancer | Adenocarcinoma | Stage IB | No mutation detected | NA | NA | No LOH |
| SCL-8 | 0.4 | TOP1 | 65.1 | Breast cancer | Infiltrating lobular | Stage IIIA | No mutation detected | NA | NA | No LOH |
| SCL-11 | 13.4 | TOP1 | 55.7 | Breast cancer | Infiltrating lobular | Stage IIIC | No mutation detected | NA | NA | No LOH |
| SCL-12 | 34 | CENPB | 68.6 | Anal cancer | Squamous cell carcinoma | Stage 1 | No mutation detected | NA | NA | Uninformative** |
| SCL-19 | 34 | TOP1 | 74.1 | Breast cancer | Ductal carcinoma in-situ | Stage 0 | No mutation detected | NA | NA | No LOH |
| SCL-24 | 36.9 | CENPB | 64.2 | B cell lymphoma | Extranodal, Mantle cell | Stage IV | No mutation detected | NA | NA | No LOH |
| SCL-32 | -2.5 | CENPB | 43.1 | Breast cancer | Invasive ductal | Stage 1 | No mutation detected | NA | NA | Uninformative** |
| SCL-85 | 15 | TOP1 | 52.1 | Breast Cancer | Invasive ductal | Stage IIA | No mutation detected | NA | NA | No LOH |

* Patient records indicate only that the disease was localized
** Uninformative indicates that none of the evaluated SNPs were heterozygous in the normal cells of the patient.
NA - Not applicable

Fig. 3

Table 2. Allelic ratios of SNP loci within and closely surrounding the *POLR3A* gene.

| Chr 10 position | SNP ID | Patients with RPC-1 antibodies | | | | | | | | | Patients without RPC-1 antibodies | | | | | | | |
|---|---|---|---|---|---|---|---|---|---|---|---|---|---|---|---|---|---|---|
| | | SCL-1 | SCL-2 | SCL-4 | SCL-13 | SCL-35 | SCL-42 | SCL-81 | SCL-82 | SCL-5 | SCL-8 | SCL-11 | SCL-12 | SCL-19 | SCL-24 | SCL-32 | SCL-85 |
| 79,213,314 | rs1054608 | | | 102% | NI | NI | | | NI | NI | NI | 99% | NI | 99% | 103% | NI | NI |
| 79,222,098 | rs2165046 | | | 99% | NI | NI | | | NI | NI | NI | 99% | NI | 94% | 102% | NI | NI |
| 79,222,113 | rs1058203 | NI | NI | NI | NI | 100% | NI | | NI | NI | 102% | NI | NI | NI | 99% | NI | 99% |
| 79,222,157 | rs1058202 | | NI | 102% | NI | NI | NI | | NI | NI | 102% | NI | NI | NI | NI | NI | 97% |
| 79,230,809 | rs10762763 | | | 103% | NI | NI | | | NI | NI | NI | 102% | NI | 102% | 104% | NI | NI |
| 79,235,661 | rs2289311 | | | 103% | NI | NI | | | NI | 97% | NI | 104% | NI | 100% | 103% | NI | NI |
| 79,260,691 | rs10824579 | NI | | 97% | NI | NI | | | NI | NI | NI | 96% | NI | 97% | 103% | NI | NI |
| 79,323,400 | rs1248888 | | NI | NI | NI | 102% | NI | | NI | 101% | 102% | NI | NI | NI | 101% | NI | 96% |
| 79,406,970 | rs2241547 | | NI | NI | NI | 104% | NI | NI | NI | NI | NI | NI | NI | NI | NI | NI | 102% |
| 79,415,741 | rs12241228 | NI | NI | NI | | NI | NI | | NI | 100% | NI | NI | NI | NI | NI | NI | NI |
| 79,415,795 | rs3815891 | | NI | NI | | NI | NI | 95% | NI | 103% | NI | NI | NI | NI | NI | NI | 102% |
| 79,419,810 | rs7094028 | | NI | NI | | NI | NI | 95% | NI | 98% | 96% | NI | NI | NI | NI | NI | 104% |
| 79,424,105 | rs2818827 | | NI | 104% | NI | 100% | NI | | NI | NI | 102% | NI | NI | NI | NI | NI | 102% |
| 79,424,140 | rs12267816 | NI | NI | NI | NI | NI | NI | | NI | 104% | NI | NI | NI | NI | NI | NI | NI |
| 79,442,860 | rs2493568 | | NI | 96% | | 101% | NI | | NI | NI | 103% | NI | NI | NI | NI | NI | 101% |
| 79,514,037 | rs67287610 | NI | NI | NI | NI | 100% | NI | | NI | 99% | NI | NI | NI | NI | NI | NI | NI |
| 79,514,072 | rs4979801 | | NI | NI | | 101% | NI | | NI | NI | 99% | NI | NI | 104% | NI | NI | NI |
| 79,546,360 | rs2253909 | | NI | 94% | | 102% | NI | | NI | 102% | 100% | NI | NI | 98% | NI | NI | 104% |
| 79,549,686 | rs2253513 | | NI | 102% | | 102% | NI | | NI | NI | 104% | NI | NI | NI | NI | NI | |
| 79,573,735 | rs2114907 | | NI | 103% | | 104% | NI | | 96% | NI | 100% | 100% | NI | NI | NI | NI | NI |
| 79,615,946 | rs1249134 | | NI | 98% | | 102% | NI | | NI | NI | 104% | 99% | NI | 104% | NI | NI | NI |
| 79,618,728 | rs1249126 | | NI | 103% | | 101% | NI | | NI | NI | NI | NI | NI | 98% | NI | NI | NI |
| 79,654,802 | rs2434123 | NI | NI | NI | NI | NI | | NI | 102% | NI | 104% | NI | NI | NI | NI | NI | NI |
| Allelic ratio average* | | 77% | 88% | 99% | 44% | 101% | | 88% | 99% | 99% | 101% | 100% | NI | 99% | 102% | NI | 100% |
| Allelic ratio S.D. (%) | | 13% | 4% | 6% | 2% | 4% | 3% | 7% | 4% | 5% | 3% | 2% | NI | 3% | 2% | NI | 4% |

*Entries represent the allelic ratios of the indicated SNPs. The values in normal individuals were 100% +/- 3.10%. Allelic ratios less than 2 standard deviations (SD) from the mean (i.e., <94%) are highlighted in red. A tumor was considered to exhibit LOH if more than 3/4 of the informative SNPs exhibited allelic ratios <94%. NI: Non-informative, i.e., the SNP was not heterozygous in the normal cells of the patient (see Supplemental material, Materials and Methods).

Table 3. Dominant TCR sequences identified by massively parallel sequencing after stimulation with wt or mutant peptides

| Vβ | | CDR3 | | Jβ | CDR3 length | Total # sequences | # unique (a.a.) sequences | SEQ ID NOS. |
|---|---|---|---|---|---|---|---|---|
| SCL-42 wt-stimulated TCRs | | | | | | | | |
| Vβ7 | LCASS | PNELGQGSAF | FGQGT | Jβ1.1 | 10* | 160 | 1 | SEQ ID NO. 97 |
| Vβ12 | FCASS | DEVNTEAF | FGQGT | Jβ1.1 | 8* | 18 | 1 | SEQ ID NO. 98 |
| Vβ24 | LCATS | TGTVMNTEAF | FGQGT | Jβ1.1 | 10 | 1332 | 6 | SEQ ID NO. 99 |
| SCL-42 mutant-stimulated TCRs | | | | | | | | |
| Vβ7 | LCASS | ESWTDYGYT | FGSGT | Jβ1.2 | 9* | 97 | 1 | SEQ ID NO. 100 |
| Vβ12 | FCASS | DGGTRHEQF | FGPGT | Jβ2.1 | 9* | 160 | 2 | SEQ ID NO. 101 |
| Vβ24 | LCATS | RDTVNQPQH | FGDGT | Jβ1.5 | 9* | 2066 | 17 | SEQ ID NO. 102 | a.a. = amino acids
* Corresponds to the expected length based on TCR spectratyping

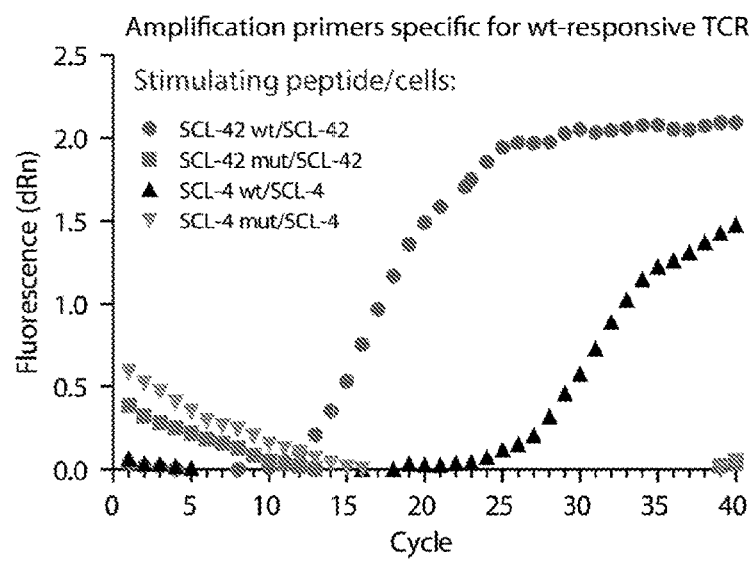
Fig. 9A
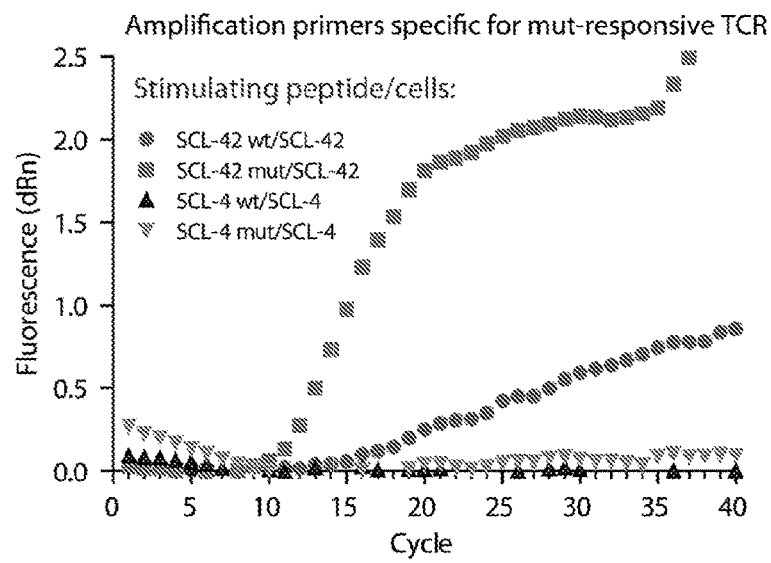
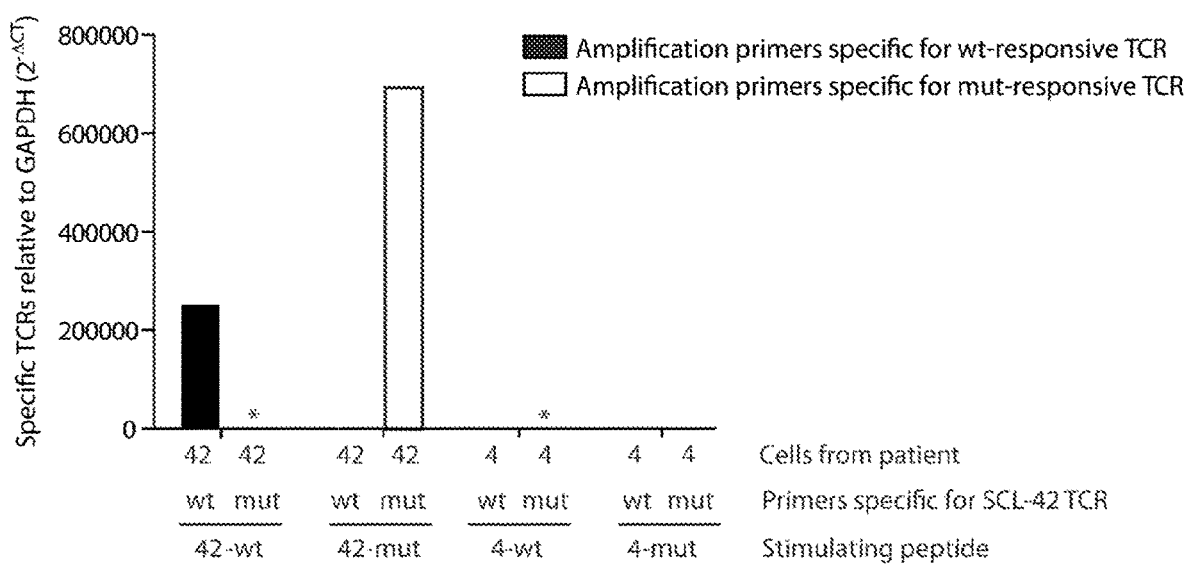

Table S1. Demographic and clinical characteristics grouped by autoantibody status

| | RPC1 (N=8) | TOP1 (N=5) | CENPB (N=3) | p-value |
|---|---|---|---|---|
| Age at scleroderma onset, median (range), years | 49.7 (42.4, 58.8) | 42.4 (37.0, 65.3) | 34.5 (27.3, 45.6) | 0.12 |
| Age at cancer diagnosis, median (range), years | 50.9 (42.3, 54.6) | 65.1 (52.1, 74.6) | 64.2 (43.1, 68.6) | 0.03 |
| Interval between scleroderma onset and cancer diagnosis, median (range), years | -0.1 (-4.2, 2.5) | 13.4 (0.4, 34.0) | 34.0 (-2.5, 36.9) | 0.05 |
| Sex, no. (%) female | 7 (87.5) | 5 (100) | 3 (100) | 1.0 |
| Race, no. (%) | | | | 0.23 |
| White | 8 (100) | 3 (60) | 3 (100) | |
| Black | 0 (0) | 1 (20) | 0 (0) | |
| Asian | 0 (0) | 1 (20) | 0 (0) | |
| Scleroderma classification, no. (%) | | | | 0.003 |
| Limited | 0 (0) | 3 (60) | 3 (100) | |
| Diffuse | 8 (100) | 2 (40) | 0 (0) | |
| Ever smoker, no. (%) | 2 (25) | 2 (40) | 1 (33.3) | 1.0 |
| Maximum mRSS, median (range) | 38 (18, 48) | 6 (4, 27) | 4 (2, 10) | 0.006 |
| Renal crisis, no. (%) | 3 (37.5) | 0 (0) | 0 (0) | 0.24 |
| Immunosuppressive therapy, ever use, no. (%) | | | | |
| Methotrexate | 4 (50) | 1 (20) | 0 (0) | 0.39 |
| Mycophenolate | 6 (75) | 0 (0) | 0 (0) | 0.008 |
| IVIG | 1 (12.5) | 0 (0) | 0 (0) | 1.0 |
| Cyclophosphamide | 1 (12.5) | 2 (40) | 0 (0) | 0.39 |
| Cancer types | 5 Breast<br>1 Lung<br>1 Ovary<br>1 Colon | 4 Breast<br>1 Lung | 1 Breast<br>1 Anal<br>1 Lymphoma | N/A |

RP = Raynaud's phenomenon; mRSS = modified Rodnan skin score

Table S2. Primers used for loss of

| SNP Symbol | Related Gene | Coordinates | Distance (bp)* | Forward primer sequence** | SEQ ID NOS | Reverse primer sequence** | SEQ ID NOS. |
|---|---|---|---|---|---|---|---|
| rs1064608 | POLR3A | chr10:79213314 | -193928 | TGGACACACATCTTCAGATTCA | SEQ ID NO. 7 | CAAGATTTGGACTCAGCAGTTG | SEQ ID NO. 8 |
| rs2579153 | POLR3A | chr10:79218272 | -188970 | GCTACTTTTCTGGCCTGTGG | SEQ ID NO 9 | AGGGAGAACTAAAGGGGAACC | SEQ ID NO. 10 |
| rs2165046 | POLR3A | chr10:79222098 | -185144 | AGAATGCTGTGCTGTGGATG | SEQ ID NO. 11 | GTGCTTCTGGGTCCTGGTT | SEQ ID NO. 12 |
| rs10762763 | POLR3A | chr10:79230809 | -176433 | TGAGGTCAGCTGAGTCTGTGG | SEQ ID NO. 13 | GGATTTTCAGGGCTCCGAGT | SEQ ID NO. 14 |
| rs2288311 | POLR3A | chr10:79235661 | -171581 | GTGTCTGGCCCACCTTTG | SEQ ID NO. 15 | ATTCTTGGTCCATCCTGTGG | SEQ ID NO. 16 |
| rs10824579 | POLR3A | chr10:79260691 | -146551 | CTCCTTTTCCAACTGGGATTC | SEQ ID NO. 17 | CTGCCTCGTGAGGTTCAGA | SEQ ID NO. 18 |
| rs1248888 | POLR3A | chr10:79323400 | -83842 | TGTATCAATGGGCAGCAGTG | SEQ ID NO. 19 | TATGTCATTCTGCCCCCAAG | SEQ ID NO. 20 |
| rs2241547 | POLR3A | chr10:79406970 | -272 | CCGATGGATGTATGCAGTGA | SEQ ID NO. 21 | TTGTTTGCTTGCTTGAAACCT | SEQ ID NO. 22 |
| rs3815891 | POLR3A | chr10:79415795 | 0 | TCTACTTTGGGTGGGGGTGAT | SEQ ID NO. 23 | CTCCAAGACGACGTTAGAACC | SEQ ID NO. 24 |
| rs7094028 | POLR3A | chr10:79419810 | 0 | AACACAAGAAGCGAGGAGCTT | SEQ ID NO. 25 | AAGATCAGCAGGCCAAAGAA | SEQ ID NO. 26 |
| rs2818827 | POLR3A | chr10:79424105 | 0 | TGCTGTGGCTTTGTGTCTC | SEQ ID NO. 27 | GTGTTTGTTCTGGCCCACTC | SEQ ID NO. 28 |
| rs2493568 | POLR3A | chr10:79442860 | 0 | TCGTCTTCTTAGAGGATGCAGTATT | SEQ ID NO. 29 | TGCCTCACTATCACGATCTC | SEQ ID NO. 30 |
| rs4979801 | POLR3A | chr10:79514072 | 54901 | CCGTTGAGATTCATTCTCTCT | SEQ ID NO. 31 | TTGTTTAAAATTCCCTGCTCCT | SEQ ID NO. 32 |
| rs2253909 | POLR3A | chr10:79546360 | 87189 | TGGATTGATTAAACAGATGTTAAGGTT | SEQ ID NO. 33 | CAGAAGGGCCGTTTACACTC | SEQ ID NO. 34 |
| rs2253513 | POLR3A | chr10:79549686 | 90515 | AGCATGTCTGAGCCTCTTTTC | SEQ ID NO. 35 | CAGCAAAGCAGCAACAAAAG | SEQ ID NO. 36 |
| rs2114907 | POLR3A | chr10:79573735 | 114564 | CACTCTCTCCACCACAAGCA | SEQ ID NO. 37 | TTGGCCACCATCAGTAAGAAC | SEQ ID NO. 38 |
| rs1249134 | POLR3A | chr10:79615946 | 156775 | AGAATGGGCCTCTTTGGACT | SEQ ID NO. 39 | CAGGGAGCCTCTTTTCAGGTG | SEQ ID NO. 40 |
| rs1249126 | POLR3A | chr10:79618728 | 159557 | ACACTGTGGGGAGGGGAAAA | SEQ ID NO. 41 | AGCATTTCTGGCCTCCTGT | SEQ ID NO. 42 |
| rs2434123 | POLR3A | chr10:79654802 | 195631 | GCCATCTAGTCTGCGAAAGG | SEQ ID NO. 43 | GTGGGAGAAAGTACAGTTTGAATAAA | SEQ ID NO. 44 |
| rs2665899 | TOP1 | chr20:38898952 | 192170 | CTCCATCGCCCTAGACTGAA | SEQ ID NO. 45 | CTCGCAGGGAGTCCACAC | SEQ ID NO. 46 |
| rs6029375 | TOP1 | chr20:38899311 | -191811 | CCTCATCATCTGGCACCTCT | SEQ ID NO. 47 | AGTGACCTCACACATTGAGGAGT | SEQ ID NO. 48 |
| rs1005533 | TOP1 | chr20:38920524 | -170598 | TCATTTGTGTGGTTTGTGTG | SEQ ID NO. 49 | CTCCTTATGCCTCCCCTGA | SEQ ID NO. 50 |
| rs1109393 | TOP1 | chr20:38927262 | -163860 | GGGAGCTGACCCAATCCAG | SEQ ID NO. 51 | CCTGAAGGTTGCCCATAAA | SEQ ID NO. 52 |
| rs6129395 | TOP1 | chr20:38929002 | -162120 | CCCAGGTCTTCCAAACACAG | SEQ ID NO. 53 | ACTGGAAGCTACACATGGTTT | SEQ ID NO. 54 |
| rs4142346 | TOP1 | chr20:38931100 | -160022 | CCACATTTCAGAGCCTCCAGAG | SEQ ID NO. 55 | GCCAAGGCTACACATCCGTATTT | SEQ ID NO. 56 |
| rs6129700 | TOP1 | chr20:38947279 | -143843 | TTTTAACTACTCATACATCCCCATGTC | SEQ ID NO. 57 | CCCTTCCATCCCGTATTT | SEQ ID NO. 58 |
| rs6124288 | TOP1 | chr20:38954995 | -136127 | CCAAGCCAATTTTCCAAAGA | SEQ ID NO. 59 | GCATCCTCAGGCTGTTTGAC | SEQ ID NO. 60 |
| rs22007309 | TOP1 | chr20:38955031 | -136091 | GGGATGTGCACTGAAACTGAT | SEQ ID NO. 61 | TCAACTCAGCTCAAGGATTGC | SEQ ID NO. 62 |
| rs6072263 | TOP1 | chr20:39011156 | -79966 | TGGGGGACAAACTTTTAGGG | SEQ ID NO. 63 | GCTAGGAGTTGCCTTCAATC | SEQ ID NO. 64 |
| rs6129731 | TOP1 | chr20:39138960 | 0 | CTCTTCACCCCTGACTCACTG | SEQ ID NO. 65 | ACACAAAGGGATACACAACACACA | SEQ ID NO. 66 |
| rs6029549 | TOP1 | chr20:39094101 | 0 | TCTGAAGATGTGGTGTTGGT | SEQ ID NO. 67 | GACATGTCTGGGCATAATTAAACA | SEQ ID NO. 68 |
| rs926545 | TOP1 | chr20:39188109 | 2758 | GTCCAAGAACAGGCCAGATG | SEQ ID NO. 69 | GGAGAAAAGCCAAGTCAGCA | SEQ ID NO. 70 |
| rs3795128 | TOP1 | chr20:39205361 | 20010 | TGCCTCTGCTGTCACTGTTC | SEQ ID NO. 71 | CCTCACTCCCTTCCTCCAAC | SEQ ID NO. 72 |
| rs6093446 | TOP1 | chr20:39207577 | 22226 | TCTGGAGAGCCCTACTTGAG | SEQ ID NO. 73 | AACCCATGGCCCTACTTGAG | SEQ ID NO. 74 |
| rs2076148 | TOP1 | chr20:39214346 | 28995 | GGAGAGGGTGATTGGTGAGA | SEQ ID NO. 75 | GGGAAAAACAGTAAAAGCAGCA | SEQ ID NO. 76 |
| rs6124323 | TOP1 | chr20:39222269 | 36918 | CAGGCTTCTCTCTCCAGGTG | SEQ ID NO. 77 | CCCGGCAGCTACTTAGAGG | SEQ ID NO. 78 |
| rs2235367 | TOP1 | chr20:39227903 | 42552 | TTCCTCGTGCGAGAGAGTG | SEQ ID NO. 79 | CTCTGGTGATGTGATGTCTGT | SEQ ID NO. 80 |
| rs6029610 | TOP1 | chr20:39263536 | 78185 | GAGGCTGGGAACTCAGTGAC | SEQ ID NO. 81 | TTTTGGTTCCTAATTTTCTCTGGA | SEQ ID NO. 82 |
| rs4812493 | TOP1 | chr20:39348159 | 162808 | TGTTGAGAATGCACTTTCTTGAAT | SEQ ID NO. 83 | TAAGTGGCTAATTTTGGGTAATGG | SEQ ID NO. 84 |
| rs4810312 | TOP1 | chr20:39382799 | 197448 | ATTGAATGGGGCTACACCTG | SEQ ID NO. 85 | CCCACCCAAAGCCTAAAGAT | SEQ ID NO. 86 |
| rs6029636 | TOP1 | chr20:39402121 | 216770 | GGTCTTTTGGTCCAGGAAAGC | SEQ ID NO. 87 | GGACAGGTGAGCCCAGGT | SEQ ID NO. 88 |
| rs12625565 | TOP1 | chr20:39402927 | 217576 | TCTGGAGTTGCCTTGAGTGAG | SEQ ID NO. 89 | CTCAGTGACTTGGCGCTTC | SEQ ID NO. 90 |
| rs2072966 | TOP1 | chr20:39419499 | 234148 | TGGAGCTGCCTTGAGTAAC | SEQ ID NO. 91 | CAGCCAGGCACTCACAG | SEQ ID NO. 92 |
|  | TOP1 | chr20:39436751 | 251400 | GATTGGAGCTCGACTCAGAAAT | SEQ ID NO. 93 | CAGGCTGAGGACTTGAGGAG | SEQ ID NO. 94 |

* Distance between the SNP and the indicated gene is listed as "0" if the SNP was within the coding region of the gene. Otherwise, the distance listed represents that between the SNP and the ATG of the coding sequence (negative numbers) or the SNP and the stop codon (numbers >0).

** 5'-cacacaggaaacagctatgaccatg was added to 5'-end of Forward PCR primers and 5'-cgacgtaaaacgacggccagtNNNNNNNNNNNNNNNNNNNNwas added to the 5'-end of Reverse PCR primers to enable the second amplification step, as described in (40).

Table S3. Allelic ratios of SNP loci within and closely surrounding the *TOP1* gene.

| Chr 20 position | SNP ID | Patients with RPC-1 antibodies ||||||||| Patients without RPC-1 antibodies |||||||||
|---|---|---|---|---|---|---|---|---|---|---|---|---|---|---|---|---|---|---|
| | | SCL-1 | SCL-2 | SCL-4 | SCL-13 | SCL-35 | SCL-42 | SCL-81 | SCL-82 | SCL-5 | SCL-8 | SCL-11 | SCL-12 | SCL-19 | SCL-24 | SCL-32 | SCL-85 |
| 38,898,952 | rs2865899 | NI | NI | 103% | NI | NI | NI | 98% | NI | NI | NI | NI | 103% | NI | NI | NI | NI |
| 38,899,311 | rs6029375 | NI | NI | 103% | NI | 102% | 103% | 96% | 103% | NI | NI | NI | NI | 98% | 104% | NI | 104% |
| 38,920,524 | rs1005533 | NI | NI | 102% | NI | 101% | 102% | 93% | 99% | NI | NI | NI | 103% | 96% | 104% | NI | 98% |
| 38,931,100 | rs6129694 | NI | NI | 101% | 95% | NI | NI | NI | NI | NI | NI | NI | NI | 104% | NI | NI | 98% |
| 38,947,279 | rs4142346 | NI | NI | 101% | NI | 102% | 103% | NI | 96% | 103% | NI | NI | NI | NI | NI | NI | 102% |
| 38,954,995 | rs6129700 | NI | NI | 99% | NI | 103% | 101% | NI | NI | NI | NI | NI | NI | NI | 103% | NI | NI |
| 38,955,031 | rs6124288 | NI | NI | 101% | NI | 103% | NI | NI | 101% | NI | NI | NI | NI | 102% | 102% | NI | 98% |
| 39,011,156 | rs2207309 | NI | NI | 104% | 104% | NI | NI | NI | NI | NI | NI | NI | NI | NI | 103% | NI | NI |
| 39,094,101 | rs6129731 | NI | NI | NI | NI | NI | NI | 95% | NI | 93% | 101% | 99% | 101% | NI | NI | NI | 104% |
| 39,138,960 | rs6072263 | 82% | NI | NI | 104% | NI | 102% | 94% | NI | NI | NI | NI | NI | 104% | NI | NI | 104% |
| 39,188,109 | rs6029549 | 82% | NI | NI | 102% | NI | NI | 98% | NI | NI | NI | NI | NI | 98% | NI | NI | 98% |
| 39,205,361 | rs926345 | 100% | NI | NI | 104% | NI | 100% | 95% | NI | 98% | NI | NI | NI | NI | NI | NI | 98% |
| 39,207,577 | rs3795128 | 82% | NI | NI | 104% | NI | 104% | 94% | NI | 103% | NI | NI | NI | 95% | NI | NI | 102% |
| 39,214,346 | rs6093446 | NI | NI | NI | NI | NI | NI | NI | NI | NI | NI | 103% | 96% | NI | NI | NI | 98% |
| 39,222,269 | rs2076148 | 103% | NI | NI | NI | NI | 101% | NI | NI | 92% | NI | NI | NI | NI | NI | NI | NI |
| 39,227,903 | rs6124323 | 82% | NI | NI | 98% | NI | 102% | 86% | NI | 92% | NI | NI | NI | NI | NI | NI | 101% |
| 39,263,536 | rs2235367 | NI | NI | NI | NI | NI | NI | 100% | NI | 96% | NI | NI | NI | NI | NI | NI | NI |
| 39,348,159 | rs6029610 | NI | NI | NI | NI | NI | 101% | 100% | NI | NI | 101% | NI | NI | NI | NI | NI | 100% |
| 39,382,799 | rs4812493 | NI | NI | NI | 94% | NI | 101% | NI | NI | NI | NI | NI | NI | NI | NI | NI | 93% |
| 39,402,927 | rs6029636 | NI | 102% | NI | 95% | 101% | 102% | 103% | NI | NI | NI | 101% | NI | NI | 103% | NI | 99% |
| 39,436,751 | rs2072966 | 82% | 97% | NI | NI | 97% | NI | NI | NI | NI | NI | 93% | 104% | NI | NI | NI | NI |
| Average allelic ratio | | 90% | 99% | 102% | 100% | 101% | 102% | 95% | 100% | 95% | 101% | 99% | 101% | 99% | 103% | NI | 100% |
| Standard deviation (%) | | 9% | 3% | 2% | 4% | 2% | 1% | 5% | 3% | 6% | 0% | 4% | 3% | 4% | 1% | NI | 3% |

*Entries represent the allelic ratios of the indicated SNPs. The values in DNA from normal individuals was 100% +/- 4.40%. Allelic ratios less than 2 standard deviations (SD) from the mean (i.e., <91.2%) are highlighted in red. A tumor was considered to exhibit LOH if more than 3/4 of the informative SNPs exhibited alleic ratios <91.2%. NI: Non-informative, i.e., the SNP was not heterozygous in the normal cells of the patient (see Supplemental material, Materials and Methods).

| Table S4. Synthetic peptides assessed for antibody reactivity | | | |
|---|---|---|---|
| Peptide ID | RPC1 amino acid numbers | Sequence | SEQ ID NO. |
| 1 | 1-15 | MVKEQFRETDVAKKI | SEQ ID NO. 151 |
| 2 | 6-20 | FRETDVAKKISHICF | SEQ ID NO. 152 |
| 3 | 11-25 | VAKKISHICFGMKSP | SEQ ID NO. 153 |
| 4 | 16-30 | SHICFGMKSPEEMRQ | SEQ ID NO. 154 |
| 5 | 21-35 | GMKSPEEMRQQAHIQ | SEQ ID NO. 155 |
| 6 | 26-40 | EEMRQQAHIQVVSKN | SEQ ID NO. 156 |
| 7 | 31-45 | QAHIQVVSKNLYSQD | SEQ ID NO. 157 |
| 8 | 36-50 | VVSKNLYSQDNQHAP | SEQ ID NO. 158 |
| 9 | 41-55 | LYSQDNQHAPLLYGV | SEQ ID NO 159 |
| 10 | 46-60 | NQHAPLLYGVLDHRM | SEQ ID NO 160 |
| 11 | 51-65 | LLYGVLDHRMGTSEK | SEQ ID NO. 161 |
| 12 | 56-70 | LDHRMGTSEKDRPCE | SEQ ID NO. 162 |
| 13 | 61-75 | GTSEKDRPCETCGKN | SEQ ID NO. 163 |
| 14 | 66-80 | DRPCETCGKNLADCL | SEQ ID NO. 164 |
| 15 | 71-85 | TCGKNLADCLGHYGY | SEQ ID NO. 165 |
| 16 | 76-90 | LADCLGHYGYIDLEL | SEQ ID NO. 166 |
| 17 | 81-95 | GHYGYIDLELPCFHV | SEQ ID NO. 167 |
| 18 | 86-100 | IDLELPCFHVGYFRA | SEQ ID NO. 168 |
| 19 | 91-105 | PCFHVGYFRAVIGIL | SEQ ID NO. 169 |
| 20 | 96-110 | GYFRAVIGILQMICK | SEQ ID NO. 170 |
| 21 | 101-115 | VIGILQMICKTCCHI | SEQ ID NO. 171 |
| 22 | 106-120 | QMICKTCCHIMLSQE | SEQ ID NO. 172 |
| 23 | 111-125 | TCCHIMLSQEEKKQF | SEQ ID NO. 173 |
| 24 | 116-130 | MLSQEEKKQFLDYLK | SEQ ID NO. 174 |
| 25 | 121-135 | EKKQFLDYLKRPGLT | SEQ ID NO. 175 |
| 26 | 126-140 | LDYLKRPGLTYLQKR | SEQ ID NO. 176 |
| 27 | 131-145 | RPGLTYLQKRGLKKK | SEQ ID NO. 177 |
| 28 | 136-150 | YLQKRGLKKKISDKC | SEQ ID NO. 178 |
| 29 | 141-155 | GLKKKISDKCRKKNI | SEQ ID NO. 179 |
| 30 | 146-160 | ISDKCRKKNICHHCG | SEQ ID NO. 180 |
| 31 | 151-165 | RKKNICHHCGAFNGT | SEQ ID NO. 181 |
| 32 | 156-170 | CHHCGAFNGTVKKCG | SEQ ID NO. 182 |
| 33 | 161-175 | AFNGTVKKCGLLKII | SEQ ID NO. 183 |
| 34 | 166-180 | VKKCGLLKIIHEKYK | SEQ ID NO. 184 |
| 35 | 171-185 | LLKIIHEKYKTNKKV | SEQ ID NO. 185 |
| 36 | 176-190 | HEKYKTNKKVVDPIV | SEQ ID NO. 186 |
| 37 | 181-195 | TNKKVVDPIVSNFLQ | SEQ ID NO. 187 |
| 38 | 186-200 | VDPIVSNFLQSFETA | SEQ ID NO. 188 |
| 39 | 191-205 | SNFLQSFETAIEHNK | SEQ ID NO. 189 |
| 40 | 196-210 | SFETAIEHNKEVEPL | SEQ ID NO. 190 |
| 41 | 201-215 | IEHNKEVEPLLGRAQ | SEQ ID NO. 191 |
| 42 | 206-220 | EVEPLLGRAQENLNP | SEQ ID NO. 192 |
| 43 | 211-225 | LGRAQENLNPLVVLN | SEQ ID NO. 193 |
| 44 | 216-230 | ENLNPLVVLNLFKRI | SEQ ID NO. 194 |
| 45 | 221-235 | LVVLNLFKRIPAEDV | SEQ ID NO. 195 |
| 46 | 226-240 | LFKRIPAEDVPLLLM | SEQ ID NO. 196 |
| 47 | 231-245 | PAEDVPLLLMNPEAG | SEQ ID NO. 197 |
| 48 | 236-250 | PLLLMNPEAGKPSDL | SEQ ID NO. 198 |
| 49 | 241-255 | NPEAGKPSDLILTRL | SEQ ID NO. 199 |

FIG. 14-2

| 50 | 246-260 | KPSDLILTRLLVPPL | SEQ ID NO. 200 |
|---|---|---|---|
| 51 | 251-265 | ILTRLLVPPLCIRPS | SEQ ID NO. 201 |
| 52 | 256-270 | LVPPLCIRPSVVSDL | SEQ ID NO. 202 |
| 53 | 261-275 | CIRPSVVSDLKSGTN | SEQ ID NO. 203 |
| 54 | 266-280 | VVSDLKSGTNEDDLT | SEQ ID NO. 204 |
| 55 | 271-285 | KSGTNEDDLTMKLTE | SEQ ID NO. 205 |
| 56 | 276-290 | EDDLTMKLTEIIFLN | SEQ ID NO. 206 |
| 57 | 281-295 | MKLTEIIFLNDVIKK | SEQ ID NO. 207 |
| 58 | 286-300 | IIFLNDVIKKHRISG | SEQ ID NO. 208 |
| 59 | 291-305 | DVIKKHRISGAKTQM | SEQ ID NO. 209 |
| 60 | 296-310 | HRISGAKTQMIMEDW | SEQ ID NO. 210 |
| 61 | 301-315 | AKTQMIMEDWDFLQL | SEQ ID NO. 211 |
| 62 | 306-320 | IMEDWDFLQLQCALY | SEQ ID NO. 212 |
| 63 | 311-325 | DFLQLQCALYINSEL | SEQ ID NO. 213 |
| 64 | 316-330 | QCALYINSELSGIPL | SEQ ID NO. 214 |
| 65 | 321-335 | INSELSGIPLNMAPK | SEQ ID NO. 215 |
| 66 | 326-340 | SGIPLNMAPKKWTRG | SEQ ID NO. 216 |
| 67 | 331-345 | NMAPKKWTRGFVQRL | SEQ ID NO. 217 |
| 68 | 336-350 | KWTRGFVQRLKGKQG | SEQ ID NO. 218 |
| 69 | 341-355 | FVQRLKGKQGRFRGN | SEQ ID NO. 219 |
| 70 | 346-360 | KGKQGRFRGNLSGKR | SEQ ID NO. 220 |
| 71 | 351-365 | RFRGNLSGKRVDFSG | SEQ ID NO. 221 |
| 72 | 356-370 | LSGKRVDFSGRTVIS | SEQ ID NO. 222 |
| 73 | 361-375 | VDFSGRTVISPDPNL | SEQ ID NO. 223 |
| 74 | 366-380 | RTVISPDPNLRIDEV | SEQ ID NO. 224 |
| 75 | 371-385 | PDPNLRIDEVAVPVH | SEQ ID NO. 225 |
| 76 | 376-390 | RIDEVAVPVHVAKIL | SEQ ID NO. 226 |
| 77 | 381-395 | AVPVHVAKILTFPEK | SEQ ID NO. 227 |
| 78 | 386-400 | VAKILTFPEKVNKAN | SEQ ID NO. 228 |
| 79 | 391-405 | TFPEKVNKANINFLR | SEQ ID NO. 229 |
| 80 | 396-410 | VNKANINFLRKLVQN | SEQ ID NO. 230 |
| 81 | 401-415 | INFLRKLVQNGPEVH | SEQ ID NO. 231 |
| 82 | 406-420 | KLVQNGPEVHPGANF | SEQ ID NO. 232 |
| 83 | 411-425 | GPEVHPGANFIQQRH | SEQ ID NO. 233 |
| 84 | 416-430 | PGANFIQQRHTQMKR | SEQ ID NO. 234 |
| 85 | 421-435 | IQQRHTQMKRFLKYG | SEQ ID NO. 235 |
| 86 | 426-440 | TQMKRFLKYGNREKM | SEQ ID NO. 236 |
| 87 | 431-445 | FLKYGNREKMAQELK | SEQ ID NO. 237 |
| 88 | 436-450 | NREKMAQELKYGDIV | SEQ ID NO. 238 |
| 89 | 441-455 | AQELKYGDIVERHLI | SEQ ID NO. 239 |
| 90 | 446-460 | YGDIVERHLIDGDVV | SEQ ID NO. 240 |
| 91 | 451-465 | ERHLIDGDVVLFNRQ | SEQ ID NO. 241 |
| 92 | 456-470 | DGDVVLFNRQPSLHK | SEQ ID NO. 242 |
| 93 | 461-475 | LFNRQPSLHKLSIMA | SEQ ID NO. 243 |
| 94 | 466-480 | PSLHKLSIMAHLARV | SEQ ID NO. 244 |
| 95 | 471-485 | LSIMAHLARVKPHRT | SEQ ID NO. 245 |
| 96 | 476-490 | HLARVKPHRTFRFNE | SEQ ID NO 246 |
| 97 | 481-495 | KPHRTFRFNECVCTP | SEQ ID NO. 247 |
| 98 | 486-500 | FRFNECVCTPYNADF | SEQ ID NO. 248 |
| 99 | 491-505 | CVCTPYNADFDGDEM | SEQ ID NO. 249 |
| 100 | 496-510 | YNADFDGDEMNLHLP | SEQ ID NO. 250 |
| 101 | 501-515 | DGDEMNLHLPQTEEA | SEQ ID NO. 251 |

FIG. 14-3

| 102 | 506-520 | NLHLPQTEEAKAEAL | SEQ ID NO. 252 |
|---|---|---|---|
| 103 | 511-525 | QTEEAKAEALVLMGT | SEQ ID NO. 253 |
| 104 | 516-530 | KAEALVLMGTKANLV | SEQ ID NO. 254 |
| 105 | 521-535 | VLMGTKANLVTPRNG | SEQ ID NO. 255 |
| 106 | 526-540 | KANLVTPRNGEPLIA | SEQ ID NO. 256 |
| 107 | 531-545 | TPRNGEPLIAAIQDF | SEQ ID NO. 257 |
| 108 | 536-550 | EPLIAAIQDFLTGAY | SEQ ID NO. 258 |
| 109 | 541-555 | AIQDFLTGAYLLTLK | SEQ ID NO. 259 |
| 110 | 546-560 | LTGAYLLTLKDTFFD | SEQ ID NO. 260 |
| 111 | 551-565 | LLTLKDTFFDRAKAC | SEQ ID NO. 261 |
| 112 | 556-570 | DTFFDRAKACQIIAS | SEQ ID NO. 262 |
| 113 | 561-575 | RAKACQIIASILVGK | SEQ ID NO. 263 |
| 114 | 566-580 | QIIASILVGKDEKIK | SEQ ID NO. 264 |
| 115 | 571-585 | ILVGKDEKIKVRLPP | SEQ ID NO. 265 |
| 116 | 576-590 | DEKIKVRLPPPTILK | SEQ ID NO. 266 |
| 117 | 581-595 | VRLPPPTILKPVTLW | SEQ ID NO. 267 |
| 118 | 586-600 | PTILKPVTLWTGKQI | SEQ ID NO. 268 |
| 119 | 591-605 | PVTLWTGKQIFSVIL | SEQ ID NO. 269 |
| 120 | 596-610 | TGKQIFSVILRPSDD | SEQ ID NO. 270 |
| 121 | 601-615 | FSVILRPSDDNPVRA | SEQ ID NO. 271 |
| 122 | 606-620 | RPSDDNPVRANLRTK | SEQ ID NO. 272 |
| 123 | 611-625 | NPVRANLRTKGKQYC | SEQ ID NO. 273 |
| 124 | 616-630 | NLRTKGKQYCGKGED | SEQ ID NO. 274 |
| 125 | 621-635 | GKQYCGKGEDLCAND | SEQ ID NO. 275 |
| 126 | 626-640 | GKGEDLCANDSYVTI | SEQ ID NO. 276 |
| 127 | 631-645 | LCANDSYVTIQNSEL | SEQ ID NO. 277 |
| 128 | 636-650 | SYVTIQNSELMSGSM | SEQ ID NO. 278 |
| 129 | 641-655 | QNSELMSGSMDKGTL | SEQ ID NO. 279 |
| 130 | 646-660 | MSGSMDKGTLGSGSK | SEQ ID NO. 280 |
| 131 | 651-665 | DKGTLGSGSKNNIFY | SEQ ID NO. 281 |
| 132 | 656-670 | GSGSKNNIFYILLRD | SEQ ID NO. 282 |
| 133 | 661-675 | NNIFYILLRDWGQNE | SEQ ID NO. 283 |
| 134 | 666-680 | ILLRDWGQNEAADAM | SEQ ID NO. 284 |
| 135 | 671-685 | WGQNEAADAMSRLAR | SEQ ID NO. 285 |
| 136 | 676-690 | AADAMSRLARLAPVY | SEQ ID NO. 286 |
| 137 | 681-695 | SRLARLAPVYLSNRG | SEQ ID NO. 287 |
| 138 | 686-700 | LAPVYLSNRGFSIGI | SEQ ID NO. 288 |
| 139 | 691-705 | LSNRGFSIGIGDVTP | SEQ ID NO. 289 |
| 140 | 696-710 | FSIGIGDVTPGQGLL | SEQ ID NO. 290 |
| 141 | 701-715 | GDVTPGQGLLKAKYE | SEQ ID NO. 291 |
| 142 | 706-720 | GQGLLKAKYELLNAG | SEQ ID NO. 292 |
| 143 | 711-725 | KAKYELLNAGYKKCD | SEQ ID NO. 293 |
| 144 | 716-730 | LLNAGYKKCDEYIEA | SEQ ID NO. 294 |
| 145 | 721-735 | YKKCDEYIEALNTGK | SEQ ID NO. 295 |
| 146 | 726-740 | EYIEALNTGKLQQQP | SEQ ID NO. 296 |
| 147 | 731-745 | LNTGKLQQQPGCTAE | SEQ ID NO. 297 |
| 148 | 736-750 | LQQQPGCTAEETLEA | SEQ ID NO. 298 |
| 149 | 741-755 | GCTAEETLEALILKE | SEQ ID NO. 299 |
| 150 | 746-760 | ETLEALILKELSVIR | SEQ ID NO. 300 |
| 151 | 751-765 | LILKELSVIRDHAGS | SEQ ID NO. 301 |
| 152 | 756-770 | LSVIRDHAGSACLRE | SEQ ID NO. 302 |
| 153 | 761-775 | DHAGSACLRELDKSN | SEQ ID NO. 303 |

Fig. 14-4

| 154 | 766-780 | ACLRELDKSNSPLTM | SEQ ID NO. 304 |
|---|---|---|---|
| 155 | 771-785 | LDKSNSPLTMALCGS | SEQ ID NO. 305 |
| 156 | 776-790 | SPLTMALCGSKGSFI | SEQ ID NO. 306 |
| 157 | 781-795 | ALCGSKGSFINISQM | SEQ ID NO. 307 |
| 158 | 786-800 | KGSFINISQMIACVG | SEQ ID NO. 308 |
| 159 | 791-805 | NISQMIACVGQQAIS | SEQ ID NO. 309 |
| 160 | 796-810 | IACVGQQAISGSRVP | SEQ ID NO. 310 |
| 161 | 801-815 | QQAISGSRVPDGFEN | SEQ ID NO. 311 |
| 162 | 806-820 | GSRVPDGFENRSLPH | SEQ ID NO. 312 |
| 163 | 811-825 | DGFENRSLPHFEKHS | SEQ ID NO. 313 |
| 164 | 816-830 | RSLPHFEKHSKLPAA | SEQ ID NO. 314 |
| 165 | 821-835 | FEKHSKLPAAKGFVA | SEQ ID NO. 315 |
| 166 | 826-840 | KLPAAKGFVANSFYS | SEQ ID NO. 316 |
| 167 | 831-845 | KGFVANSFYSGLTPT | SEQ ID NO. 317 |
| 168 | 836-850 | NSFYSGLTPTEFFFH | SEQ ID NO. 318 |
| 169 | 841-855 | GLTPTEFFFHTMAGR | SEQ ID NO. 319 |
| 170 | 846-860 | EFFFHTMAGREGLVD | SEQ ID NO. 320 |
| 171 | 851-865 | TMAGREGLVDTAVKT | SEQ ID NO. 321 |
| 172 | 856-870 | EGLVDTAVKTAETGY | SEQ ID NO. 322 |
| 173 | 861-875 | TAVKTAETGYMQRRL | SEQ ID NO. 323 |
| 174 | 866-880 | AETGYMQRRLVKSLE | SEQ ID NO. 324 |
| 175 | 871-885 | MQRRLVKSLEDLCSQ | SEQ ID NO. 325 |
| 176 | 876-890 | VKSLEDLCSQYDLTV | SEQ ID NO. 326 |
| 177 | 881-895 | DLCSQYDLTVRSSTG | SEQ ID NO. 327 |
| 178 | 886-900 | YDLTVRSSTGDIIQF | SEQ ID NO. 328 |
| 179 | 891-905 | RSSTGDIIQFIYGGD | SEQ ID NO. 329 |
| 180 | 896-910 | DIIQFIYGGDGLDPA | SEQ ID NO. 330 |
| 181 | 901-915 | IYGGDGLDPAAMEGK | SEQ ID NO. 331 |
| 182 | 906-920 | GLDPAAMEGKDEPLE | SEQ ID NO. 332 |
| 183 | 911-925 | AMEGKDEPLEFKRVL | SEQ ID NO. 333 |
| 184 | 916-930 | DEPLEFKRVLDNIKA | SEQ ID NO. 334 |
| 185 | 921-935 | FKRVLDNIKAVFPCP | SEQ ID NO. 335 |
| 186 | 926-940 | DNIKAVFPCPSEPAL | SEQ ID NO. 336 |
| 187 | 931-945 | VFPCPSEPALSKNEL | SEQ ID NO. 337 |
| 188 | 936-950 | SEPALSKNELILTTE | SEQ ID NO. 338 |
| 189 | 941-955 | SKNELILTTESIMKK | SEQ ID NO. 339 |
| 190 | 946-960 | ILTTESIMKKSEFLC | SEQ ID NO. 340 |
| 191 | 951-965 | SIMKKSEFLCKYMRA | SEQ ID NO. 341 |
| 192 | 956-970 | SEFLCKYMRAQMEPGV | SEQ ID NO. 342 |
| 193 | 961-975 | KYMRAQMEPGSAVGA | SEQ ID NO. 343 |
| 194 | 966-980 | QMEPGSAVGALCAQS | SEQ ID NO. 344 |
| 195 | 971-985 | SAVGALCAQSIGEPG | SEQ ID NO. 345 |
| 196 | 976-990 | LCAQSIGEPGTQMTL | SEQ ID NO. 346 |
| 197 | 981-995 | IGEPGTQMTLKTFHF | SEQ ID NO. 347 |
| 198 | 986-1000 | TQMTLKTFHFAGVAS | SEQ ID NO. 348 |
| 199 | 991-1005 | KTFHFAGVASMNITL | SEQ ID NO. 349 |
| 200 | 996-1010 | AGVASMNITLGVPRI | SEQ ID NO. 350 |
| 201 | 1001-1015 | MNITLGVPRIKEIIN | SEQ ID NO. 351 |
| 202 | 1006-1020 | GVPRIKEIINASKAI | SEQ ID NO. 352 |
| 203 | 1011-1025 | KEIINASKAICQDSF | SEQ ID NO. 353 |
| 204 | 1016-1130 | ASKAICQDSFLQEIK | SEQ ID NO. 354 |
| 205 | 1021-1035 | CQDSFLQEIKKFIKG | SEQ ID NO. 355 |

Fig. 14-5

| 206 | 1026-1040 | LQEIKKFIKGVSEKI | SEQ ID NO. 356 |
|---|---|---|---|
| 207 | 1031-1045 | KFIKGVSEKIKKTRD | SEQ ID NO. 357 |
| 208 | 1036-1050 | VSEKIKKTRDKYGIN | SEQ ID NO. 358 |
| 209 | 1041-1055 | KKTRDKYGINDNGTT | SEQ ID NO. 359 |
| 210 | 1046-1060 | KYGINDNGTTEPRVL | SEQ ID NO. 360 |
| 211 | 1051-1065 | DNGTTEPRVLYQLDR | SEQ ID NO. 361 |
| 212 | 1056-1070 | EPRVLYQLDRITPTQ | SEQ ID NO. 362 |
| 213 | 1061-1075 | YQLDRITPTQVEKFL | SEQ ID NO. 363 |
| 214 | 1066-1080 | ITPTQVEKFLETCRD | SEQ ID NO. 364 |
| 215 | 1071-1085 | VEKFLETCRDSTPII | SEQ ID NO. 365 |
| 216 | 1076-1090 | ETCRDSTPIITAQLD | SEQ ID NO. 366 |
| 217 | 1081-1095 | STPIITAQLDKDDDA | SEQ ID NO. 367 |
| 218 | 1086-1100 | TAQLDKDDDADYARL | SEQ ID NO. 368 |
| 219 | 1091-1105 | KDDDADYARLVKGRI | SEQ ID NO. 369 |
| 220 | 1096-1110 | DYARLVKGRIEKTLL | SEQ ID NO. 370 |
| 221 | 1101-1115 | VKGRIEKTLLGEISE | SEQ ID NO. 371 |
| 222 | 1106-1120 | EKTLLGEISEYIEEV | SEQ ID NO. 372 |
| 223 | 1111-1125 | GEISEYIEEVFLPDD | SEQ ID NO. 373 |
| 224 | 1116-1130 | YIEEVFLPDDCFILV | SEQ ID NO. 374 |
| 225 | 1121-1135 | FLPDDCFILVKLSLE | SEQ ID NO. 375 |
| 226 | 1126-1140 | CFILVKLSLERIRLL | SEQ ID NO. 376 |
| 227 | 1131-1145 | KLSLERIRLLRLEVN | SEQ ID NO. 377 |
| 228 | 1136-1150 | RIRLLRLEVNAETVR | SEQ ID NO. 378 |
| 229 | 1141-1155 | RLEVNAETVRYSICT | SEQ ID NO. 379 |
| 230 | 1146-1160 | AETVRYSICTSKLRV | SEQ ID NO. 380 |
| 231 | 1151-1165 | YSICTSKLRVKPGDV | SEQ ID NO. 381 |
| 232 | 1156-1170 | SKLRVKPGDVAVHGE | SEQ ID NO. 382 |
| 233 | 1161-1175 | KPGDVAVHGEAVVCV | SEQ ID NO. 383 |
| 234 | 1166-1180 | AVHGEAVVCVTPREN | SEQ ID NO. 384 |
| 235 | 1171-1185 | AVVCVTPRENSKSSM | SEQ ID NO. 385 |
| 236 | 1176-1190 | TPRENSKSSMYYVLQ | SEQ ID NO. 386 |
| 237 | 1181-1195 | SKSSMYYVLQFLKED | SEQ ID NO. 387 |
| 238 | 1186-1200 | YYVLQFLKEDLPKVV | SEQ ID NO. 388 |
| 239 | 1191-1205 | FLKEDLPKVVVQGIP | SEQ ID NO. 389 |
| 240 | 1196-1210 | LPKVVVQGIPEVSRA | SEQ ID NO. 390 |
| 241 | 1201-1215 | VQGIPEVSRAVIHID | SEQ ID NO. 391 |
| 242 | 1206-1220 | EVSRAVIHIDEQSGK | SEQ ID NO. 392 |
| 43 | 1211-1225 | VIHIDEQSGKEKYKL | SEQ ID NO. 393 |
| 244 | 1216-1230 | EQSGKEKYKLLVEGD | SEQ ID NO. 394 |
| 245 | 1221-1235 | EKYKLLVEGDNLRAV | SEQ ID NO. 395 |
| 246 | 1226-1240 | LVEGDNLRAVMATHG | SEQ ID NO. 396 |
| 247 | 1231-1245 | NLRAVMATHGVKGTR | SEQ ID NO. 397 |
| 248 | 1236-1250 | MATHGVKGTRTTSNN | SEQ ID NO. 398 |
| 249 | 1241-1255 | VKGTRTTSNNTYEVE | SEQ ID NO. 399 |
| 250 | 1246-1260 | TTSNNTYEVEKTLGI | SEQ ID NO. 400 |
| 251 | 1251-1265 | TYEVEKTLGIEAART | SEQ ID NO. 401 |
| 252 | 1256-1270 | KTLGIEAARTTIINE | SEQ ID NO. 402 |
| 253 | 1261-1275 | EAARTTIINEIQYTM | SEQ ID NO. 403 |
| 254 | 1266-1280 | TIINEIQYTMVNHGM | SEQ ID NO. 404 |
| 255 | 1271-1285 | IQYTMVNHGMSIDRR | SEQ ID NO. 405 |
| 256 | 1276-1290 | VNHGMSIDRRHVMLL | SEQ ID NO. 406 |
| 257 | 1281-1295 | SIDRRHVMLLSDLMT | SEQ ID NO. 407 |

Fig. 14-6

| 258 | 1286-1300 | HVMLLSDLMTYKGEV | SEQ ID NO. 408 |
|---|---|---|---|
| 259 | 1291-1305 | SDLMTYKGEVLGITR | SEQ ID NO. 409 |
| 260 | 1296-1310 | YKGEVLGITRFGLAK | SEQ ID NO. 410 |
| 261 | 1301-1315 | LGITRFGLAKMKESV | SEQ ID NO. 411 |
| 262 | 1306-1320 | FGLAKMKESVLMLAS | SEQ ID NO. 412 |
| 263 | 1311-1325 | MKESVLMLASFEKTA | SEQ ID NO. 413 |
| 264 | 1316-1330 | LMLASFEKTADHLFD | SEQ ID NO. 414 |
| 265 | 1321-1335 | FEKTADHLFDAAYFG | SEQ ID NO. 415 |
| 266 | 1326-1340 | DHLFDAAYFGQKDSV | SEQ ID NO. 416 |
| 267 | 1331-1345 | AAYFGQKDSVCGVSE | SEQ ID NO. 417 |
| 268 | 1336-1350 | QKDSVCGVSECIIMG | SEQ ID NO. 418 |
| 269 | 1341-1355 | CGVSECIIMGIPMNI | SEQ ID NO. 419 |
| 270 | 1346-1360 | CIIMGIPMNIGTGLF | SEQ ID NO. 420 |
| 271 | 1351-1365 | IPMNIGTGLFKLLHK | SEQ ID NO. 421 |
| 272 | 1356-1370 | GTGLFKLLHKADRDP | SEQ ID NO. 422 |
| 273 | 1361-1375 | KLLHKADRDPNPPKR | SEQ ID NO. 423 |
| 274 | 1366-1380 | ADRDPNPPKRPLIFD | SEQ ID NO. 424 |
| 275 | 1371-1385 | NPPKRPLIFDTNEFH | SEQ ID NO. 425 |
| 276 | 1376-1390 | PLIFDTNEFHIPLVT | SEQ ID NO. 426 |
| I104T mutant #1 | 91-105 | PCFHVGYFRAVIGTL | SEQ ID NO. 427 |
| I104T mutant #2 | 96-110 | GYFRAVIGTLQMICK | SEQ ID NO. 428 |
| I104T mutant #3 | 101-115 | VIGTLQMICKTCCHI | SEQ ID NO. 429 |
| E1072Q mutant #1 | 1061-1075 | YQLDRITPTQVQKFL | SEQ ID NO. 430 |
| E1072Q mutant #2 | 1066-1080 | ITPTQVQKFLETCRD | SEQ ID NO. 431 |
| E1072Q mutant #3 | 1071-1085 | VQKFLETCRDSTPII | SEQ ID NO. 432 |
| K1365N #1 | 1351-1365 | IPMNIGTGLFKLLHN | SEQ ID NO. 433 |
| K1365N #2 | 1356-1370 | GTGLFKLLHNADRDP | SEQ ID NO. 434 |
| K1365N #3 | 1361-1375 | KLLHNADRDPNPPKR | SEQ ID NO. 435 |

Table S5. MHC types of the patients with *RPOL3A* mutations

| Patient # | MHC |
|---|---|
| SCL-2 | A 1/3 |
| | B 7/8 |
| | C 7/7 |
| | DRB1 3/15 |
| | DQB1 2/6 |
| | |
| SCL-4 | A 2/26 |
| | B 35/56 |
| | C 1/4 |
| | DRB1 1/11 |
| | DQB1 3/5 |
| | |
| SCL-42 | A 1/29 |
| | B 37/44 |
| | C 6/16 |
| | DRB1 7/10 |
| | DQB1 2/5 |

Table S6: Patient-specific MHC class I and class II peptides with highest predicted binding affinity

| Patient | Mutation | HLA Allele | wt peptide | SEQ ID NOS. | IC50 | mut peptide | SEQ ID NO. | IC50 | Prediction Method |
|---|---|---|---|---|---|---|---|---|---|
| SCL-2 | E1072Q | A*0101 | TLGVPRIKEI | SEQ ID NO. 103 | 33377 | TLGVPRIKQI | SEQ ID NO. 127 | 32553 | ANN |
|  |  | A*0301 | RIKEIINASK | SEQ ID NO. 104 | 78 | RIKQIINASK | SEQ ID NO. 128 | 58 | ANN |
|  |  | B*0702 | VPRIKEIINAS | SEQ ID NO. 105 | 1407 | VPRIKQIINAS | SEQ ID NO. 129 | 953 | CombLib |
|  |  | B*0801 | VPRIKEII | SEQ ID NO. 106 | 759 | VPRIKQII | SEQ ID NO. 130 | 447 | CombLib |
|  |  | C*0701 | ITLGVPRIKEI | SEQ ID NO. 107 | 1539 | ITLGVPRIKQI | SEQ ID NO. 131 | 2221 | ANN |
|  |  | C*0702 | SMNITLGVPRIKEI | SEQ ID NO. 108 | 11367 | SMNITLGVPRIKQI | SEQ ID NO. 132 | 11587 | ANN |
|  |  | DR*0301 | GVPRIKEIINASKAIST | SEQ ID NO. 109 | 8235 | GVPRIKQIINASKAIST | SEQ ID NO. 133 | 6854 | SMM |
|  |  | DR*1501 | GVPRIKEIINASKAIST | SEQ ID NO. 109 | 591 | GVPRIKQIINASKAIST | SEQ ID NO. 133 | 416 | SMM |
| SCL-4 | K1365N | A*0201 | GLFKLLHKA | SEQ ID NO. 111 | 46 | GLFKLLHNA | SEQ ID NO. 135 | 27 | ANN |
|  |  | A*2601 | GTGLFKLLHK | SEQ ID NO. 112 | 31605 | GTGLFKLLHN | SEQ ID NO. 136 | 33271 | ANN |
|  |  | B*3501 | FKLLHKAD | SEQ ID NO. 113 | 15618 | FKLLHNAD | SEQ ID NO. 137 | 4544 | SMM |
|  |  | B*5601 | TGLFKLLHKA | SEQ ID NO. 114 | 24218 | TGLFKLLHNA | SEQ ID NO. 138 | 21971 | NetMHCpan |
|  |  | C*0102 | KADRDPNPPKRPL | SEQ ID NO. 115 | 13637 | NADRDPNPPKRPL | SEQ ID NO. 139 | 21533 | NetMHCpan |
|  |  | C*0401 | KLLHKADRDPNPPK | SEQ ID NO. 116 | 7973 | KLLHNADRDPNPPK | SEQ ID NO. 140 | 7794 | ANN |
|  |  | DR*0101 | IGTGLFKLLHKADRDPN | SEQ ID NO. 117 | 69 | IGTGLFKLLHNADRDPN | SEQ ID NO. 141 | 4 | CombLib |
|  |  | DR*1101 | IGTGLFKLLHKADRDPN | SEQ ID NO. 117 | 26 | IGTGLFKLLHNADRDPN | SEQ ID NO. 141 | 113 | SMM |
| SCL-42 | I104T | A*0101 | VIGILQMI | SEQ ID NO. 119 | 21734 | VIGTLQMI | SEQ ID NO. 143 | 21971 | NetMHCpan |
|  |  | A*2902 | YFRAVIGILQM | SEQ ID NO. 120 | 1158 | YFRAVIGTLQM | SEQ ID NO. 144 | 743 | NetMHCpan |
|  |  | B*3701 | FRAVIGIL | SEQ ID NO. 121 | 3417 | FRAVIGTL | SEQ ID NO. 145 | 3237 | NetMHCpan |
|  |  | B*4403 | AVIGILQM | SEQ ID NO. 122 | 22452 | AVIGTLQM | SEQ ID NO. 146 | 21501 | NetMHCpan |
|  |  | C*0602 | FRAVIGILQMI | SEQ ID NO. 123 | 53 | FRAVIGTLQMI | SEQ ID NO. 147 | 40 | ANN |
|  |  | C*1601 | YFRAVIGILQM | SEQ ID NO. 124 | 822 | YFRAVIGTLQM | SEQ ID NO. 148 | 458 | NetMHCpan |
|  |  | DR*0701 | FHVGYFRAVIGILQMI | SEQ ID NO. 96 | 0 | FHVGYFRAVIGTLQMI | SEQ ID NO. 95 | 0.5 | CombLib |
|  |  | DR*1001 | FHVGYFRAVIGILQMI | SEQ ID NO. 96 | 54 | FHVGYFRAVIGTLQMI | SEQ ID NO. 95 | 21 | NetMHCpan |

Moderate to high affinity peptides are in bold
ANN = artificial neural network
CombLib = scoring matrices derived from combinatorial peptide libraries
SMM = stabilized matrix method

SEQUENCE LISTING

<160> NUMBER OF SEQ ID NOS: 435

<210> SEQ ID NO 1
<211> LENGTH: 19
<212> TYPE: DNA
<213> ORGANISM: Artificial Sequence
<220> FEATURE:
<223> OTHER INFORMATION: probe

<400> SEQUENCE: 1
actgaagctt tctttggac                                                    19

<210> SEQ ID NO 2
<211> LENGTH: 19
<212> TYPE: DNA
<213> ORGANISM: Artificial Sequence
<220> FEATURE:
<223> OTHER INFORMATION: primers

<400> SEQUENCE: 2
gcaccgggac agtgatgaa                                                    19

<210> SEQ ID NO 3
<211> LENGTH: 25
<212> TYPE: DNA
<213> ORGANISM: Artificial Sequence
<220> FEATURE:
<223> OTHER INFORMATION: primers

<400> SEQUENCE: 3
ggtcctctac aactgtgagt ttggt                                             25

<210> SEQ ID NO 4
<211> LENGTH: 19
<212> TYPE: DNA
<213> ORGANISM: Artificial Sequence
<220> FEATURE:
<223> OTHER INFORMATION: probe

<400> SEQUENCE: 4
acagtaaatc agccccagc                                                    19

<210> SEQ ID NO 5
<211> LENGTH: 19
<212> TYPE: DNA
<213> ORGANISM: Artificial Sequence
<220> FEATURE:
<223> OTHER INFORMATION: primers

<400> SEQUENCE: 5
tgtgtgccac cagcagaga                                                    19

<210> SEQ ID NO 6
<211> LENGTH: 21
<212> TYPE: DNA
<213> ORGANISM: Artificial Sequence
<220> FEATURE:
<223> OTHER INFORMATION: primers

<400> SEQUENCE: 6
agtcgagtcc catcaccaaa a                                                 21

```
<210> SEQ ID NO 7
<211> LENGTH: 23
<212> TYPE: DNA
<213> ORGANISM: Artificial Sequence
<220> FEATURE:
<223> OTHER INFORMATION: primers

<400> SEQUENCE: 7
tggacacaca tctttcagat tca                                          23

<210> SEQ ID NO 8
<211> LENGTH: 22
<212> TYPE: DNA
<213> ORGANISM: Artificial Sequence
<220> FEATURE:
<223> OTHER INFORMATION: primers

<400> SEQUENCE: 8
caagatttgg actcagcagt tg                                           22

<210> SEQ ID NO 9
<211> LENGTH: 20
<212> TYPE: DNA
<213> ORGANISM: Artificial Sequence
<220> FEATURE:
<223> OTHER INFORMATION: primers

<400> SEQUENCE: 9
gctacttttc tggcctgtgg                                              20

<210> SEQ ID NO 10
<211> LENGTH: 21
<212> TYPE: DNA
<213> ORGANISM: Artificial Sequence
<220> FEATURE:
<223> OTHER INFORMATION: primers

<400> SEQUENCE: 10
agggagaact aaagggaac c                                             21

<210> SEQ ID NO 11
<211> LENGTH: 20
<212> TYPE: DNA
<213> ORGANISM: Artificial Sequence
<220> FEATURE:
<223> OTHER INFORMATION: primers

<400> SEQUENCE: 11
agaatgctgt gctgtggatg                                              20

<210> SEQ ID NO 12
<211> LENGTH: 19
<212> TYPE: DNA
<213> ORGANISM: Artificial Sequence
<220> FEATURE:
<223> OTHER INFORMATION: primers

<400> SEQUENCE: 12
gtgcttctgg gtcctggtt                                               19

<210> SEQ ID NO 13
<211> LENGTH: 21
<212> TYPE: DNA
<213> ORGANISM: Artificial Sequence
<220> FEATURE:
<223> OTHER INFORMATION: primers
```

<400> SEQUENCE: 13
tgaggtcagc tgagtctgtg g                                      21

<210> SEQ ID NO 14
<211> LENGTH: 20
<212> TYPE: DNA
<213> ORGANISM: Artificial Sequence
<220> FEATURE:
<223> OTHER INFORMATION: primers

<400> SEQUENCE: 14
ggattttcag ggctccgagt                                        20

<210> SEQ ID NO 15
<211> LENGTH: 18
<212> TYPE: DNA
<213> ORGANISM: Artificial Sequence
<220> FEATURE:
<223> OTHER INFORMATION: primers

<400> SEQUENCE: 15
gtgtctggcc cacctttg                                          18

<210> SEQ ID NO 16
<211> LENGTH: 20
<212> TYPE: DNA
<213> ORGANISM: Artificial Sequence
<220> FEATURE:
<223> OTHER INFORMATION: primers

<400> SEQUENCE: 16
attcttggtc catcctgtgg                                        20

<210> SEQ ID NO 17
<211> LENGTH: 21
<212> TYPE: DNA
<213> ORGANISM: Artificial Sequence
<220> FEATURE:
<223> OTHER INFORMATION: primers

<400> SEQUENCE: 17
ctccttttcc aactgggatt c                                      21

<210> SEQ ID NO 18
<211> LENGTH: 19
<212> TYPE: DNA
<213> ORGANISM: Artificial Sequence
<220> FEATURE:
<223> OTHER INFORMATION: primers

<400> SEQUENCE: 18
ctgcctcgtg aggttcaga                                         19

<210> SEQ ID NO 19
<211> LENGTH: 20
<212> TYPE: DNA
<213> ORGANISM: Artificial Sequence
<220> FEATURE:
<223> OTHER INFORMATION: primers

<400> SEQUENCE: 19
tgtatcaatg ggcagcagtg                                        20

<210> SEQ ID NO 20

```
<211> LENGTH: 20
<212> TYPE: DNA
<213> ORGANISM: Artificial Sequence
<220> FEATURE:
<223> OTHER INFORMATION: primers

<400> SEQUENCE: 20
tatgtcattc tgcccccaag                                                   20

<210> SEQ ID NO 21
<211> LENGTH: 20
<212> TYPE: DNA
<213> ORGANISM: Artificial Sequence
<220> FEATURE:
<223> OTHER INFORMATION: primers

<400> SEQUENCE: 21
ccgatggatg tatgcagtga                                                   20

<210> SEQ ID NO 22
<211> LENGTH: 21
<212> TYPE: DNA
<213> ORGANISM: Artificial Sequence
<220> FEATURE:
<223> OTHER INFORMATION: primers

<400> SEQUENCE: 22
ttgtttgctt gcttgaaacc t                                                 21

<210> SEQ ID NO 23
<211> LENGTH: 20
<212> TYPE: DNA
<213> ORGANISM: Artificial Sequence
<220> FEATURE:
<223> OTHER INFORMATION: primers

<400> SEQUENCE: 23
tctacttggg tgggggtgat                                                   20

<210> SEQ ID NO 24
<211> LENGTH: 20
<212> TYPE: DNA
<213> ORGANISM: Artificial Sequence
<220> FEATURE:
<223> OTHER INFORMATION: primers

<400> SEQUENCE: 24
ctccaagacg cgttagaacc                                                   20

<210> SEQ ID NO 25
<211> LENGTH: 21
<212> TYPE: DNA
<213> ORGANISM: Artificial Sequence
<220> FEATURE:
<223> OTHER INFORMATION: primers

<400> SEQUENCE: 25
aacacaagaa gcgaggagct t                                                 21

<210> SEQ ID NO 26
<211> LENGTH: 20
<212> TYPE: DNA
<213> ORGANISM: Artificial Sequence
<220> FEATURE:
<223> OTHER INFORMATION: primers

<400> SEQUENCE: 26
```
aagatcagca ggccaaagaa                                                        20

<210> SEQ ID NO 27
<211> LENGTH: 20
<212> TYPE: DNA
<213> ORGANISM: Artificial Sequence
<220> FEATURE:
<223> OTHER INFORMATION: primers

<400> SEQUENCE: 27
tgctgtggct ttgtgtcttc                                                        20

<210> SEQ ID NO 28
<211> LENGTH: 20
<212> TYPE: DNA
<213> ORGANISM: Artificial Sequence
<220> FEATURE:
<223> OTHER INFORMATION: primers

<400> SEQUENCE: 28
gtgtttgttc tggcccactc                                                        20

<210> SEQ ID NO 29
<211> LENGTH: 25
<212> TYPE: DNA
<213> ORGANISM: Artificial Sequence
<220> FEATURE:
<223> OTHER INFORMATION: primers

<400> SEQUENCE: 29
tcgtcttctt agaggatgca gtatt                                                  25

<210> SEQ ID NO 30
<211> LENGTH: 21
<212> TYPE: DNA
<213> ORGANISM: Artificial Sequence
<220> FEATURE:
<223> OTHER INFORMATION: primers

<400> SEQUENCE: 30
tgcctcacta tcaccgatct c                                                      21

<210> SEQ ID NO 31
<211> LENGTH: 22
<212> TYPE: DNA
<213> ORGANISM: Artificial Sequence
<220> FEATURE:
<223> OTHER INFORMATION: primers

<400> SEQUENCE: 31
ccgttgagat tcattctctc ct                                                     22

<210> SEQ ID NO 32
<211> LENGTH: 23
<212> TYPE: DNA
<213> ORGANISM: Artificial Sequence
<220> FEATURE:
<223> OTHER INFORMATION: primers

<400> SEQUENCE: 32
ttgtttaaaa tttccctgct cct                                                    23

<210> SEQ ID NO 33
<211> LENGTH: 27
<212> TYPE: DNA

```
<213> ORGANISM: Artificial Sequence
<220> FEATURE:
<223> OTHER INFORMATION: primers

<400> SEQUENCE: 33
tggattgatt aaacagatgt taaggtt                                              27

<210> SEQ ID NO 34
<211> LENGTH: 20
<212> TYPE: DNA
<213> ORGANISM: Artificial Sequence
<220> FEATURE:
<223> OTHER INFORMATION: primers

<400> SEQUENCE: 34
cagaagggcc gtttacactc                                                      20

<210> SEQ ID NO 35
<211> LENGTH: 22
<212> TYPE: DNA
<213> ORGANISM: Artificial Sequence
<220> FEATURE:
<223> OTHER INFORMATION: primers

<400> SEQUENCE: 35
agcatgtctg agcctctttt tc                                                   22

<210> SEQ ID NO 36
<211> LENGTH: 20
<212> TYPE: DNA
<213> ORGANISM: Artificial Sequence
<220> FEATURE:
<223> OTHER INFORMATION: primers

<400> SEQUENCE: 36
cagcaaagca gcaacaaaag                                                      20

<210> SEQ ID NO 37
<211> LENGTH: 20
<212> TYPE: DNA
<213> ORGANISM: Artificial Sequence
<220> FEATURE:
<223> OTHER INFORMATION: primers

<400> SEQUENCE: 37
cactctctcc accacaagca                                                      20

<210> SEQ ID NO 38
<211> LENGTH: 21
<212> TYPE: DNA
<213> ORGANISM: Artificial Sequence
<220> FEATURE:
<223> OTHER INFORMATION: primers

<400> SEQUENCE: 38
ttggccacca tcagtaagaa c                                                    21

<210> SEQ ID NO 39
<211> LENGTH: 20
<212> TYPE: DNA
<213> ORGANISM: Artificial Sequence
<220> FEATURE:
<223> OTHER INFORMATION: primers

<400> SEQUENCE: 39
agaatgggcc tctttggact                                                      20
```

```
<210> SEQ ID NO 40
<211> LENGTH: 20
<212> TYPE: DNA
<213> ORGANISM: Artificial Sequence
<220> FEATURE:
<223> OTHER INFORMATION: primers

<400> SEQUENCE: 40
cagggagctg ttttcaggtg                                              20

<210> SEQ ID NO 41
<211> LENGTH: 19
<212> TYPE: DNA
<213> ORGANISM: Artificial Sequence
<220> FEATURE:
<223> OTHER INFORMATION: primers

<400> SEQUENCE: 41
acactgtggg gagggaaaa                                               19

<210> SEQ ID NO 42
<211> LENGTH: 19
<212> TYPE: DNA
<213> ORGANISM: Artificial Sequence
<220> FEATURE:
<223> OTHER INFORMATION: primers

<400> SEQUENCE: 42
agcatttctg gcctcctgt                                               19

<210> SEQ ID NO 43
<211> LENGTH: 20
<212> TYPE: DNA
<213> ORGANISM: Artificial Sequence
<220> FEATURE:
<223> OTHER INFORMATION: primers

<400> SEQUENCE: 43
gccatctagt ctgcgaaagg                                              20

<210> SEQ ID NO 44
<211> LENGTH: 25
<212> TYPE: DNA
<213> ORGANISM: Artificial Sequence
<220> FEATURE:
<223> OTHER INFORMATION: primers

<400> SEQUENCE: 44
gtgggagaaa gtcagtttga ataaa                                        25

<210> SEQ ID NO 45
<211> LENGTH: 20
<212> TYPE: DNA
<213> ORGANISM: Artificial Sequence
<220> FEATURE:
<223> OTHER INFORMATION: primers

<400> SEQUENCE: 45
ctccatcgcc ctagactgaa                                              20

<210> SEQ ID NO 46
<211> LENGTH: 19
<212> TYPE: DNA
<213> ORGANISM: Artificial Sequence
<220> FEATURE:
```

```
<223> OTHER INFORMATION: primers

<400> SEQUENCE: 46
ctgctgcagg agtccacac                                                19

<210> SEQ ID NO 47
<211> LENGTH: 20
<212> TYPE: DNA
<213> ORGANISM: Artificial Sequence
<220> FEATURE:
<223> OTHER INFORMATION: primers

<400> SEQUENCE: 47
cctcatcatc tggcacctct                                               20

<210> SEQ ID NO 48
<211> LENGTH: 23
<212> TYPE: DNA
<213> ORGANISM: Artificial Sequence
<220> FEATURE:
<223> OTHER INFORMATION: primers

<400> SEQUENCE: 48
agtgacctca cacattgagg agt                                           23

<210> SEQ ID NO 49
<211> LENGTH: 21
<212> TYPE: DNA
<213> ORGANISM: Artificial Sequence
<220> FEATURE:
<223> OTHER INFORMATION: primers

<400> SEQUENCE: 49
tcatttgtgt gggtttgtgt g                                             21

<210> SEQ ID NO 50
<211> LENGTH: 19
<212> TYPE: DNA
<213> ORGANISM: Artificial Sequence
<220> FEATURE:
<223> OTHER INFORMATION: primers

<400> SEQUENCE: 50
ctccttatgc ctccccctga                                               19

<210> SEQ ID NO 51
<211> LENGTH: 19
<212> TYPE: DNA
<213> ORGANISM: Artificial Sequence
<220> FEATURE:
<223> OTHER INFORMATION: primers

<400> SEQUENCE: 51
gggagctgac ccaatccag                                                19

<210> SEQ ID NO 52
<211> LENGTH: 20
<212> TYPE: DNA
<213> ORGANISM: Artificial Sequence
<220> FEATURE:
<223> OTHER INFORMATION: primers

<400> SEQUENCE: 52
cctgaaggtt gcccataaaa                                               20
```

```
<210> SEQ ID NO 53
<211> LENGTH: 20
<212> TYPE: DNA
<213> ORGANISM: Artificial Sequence
<220> FEATURE:
<223> OTHER INFORMATION: primers

<400> SEQUENCE: 53
cccaggtctt ccaaacacag                                        20

<210> SEQ ID NO 54
<211> LENGTH: 20
<212> TYPE: DNA
<213> ORGANISM: Artificial Sequence
<220> FEATURE:
<223> OTHER INFORMATION: primers

<400> SEQUENCE: 54
actggaagct gccacttgag                                        20

<210> SEQ ID NO 55
<211> LENGTH: 20
<212> TYPE: DNA
<213> ORGANISM: Artificial Sequence
<220> FEATURE:
<223> OTHER INFORMATION: primers

<400> SEQUENCE: 55
ccacatttca gagcccagag                                        20

<210> SEQ ID NO 56
<211> LENGTH: 20
<212> TYPE: DNA
<213> ORGANISM: Artificial Sequence
<220> FEATURE:
<223> OTHER INFORMATION: primers

<400> SEQUENCE: 56
gccaaggcta cacatggttt                                        20

<210> SEQ ID NO 57
<211> LENGTH: 27
<212> TYPE: DNA
<213> ORGANISM: Artificial Sequence
<220> FEATURE:
<223> OTHER INFORMATION: primers

<400> SEQUENCE: 57
ttttaactac tcatacatcc ccatgtc                                27

<210> SEQ ID NO 58
<211> LENGTH: 20
<212> TYPE: DNA
<213> ORGANISM: Artificial Sequence
<220> FEATURE:
<223> OTHER INFORMATION: primers

<400> SEQUENCE: 58
ccctcttcca tcccgtattt                                        20

<210> SEQ ID NO 59
<211> LENGTH: 20
<212> TYPE: DNA
<213> ORGANISM: Artificial Sequence
<220> FEATURE:
<223> OTHER INFORMATION: primers
```

<400> SEQUENCE: 59
ccaagccaat tttccaaaga                                                  20

<210> SEQ ID NO 60
<211> LENGTH: 20
<212> TYPE: DNA
<213> ORGANISM: Artificial Sequence
<220> FEATURE:
<223> OTHER INFORMATION: primers

<400> SEQUENCE: 60
gcatcctcag gctgtttgac                                                  20

<210> SEQ ID NO 61
<211> LENGTH: 21
<212> TYPE: DNA
<213> ORGANISM: Artificial Sequence
<220> FEATURE:
<223> OTHER INFORMATION: primers

<400> SEQUENCE: 61
gggatgtgca ctgaaactga t                                                21

<210> SEQ ID NO 62
<211> LENGTH: 21
<212> TYPE: DNA
<213> ORGANISM: Artificial Sequence
<220> FEATURE:
<223> OTHER INFORMATION: primers

<400> SEQUENCE: 62
tcaactcagc tcaaggattg c                                                21

<210> SEQ ID NO 63
<211> LENGTH: 20
<212> TYPE: DNA
<213> ORGANISM: Artificial Sequence
<220> FEATURE:
<223> OTHER INFORMATION: primers

<400> SEQUENCE: 63
tgggggacaa acttttaggg                                                  20

<210> SEQ ID NO 64
<211> LENGTH: 21
<212> TYPE: DNA
<213> ORGANISM: Artificial Sequence
<220> FEATURE:
<223> OTHER INFORMATION: primers

<400> SEQUENCE: 64
ggctaggagt tgccttcaat c                                                21

<210> SEQ ID NO 65
<211> LENGTH: 21
<212> TYPE: DNA
<213> ORGANISM: Artificial Sequence
<220> FEATURE:
<223> OTHER INFORMATION: primers

<400> SEQUENCE: 65
ctcttcaccc ctgactcact g                                                21

<210> SEQ ID NO 66
<211> LENGTH: 23

<212> TYPE: DNA
<213> ORGANISM: Artificial Sequence
<220> FEATURE:
<223> OTHER INFORMATION: primers

<400> SEQUENCE: 66
acacaaaggg atacacacac aca                                   23

<210> SEQ ID NO 67
<211> LENGTH: 21
<212> TYPE: DNA
<213> ORGANISM: Artificial Sequence
<220> FEATURE:
<223> OTHER INFORMATION: primers

<400> SEQUENCE: 67
tctggaagat gtggtgttgg t                                     21

<210> SEQ ID NO 68
<211> LENGTH: 24
<212> TYPE: DNA
<213> ORGANISM: Artificial Sequence
<220> FEATURE:
<223> OTHER INFORMATION: primers

<400> SEQUENCE: 68
gacatgtctg ggcataatta aaca                                  24

<210> SEQ ID NO 69
<211> LENGTH: 20
<212> TYPE: DNA
<213> ORGANISM: Artificial Sequence
<220> FEATURE:
<223> OTHER INFORMATION: primers

<400> SEQUENCE: 69
gtccaagaac aggccagatg                                       20

<210> SEQ ID NO 70
<211> LENGTH: 20
<212> TYPE: DNA
<213> ORGANISM: Artificial Sequence
<220> FEATURE:
<223> OTHER INFORMATION: primers

<400> SEQUENCE: 70
ggagaaaagc caagtcagca                                       20

<210> SEQ ID NO 71
<211> LENGTH: 20
<212> TYPE: DNA
<213> ORGANISM: Artificial Sequence
<220> FEATURE:
<223> OTHER INFORMATION: primers

<400> SEQUENCE: 71
tgcctctgct gtcactgttc                                       20

<210> SEQ ID NO 72
<211> LENGTH: 20
<212> TYPE: DNA
<213> ORGANISM: Artificial Sequence
<220> FEATURE:
<223> OTHER INFORMATION: primers

<400> SEQUENCE: 72
cctcactccc ttcctccaac                                          20

<210> SEQ ID NO 73
<211> LENGTH: 20
<212> TYPE: DNA
<213> ORGANISM: Artificial Sequence
<220> FEATURE:
<223> OTHER INFORMATION: primers

<400> SEQUENCE: 73
tctgggaagc aagtgtgatg                                          20

<210> SEQ ID NO 74
<211> LENGTH: 20
<212> TYPE: DNA
<213> ORGANISM: Artificial Sequence
<220> FEATURE:
<223> OTHER INFORMATION: primers

<400> SEQUENCE: 74
aacccatggc cctacttgag                                          20

<210> SEQ ID NO 75
<211> LENGTH: 20
<212> TYPE: DNA
<213> ORGANISM: Artificial Sequence
<220> FEATURE:
<223> OTHER INFORMATION: primers

<400> SEQUENCE: 75
ggagagggtg attggtgaga                                          20

<210> SEQ ID NO 76
<211> LENGTH: 22
<212> TYPE: DNA
<213> ORGANISM: Artificial Sequence
<220> FEATURE:
<223> OTHER INFORMATION: primers

<400> SEQUENCE: 76
gggaaaaaca gtaaaagcag ca                                       22

<210> SEQ ID NO 77
<211> LENGTH: 20
<212> TYPE: DNA
<213> ORGANISM: Artificial Sequence
<220> FEATURE:
<223> OTHER INFORMATION: primers

<400> SEQUENCE: 77
caggcttctc tctccaggtg                                          20

<210> SEQ ID NO 78
<211> LENGTH: 19
<212> TYPE: DNA
<213> ORGANISM: Artificial Sequence
<220> FEATURE:
<223> OTHER INFORMATION: primers

<400> SEQUENCE: 78
ccgggcagct acttagagg                                           19

<210> SEQ ID NO 79
<211> LENGTH: 19
<212> TYPE: DNA
<213> ORGANISM: Artificial Sequence

```
<220> FEATURE:
<223> OTHER INFORMATION: primers

<400> SEQUENCE: 79
ttcctcgtgc gagagagtg                                                  19

<210> SEQ ID NO 80
<211> LENGTH: 22
<212> TYPE: DNA
<213> ORGANISM: Artificial Sequence
<220> FEATURE:
<223> OTHER INFORMATION: primers

<400> SEQUENCE: 80
ctctgggtga tgtgatgtct gt                                              22

<210> SEQ ID NO 81
<211> LENGTH: 20
<212> TYPE: DNA
<213> ORGANISM: Artificial Sequence
<220> FEATURE:
<223> OTHER INFORMATION: primers

<400> SEQUENCE: 81
gaggctggga actcagtgac                                                 20

<210> SEQ ID NO 82
<211> LENGTH: 23
<212> TYPE: DNA
<213> ORGANISM: Artificial Sequence
<220> FEATURE:
<223> OTHER INFORMATION: primers

<400> SEQUENCE: 82
ttttgttcct cagtttctct gga                                             23

<210> SEQ ID NO 83
<211> LENGTH: 24
<212> TYPE: DNA
<213> ORGANISM: Artificial Sequence
<220> FEATURE:
<223> OTHER INFORMATION: primers

<400> SEQUENCE: 83
tgttgagaat gcactttctt gaat                                            24

<210> SEQ ID NO 84
<211> LENGTH: 24
<212> TYPE: DNA
<213> ORGANISM: Artificial Sequence
<220> FEATURE:
<223> OTHER INFORMATION: primers

<400> SEQUENCE: 84
taagtggcta attttgggta atgg                                            24

<210> SEQ ID NO 85
<211> LENGTH: 20
<212> TYPE: DNA
<213> ORGANISM: Artificial Sequence
<220> FEATURE:
<223> OTHER INFORMATION: primers

<400> SEQUENCE: 85
attggaatgg gctacacctg                                                 20
```

```
<210> SEQ ID NO 86
<211> LENGTH: 20
<212> TYPE: DNA
<213> ORGANISM: Artificial Sequence
<220> FEATURE:
<223> OTHER INFORMATION: primers

<400> SEQUENCE: 86
cccacccaaa gcctaaagat                                                   20

<210> SEQ ID NO 87
<211> LENGTH: 20
<212> TYPE: DNA
<213> ORGANISM: Artificial Sequence
<220> FEATURE:
<223> OTHER INFORMATION: primers

<400> SEQUENCE: 87
ggtctttggt ccaggaaagc                                                   20

<210> SEQ ID NO 88
<211> LENGTH: 18
<212> TYPE: DNA
<213> ORGANISM: Artificial Sequence
<220> FEATURE:
<223> OTHER INFORMATION: primers

<400> SEQUENCE: 88
ggacaggtga gcccaggt                                                     18

<210> SEQ ID NO 89
<211> LENGTH: 20
<212> TYPE: DNA
<213> ORGANISM: Artificial Sequence
<220> FEATURE:
<223> OTHER INFORMATION: primers

<400> SEQUENCE: 89
ggtctttcca gggagtggag                                                   20

<210> SEQ ID NO 90
<211> LENGTH: 19
<212> TYPE: DNA
<213> ORGANISM: Artificial Sequence
<220> FEATURE:
<223> OTHER INFORMATION: primers

<400> SEQUENCE: 90
ctcagtcact tggcgcttc                                                    19

<210> SEQ ID NO 91
<211> LENGTH: 20
<212> TYPE: DNA
<213> ORGANISM: Artificial Sequence
<220> FEATURE:
<223> OTHER INFORMATION: primers

<400> SEQUENCE: 91
tggagctgcc ttggagtaac                                                   20

<210> SEQ ID NO 92
<211> LENGTH: 18
<212> TYPE: DNA
<213> ORGANISM: Artificial Sequence
<220> FEATURE:
<223> OTHER INFORMATION: primers
```

<400> SEQUENCE: 92
cagcccaggc actcacag                                                18

<210> SEQ ID NO 93
<211> LENGTH: 22
<212> TYPE: DNA
<213> ORGANISM: Artificial Sequence
<220> FEATURE:
<223> OTHER INFORMATION: primers

<400> SEQUENCE: 93
gattggagct cgactcagaa at                                           22

<210> SEQ ID NO 94
<211> LENGTH: 20
<212> TYPE: DNA
<213> ORGANISM: Artificial Sequence
<220> FEATURE:
<223> OTHER INFORMATION: primers

<400> SEQUENCE: 94
caggctgagg acttgaggag                                              20

<210> SEQ ID NO 95
<211> LENGTH: 16
<212> TYPE: PRT
<213> ORGANISM: Homo sapiens

<400> SEQUENCE: 95

Phe His Val Gly Tyr Phe Arg Ala Val Ile Gly Thr Leu Gln Met Ile
1               5                   10                  15

<210> SEQ ID NO 96
<211> LENGTH: 16
<212> TYPE: PRT
<213> ORGANISM: Homo sapiens

<400> SEQUENCE: 96

Phe His Val Gly Tyr Phe Arg Ala Val Ile Gly Ile Leu Gln Met Ile
1               5                   10                  15

<210> SEQ ID NO 97
<211> LENGTH: 10
<212> TYPE: PRT
<213> ORGANISM: Homo sapiens

<400> SEQUENCE: 97

Pro Asn Glu Leu Gly Gln Gly Ser Ala Phe
1               5                   10

<210> SEQ ID NO 98
<211> LENGTH: 8
<212> TYPE: PRT
<213> ORGANISM: Homo sapiens

<400> SEQUENCE: 98

Asp Glu Val Asn Thr Glu Ala Phe
1               5

<210> SEQ ID NO 99
<211> LENGTH: 10
<212> TYPE: PRT
<213> ORGANISM: Homo sapiens

```
<400> SEQUENCE: 99

Thr Gly Thr Val Met Asn Thr Glu Ala Phe
1               5                   10

<210> SEQ ID NO 100
<211> LENGTH: 9
<212> TYPE: PRT
<213> ORGANISM: Homo sapiens

<400> SEQUENCE: 100

Glu Ser Trp Thr Asp Tyr Gly Tyr Thr
1               5

<210> SEQ ID NO 101
<211> LENGTH: 9
<212> TYPE: PRT
<213> ORGANISM: Homo sapiens

<400> SEQUENCE: 101

Asp Gly Gly Thr Arg His Glu Gln Phe
1               5

<210> SEQ ID NO 102
<211> LENGTH: 9
<212> TYPE: PRT
<213> ORGANISM: Homo sapiens

<400> SEQUENCE: 102

Arg Asp Thr Val Asn Gln Pro Gln His
1               5

<210> SEQ ID NO 103
<211> LENGTH: 10
<212> TYPE: PRT
<213> ORGANISM: Homo sapiens

<400> SEQUENCE: 103

Thr Leu Gly Val Pro Arg Ile Lys Glu Ile
1               5                   10

<210> SEQ ID NO 104
<211> LENGTH: 10
<212> TYPE: PRT
<213> ORGANISM: Homo sapiens

<400> SEQUENCE: 104

Arg Ile Lys Glu Ile Ile Asn Ala Ser Lys
1               5                   10

<210> SEQ ID NO 105
<211> LENGTH: 11
<212> TYPE: PRT
<213> ORGANISM: Homo sapiens

<400> SEQUENCE: 105

Val Pro Arg Ile Lys Glu Ile Ile Asn Ala Ser
1               5                   10

<210> SEQ ID NO 106
<211> LENGTH: 8
<212> TYPE: PRT
<213> ORGANISM: Homo sapiens

<400> SEQUENCE: 106
```

```
Val Pro Arg Ile Lys Glu Ile Ile
1               5

<210> SEQ ID NO 107
<211> LENGTH: 11
<212> TYPE: PRT
<213> ORGANISM: Homo sapiens

<400> SEQUENCE: 107

Ile Thr Leu Gly Val Pro Arg Ile Lys Glu Ile
1               5                   10

<210> SEQ ID NO 108
<211> LENGTH: 14
<212> TYPE: PRT
<213> ORGANISM: Homo sapiens

<400> SEQUENCE: 108

Ser Met Asn Ile Thr Leu Gly Val Pro Arg Ile Lys Glu Ile
1               5                   10

<210> SEQ ID NO 109
<211> LENGTH: 17
<212> TYPE: PRT
<213> ORGANISM: Homo sapiens

<400> SEQUENCE: 109

Gly Val Pro Arg Ile Lys Glu Ile Ile Asn Ala Ser Lys Ala Ile Ser
1               5                   10                  15

Thr

<210> SEQ ID NO 110
<211> LENGTH: 17
<212> TYPE: PRT
<213> ORGANISM: Homo sapiens

<400> SEQUENCE: 110

Gly Val Pro Arg Ile Lys Glu Ile Ile Asn Ala Ser Lys Ala Ile Ser
1               5                   10                  15

Thr

<210> SEQ ID NO 111
<211> LENGTH: 9
<212> TYPE: PRT
<213> ORGANISM: Homo sapiens

<400> SEQUENCE: 111

Gly Leu Phe Lys Leu Leu His Lys Ala
1               5

<210> SEQ ID NO 112
<211> LENGTH: 10
<212> TYPE: PRT
<213> ORGANISM: Homo sapiens

<400> SEQUENCE: 112

Gly Thr Gly Leu Phe Lys Leu Leu His Lys
1               5                   10

<210> SEQ ID NO 113
<211> LENGTH: 8
<212> TYPE: PRT
<213> ORGANISM: Homo sapiens
```

```
<400> SEQUENCE: 113

Phe Lys Leu Leu His Lys Ala Asp
1               5

<210> SEQ ID NO 114
<211> LENGTH: 10
<212> TYPE: PRT
<213> ORGANISM: Homo sapiens

<400> SEQUENCE: 114

Thr Gly Leu Phe Lys Leu Leu His Lys Ala
1               5                   10

<210> SEQ ID NO 115
<211> LENGTH: 13
<212> TYPE: PRT
<213> ORGANISM: Homo sapiens

<400> SEQUENCE: 115

Lys Ala Asp Arg Asp Pro Asn Pro Pro Lys Arg Pro Leu
1               5                   10

<210> SEQ ID NO 116
<211> LENGTH: 14
<212> TYPE: PRT
<213> ORGANISM: Homo sapiens

<400> SEQUENCE: 116

Lys Leu Leu His Lys Ala Asp Arg Asp Pro Asn Pro Pro Lys
1               5                   10

<210> SEQ ID NO 117
<211> LENGTH: 17
<212> TYPE: PRT
<213> ORGANISM: Homo sapiens

<400> SEQUENCE: 117

Ile Gly Thr Gly Leu Phe Lys Leu Leu His Lys Ala Asp Arg Asp Pro
1               5                   10                  15

Asn

<210> SEQ ID NO 118
<211> LENGTH: 17
<212> TYPE: PRT
<213> ORGANISM: Homo sapiens

<400> SEQUENCE: 118

Ile Gly Thr Gly Leu Phe Lys Leu Leu His Lys Ala Asp Arg Asp Pro
1               5                   10                  15

Asn

<210> SEQ ID NO 119
<211> LENGTH: 8
<212> TYPE: PRT
<213> ORGANISM: Homo sapiens

<400> SEQUENCE: 119

Val Ile Gly Ile Leu Gln Met Ile
1               5

<210> SEQ ID NO 120
<211> LENGTH: 11
<212> TYPE: PRT
```

```
<213> ORGANISM: Homo sapiens

<400> SEQUENCE: 120

Tyr Phe Arg Ala Val Ile Gly Ile Leu Gln Met
1               5                   10

<210> SEQ ID NO 121
<211> LENGTH: 8
<212> TYPE: PRT
<213> ORGANISM: Homo sapiens

<400> SEQUENCE: 121

Phe Arg Ala Val Ile Gly Ile Leu
1               5

<210> SEQ ID NO 122
<211> LENGTH: 8
<212> TYPE: PRT
<213> ORGANISM: Homo sapiens

<400> SEQUENCE: 122

Ala Val Ile Gly Ile Leu Gln Met
1               5

<210> SEQ ID NO 123
<211> LENGTH: 11
<212> TYPE: PRT
<213> ORGANISM: Homo sapiens

<400> SEQUENCE: 123

Phe Arg Ala Val Ile Gly Ile Leu Gln Met Ile
1               5                   10

<210> SEQ ID NO 124
<211> LENGTH: 11
<212> TYPE: PRT
<213> ORGANISM: Homo sapiens

<400> SEQUENCE: 124

Tyr Phe Arg Ala Val Ile Gly Ile Leu Gln Met
1               5                   10

<210> SEQ ID NO 125
<211> LENGTH: 16
<212> TYPE: PRT
<213> ORGANISM: Homo sapiens

<400> SEQUENCE: 125

Phe His Val Gly Tyr Phe Arg Ala Val Ile Gly Ile Leu Gln Met Ile
1               5                   10                  15

<210> SEQ ID NO 126
<211> LENGTH: 16
<212> TYPE: PRT
<213> ORGANISM: Homo sapiens

<400> SEQUENCE: 126

Phe His Val Gly Tyr Phe Arg Ala Val Ile Gly Ile Leu Gln Met Ile
1               5                   10                  15

<210> SEQ ID NO 127
<211> LENGTH: 10
<212> TYPE: PRT
<213> ORGANISM: Homo sapiens
```

```
<400> SEQUENCE: 127

Thr Leu Gly Val Pro Arg Ile Lys Gln Ile
1               5                   10

<210> SEQ ID NO 128
<211> LENGTH: 10
<212> TYPE: PRT
<213> ORGANISM: Homo sapiens

<400> SEQUENCE: 128

Arg Ile Lys Gln Ile Ile Asn Ala Ser Lys
1               5                   10

<210> SEQ ID NO 129
<211> LENGTH: 11
<212> TYPE: PRT
<213> ORGANISM: Homo sapiens

<400> SEQUENCE: 129

Val Pro Arg Ile Lys Gln Ile Ile Asn Ala Ser
1               5                   10

<210> SEQ ID NO 130
<211> LENGTH: 8
<212> TYPE: PRT
<213> ORGANISM: Homo sapiens

<400> SEQUENCE: 130

Val Pro Arg Ile Lys Gln Ile Ile
1               5

<210> SEQ ID NO 131
<211> LENGTH: 11
<212> TYPE: PRT
<213> ORGANISM: Homo sapiens

<400> SEQUENCE: 131

Ile Thr Leu Gly Val Pro Arg Ile Lys Gln Ile
1               5                   10

<210> SEQ ID NO 132
<211> LENGTH: 14
<212> TYPE: PRT
<213> ORGANISM: Homo sapiens

<400> SEQUENCE: 132

Ser Met Asn Ile Thr Leu Gly Val Pro Arg Ile Lys Gln Ile
1               5                   10

<210> SEQ ID NO 133
<211> LENGTH: 17
<212> TYPE: PRT
<213> ORGANISM: Homo sapiens

<400> SEQUENCE: 133

Gly Val Pro Arg Ile Lys Gln Ile Ile Asn Ala Ser Lys Ala Ile Ser
1               5                   10                  15

Thr

<210> SEQ ID NO 134
<211> LENGTH: 17
<212> TYPE: PRT
<213> ORGANISM: Homo sapiens
```

<400> SEQUENCE: 134

Gly Val Pro Arg Ile Lys Gln Ile Ile Asn Ala Ser Lys Ala Ile Ser
1               5                   10                  15

Thr

<210> SEQ ID NO 135
<211> LENGTH: 9
<212> TYPE: PRT
<213> ORGANISM: Homo sapiens

<400> SEQUENCE: 135

Gly Leu Phe Lys Leu Leu His Asn Ala
1               5

<210> SEQ ID NO 136
<211> LENGTH: 10
<212> TYPE: PRT
<213> ORGANISM: Homo sapiens

<400> SEQUENCE: 136

Gly Thr Gly Leu Phe Lys Leu Leu His Asn
1               5                   10

<210> SEQ ID NO 137
<211> LENGTH: 8
<212> TYPE: PRT
<213> ORGANISM: Homo sapiens

<400> SEQUENCE: 137

Phe Lys Leu Leu His Asn Ala Asp
1               5

<210> SEQ ID NO 138
<211> LENGTH: 10
<212> TYPE: PRT
<213> ORGANISM: Homo sapiens

<400> SEQUENCE: 138

Thr Gly Leu Phe Lys Leu Leu His Asn Ala
1               5                   10

<210> SEQ ID NO 139
<211> LENGTH: 13
<212> TYPE: PRT
<213> ORGANISM: Homo sapiens

<400> SEQUENCE: 139

Asn Ala Asp Arg Asp Pro Asn Pro Pro Lys Arg Pro Leu
1               5                   10

<210> SEQ ID NO 140
<211> LENGTH: 14
<212> TYPE: PRT
<213> ORGANISM: Homo sapiens

<400> SEQUENCE: 140

Lys Leu Leu His Asn Ala Asp Arg Asp Pro Asn Pro Pro Lys
1               5                   10

<210> SEQ ID NO 141
<211> LENGTH: 17
<212> TYPE: PRT
<213> ORGANISM: Homo sapiens

<400> SEQUENCE: 141

Ile Gly Thr Gly Leu Phe Lys Leu Leu His Asn Ala Asp Arg Asp Pro
1               5                   10                  15
Asn

<210> SEQ ID NO 142
<211> LENGTH: 17
<212> TYPE: PRT
<213> ORGANISM: Homo sapiens

<400> SEQUENCE: 142

Ile Gly Thr Gly Leu Phe Lys Leu Leu His Asn Ala Asp Arg Asp Pro
1               5                   10                  15
Asn

<210> SEQ ID NO 143
<211> LENGTH: 8
<212> TYPE: PRT
<213> ORGANISM: Homo sapiens

<400> SEQUENCE: 143

Val Ile Gly Thr Leu Gln Met Ile
1               5

<210> SEQ ID NO 144
<211> LENGTH: 11
<212> TYPE: PRT
<213> ORGANISM: Homo sapiens

<400> SEQUENCE: 144

Tyr Phe Arg Ala Val Ile Gly Thr Leu Gln Met
1               5                   10

<210> SEQ ID NO 145
<211> LENGTH: 8
<212> TYPE: PRT
<213> ORGANISM: Homo sapiens

<400> SEQUENCE: 145

Phe Arg Ala Val Ile Gly Thr Leu
1               5

<210> SEQ ID NO 146
<211> LENGTH: 8
<212> TYPE: PRT
<213> ORGANISM: Homo sapiens

<400> SEQUENCE: 146

Ala Val Ile Gly Thr Leu Gln Met
1               5

<210> SEQ ID NO 147
<211> LENGTH: 11
<212> TYPE: PRT
<213> ORGANISM: Homo sapiens

<400> SEQUENCE: 147

Phe Arg Ala Val Ile Gly Thr Leu Gln Met Ile
1               5                   10

<210> SEQ ID NO 148
<211> LENGTH: 11
<212> TYPE: PRT

<213> ORGANISM: Homo sapiens

<400> SEQUENCE: 148

Tyr Phe Arg Ala Val Ile Gly Thr Leu Gln Met
1               5                   10

<210> SEQ ID NO 149
<211> LENGTH: 16
<212> TYPE: PRT
<213> ORGANISM: Homo sapiens

<400> SEQUENCE: 149

Phe His Val Gly Tyr Phe Arg Ala Val Ile Gly Thr Leu Gln Met Ile
1               5                   10                  15

<210> SEQ ID NO 150
<211> LENGTH: 16
<212> TYPE: PRT
<213> ORGANISM: Homo sapiens

<400> SEQUENCE: 150

Phe His Val Gly Tyr Phe Arg Ala Val Ile Gly Thr Leu Gln Met Ile
1               5                   10                  15

<210> SEQ ID NO 151
<211> LENGTH: 15
<212> TYPE: PRT
<213> ORGANISM: Homo sapiens

<400> SEQUENCE: 151

Met Val Lys Glu Gln Phe Arg Glu Thr Asp Val Ala Lys Lys Ile
1               5                   10                  15

<210> SEQ ID NO 152
<211> LENGTH: 15
<212> TYPE: PRT
<213> ORGANISM: Homo sapiens

<400> SEQUENCE: 152

Phe Arg Glu Thr Asp Val Ala Lys Lys Ile Ser His Ile Cys Phe
1               5                   10                  15

<210> SEQ ID NO 153
<211> LENGTH: 15
<212> TYPE: PRT
<213> ORGANISM: Homo sapiens

<400> SEQUENCE: 153

Val Ala Lys Lys Ile Ser His Ile Cys Phe Gly Met Lys Ser Pro
1               5                   10                  15

<210> SEQ ID NO 154
<211> LENGTH: 15
<212> TYPE: PRT
<213> ORGANISM: Homo sapiens

<400> SEQUENCE: 154

Ser His Ile Cys Phe Gly Met Lys Ser Pro Glu Glu Met Arg Gln
1               5                   10                  15

<210> SEQ ID NO 155
<211> LENGTH: 15
<212> TYPE: PRT
<213> ORGANISM: Homo sapiens

<400> SEQUENCE: 155

Gly Met Lys Ser Pro Glu Glu Met Arg Gln Gln Ala His Ile Gln
1               5                   10                  15

<210> SEQ ID NO 156
<211> LENGTH: 15
<212> TYPE: PRT
<213> ORGANISM: Homo sapiens

<400> SEQUENCE: 156

Glu Glu Met Arg Gln Gln Ala His Ile Gln Val Val Ser Lys Asn
1               5                   10                  15

<210> SEQ ID NO 157
<211> LENGTH: 15
<212> TYPE: PRT
<213> ORGANISM: Homo sapiens

<400> SEQUENCE: 157

Gln Ala His Ile Gln Val Val Ser Lys Asn Leu Tyr Ser Gln Asp
1               5                   10                  15

<210> SEQ ID NO 158
<211> LENGTH: 15
<212> TYPE: PRT
<213> ORGANISM: Homo sapiens

<400> SEQUENCE: 158

Val Val Ser Lys Asn Leu Tyr Ser Gln Asp Asn Gln His Ala Pro
1               5                   10                  15

<210> SEQ ID NO 159
<211> LENGTH: 15
<212> TYPE: PRT
<213> ORGANISM: Homo sapiens

<400> SEQUENCE: 159

Leu Tyr Ser Gln Asp Asn Gln His Ala Pro Leu Leu Tyr Gly Val
1               5                   10                  15

<210> SEQ ID NO 160
<211> LENGTH: 15
<212> TYPE: PRT
<213> ORGANISM: Homo sapiens

<400> SEQUENCE: 160

Asn Gln His Ala Pro Leu Leu Tyr Gly Val Leu Asp His Arg Met
1               5                   10                  15

<210> SEQ ID NO 161
<211> LENGTH: 15
<212> TYPE: PRT
<213> ORGANISM: Homo sapiens

<400> SEQUENCE: 161

Leu Leu Tyr Gly Val Leu Asp His Arg Met Gly Thr Ser Glu Lys
1               5                   10                  15

<210> SEQ ID NO 162
<211> LENGTH: 15
<212> TYPE: PRT
<213> ORGANISM: Homo sapiens

<400> SEQUENCE: 162

Leu Asp His Arg Met Gly Thr Ser Glu Lys Asp Arg Pro Cys Glu
1               5                   10                  15

<210> SEQ ID NO 163
<211> LENGTH: 15
<212> TYPE: PRT
<213> ORGANISM: Homo sapiens

<400> SEQUENCE: 163

Gly Thr Ser Glu Lys Asp Arg Pro Cys Glu Thr Cys Gly Lys Asn
1               5                   10                  15

<210> SEQ ID NO 164
<211> LENGTH: 15
<212> TYPE: PRT
<213> ORGANISM: Homo sapiens

<400> SEQUENCE: 164

Asp Arg Pro Cys Glu Thr Cys Gly Lys Asn Leu Ala Asp Cys Leu
1               5                   10                  15

<210> SEQ ID NO 165
<211> LENGTH: 15
<212> TYPE: PRT
<213> ORGANISM: Homo sapiens

<400> SEQUENCE: 165

Thr Cys Gly Lys Asn Leu Ala Asp Cys Leu Gly His Tyr Gly Tyr
1               5                   10                  15

<210> SEQ ID NO 166
<211> LENGTH: 15
<212> TYPE: PRT
<213> ORGANISM: Homo sapiens

<400> SEQUENCE: 166

Leu Ala Asp Cys Leu Gly His Tyr Gly Tyr Ile Asp Leu Glu Leu
1               5                   10                  15

<210> SEQ ID NO 167
<211> LENGTH: 15
<212> TYPE: PRT
<213> ORGANISM: Homo sapiens

<400> SEQUENCE: 167

Gly His Tyr Gly Tyr Ile Asp Leu Glu Leu Pro Cys Phe His Val
1               5                   10                  15

<210> SEQ ID NO 168
<211> LENGTH: 15
<212> TYPE: PRT
<213> ORGANISM: Homo sapiens

<400> SEQUENCE: 168

Ile Asp Leu Glu Leu Pro Cys Phe His Val Gly Tyr Phe Arg Ala
1               5                   10                  15

<210> SEQ ID NO 169
<211> LENGTH: 15
<212> TYPE: PRT
<213> ORGANISM: Homo sapiens

<400> SEQUENCE: 169

Pro Cys Phe His Val Gly Tyr Phe Arg Ala Val Ile Gly Ile Leu
1               5                   10                  15

<210> SEQ ID NO 170
<211> LENGTH: 15
<212> TYPE: PRT
<213> ORGANISM: Homo sapiens

<400> SEQUENCE: 170

Gly Tyr Phe Arg Ala Val Ile Gly Ile Leu Gln Met Ile Cys Lys
1               5                   10                  15

<210> SEQ ID NO 171
<211> LENGTH: 15
<212> TYPE: PRT
<213> ORGANISM: Homo sapiens

<400> SEQUENCE: 171

Val Ile Gly Ile Leu Gln Met Ile Cys Lys Thr Cys Cys His Ile
1               5                   10                  15

<210> SEQ ID NO 172
<211> LENGTH: 15
<212> TYPE: PRT
<213> ORGANISM: Homo sapiens

<400> SEQUENCE: 172

Gln Met Ile Cys Lys Thr Cys Cys His Ile Met Leu Ser Gln Glu
1               5                   10                  15

<210> SEQ ID NO 173
<211> LENGTH: 15
<212> TYPE: PRT
<213> ORGANISM: Homo sapiens

<400> SEQUENCE: 173

Thr Cys Cys His Ile Met Leu Ser Gln Glu Glu Lys Lys Gln Phe
1               5                   10                  15

<210> SEQ ID NO 174
<211> LENGTH: 15
<212> TYPE: PRT
<213> ORGANISM: Homo sapiens

<400> SEQUENCE: 174

Met Leu Ser Gln Glu Glu Lys Lys Gln Phe Leu Asp Tyr Leu Lys
1               5                   10                  15

<210> SEQ ID NO 175
<211> LENGTH: 15
<212> TYPE: PRT
<213> ORGANISM: Homo sapiens

<400> SEQUENCE: 175

Glu Lys Lys Gln Phe Leu Asp Tyr Leu Lys Arg Pro Gly Leu Thr
1               5                   10                  15

<210> SEQ ID NO 176
<211> LENGTH: 15
<212> TYPE: PRT
<213> ORGANISM: Homo sapiens

<400> SEQUENCE: 176

Leu Asp Tyr Leu Lys Arg Pro Gly Leu Thr Tyr Leu Gln Lys Arg
1               5                   10                  15

```
<210> SEQ ID NO 177
<211> LENGTH: 15
<212> TYPE: PRT
<213> ORGANISM: Homo sapiens

<400> SEQUENCE: 177

Arg Pro Gly Leu Thr Tyr Leu Gln Lys Arg Gly Leu Lys Lys Lys
1               5                   10                  15

<210> SEQ ID NO 178
<211> LENGTH: 15
<212> TYPE: PRT
<213> ORGANISM: Homo sapiens

<400> SEQUENCE: 178

Tyr Leu Gln Lys Arg Gly Leu Lys Lys Lys Ile Ser Asp Lys Cys
1               5                   10                  15

<210> SEQ ID NO 179
<211> LENGTH: 15
<212> TYPE: PRT
<213> ORGANISM: Homo sapiens

<400> SEQUENCE: 179

Gly Leu Lys Lys Lys Ile Ser Asp Lys Cys Arg Lys Lys Asn Ile
1               5                   10                  15

<210> SEQ ID NO 180
<211> LENGTH: 15
<212> TYPE: PRT
<213> ORGANISM: Homo sapiens

<400> SEQUENCE: 180

Ile Ser Asp Lys Cys Arg Lys Lys Asn Ile Cys His His Cys Gly
1               5                   10                  15

<210> SEQ ID NO 181
<211> LENGTH: 15
<212> TYPE: PRT
<213> ORGANISM: Homo sapiens

<400> SEQUENCE: 181

Arg Lys Lys Asn Ile Cys His His Cys Gly Ala Phe Asn Gly Thr
1               5                   10                  15

<210> SEQ ID NO 182
<211> LENGTH: 15
<212> TYPE: PRT
<213> ORGANISM: Homo sapiens

<400> SEQUENCE: 182

Cys His His Cys Gly Ala Phe Asn Gly Thr Val Lys Lys Cys Gly
1               5                   10                  15

<210> SEQ ID NO 183
<211> LENGTH: 15
<212> TYPE: PRT
<213> ORGANISM: Homo sapiens

<400> SEQUENCE: 183

Ala Phe Asn Gly Thr Val Lys Lys Cys Gly Leu Leu Lys Ile Ile
1               5                   10                  15

<210> SEQ ID NO 184
<211> LENGTH: 15
```

```
<212> TYPE: PRT
<213> ORGANISM: Homo sapiens

<400> SEQUENCE: 184

Val Lys Lys Cys Gly Leu Leu Lys Ile Ile His Glu Lys Tyr Lys
1               5                   10                  15

<210> SEQ ID NO 185
<211> LENGTH: 15
<212> TYPE: PRT
<213> ORGANISM: Homo sapiens

<400> SEQUENCE: 185

Leu Leu Lys Ile Ile His Glu Lys Tyr Lys Thr Asn Lys Lys Val
1               5                   10                  15

<210> SEQ ID NO 186
<211> LENGTH: 15
<212> TYPE: PRT
<213> ORGANISM: Homo sapiens

<400> SEQUENCE: 186

His Glu Lys Tyr Lys Thr Asn Lys Lys Val Val Asp Pro Ile Val
1               5                   10                  15

<210> SEQ ID NO 187
<211> LENGTH: 15
<212> TYPE: PRT
<213> ORGANISM: Homo sapiens

<400> SEQUENCE: 187

Thr Asn Lys Lys Val Val Asp Pro Ile Val Ser Asn Phe Leu Gln
1               5                   10                  15

<210> SEQ ID NO 188
<211> LENGTH: 15
<212> TYPE: PRT
<213> ORGANISM: Homo sapiens

<400> SEQUENCE: 188

Val Asp Pro Ile Val Ser Asn Phe Leu Gln Ser Phe Glu Thr Ala
1               5                   10                  15

<210> SEQ ID NO 189
<211> LENGTH: 15
<212> TYPE: PRT
<213> ORGANISM: Homo sapiens

<400> SEQUENCE: 189

Ser Asn Phe Leu Gln Ser Phe Glu Thr Ala Ile Glu His Asn Lys
1               5                   10                  15

<210> SEQ ID NO 190
<211> LENGTH: 15
<212> TYPE: PRT
<213> ORGANISM: Homo sapiens

<400> SEQUENCE: 190

Ser Phe Glu Thr Ala Ile Glu His Asn Lys Glu Val Glu Pro Leu
1               5                   10                  15

<210> SEQ ID NO 191
<211> LENGTH: 15
<212> TYPE: PRT
<213> ORGANISM: Homo sapiens
```

<400> SEQUENCE: 191

Ile Glu His Asn Lys Glu Val Glu Pro Leu Leu Gly Arg Ala Gln
1               5                   10                  15

<210> SEQ ID NO 192
<211> LENGTH: 15
<212> TYPE: PRT
<213> ORGANISM: Homo sapiens

<400> SEQUENCE: 192

Glu Val Glu Pro Leu Leu Gly Arg Ala Gln Glu Asn Leu Asn Pro
1               5                   10                  15

<210> SEQ ID NO 193
<211> LENGTH: 15
<212> TYPE: PRT
<213> ORGANISM: Homo sapiens

<400> SEQUENCE: 193

Leu Gly Arg Ala Gln Glu Asn Leu Asn Pro Leu Val Val Leu Asn
1               5                   10                  15

<210> SEQ ID NO 194
<211> LENGTH: 15
<212> TYPE: PRT
<213> ORGANISM: Homo sapiens

<400> SEQUENCE: 194

Glu Asn Leu Asn Pro Leu Val Val Leu Asn Leu Phe Lys Arg Ile
1               5                   10                  15

<210> SEQ ID NO 195
<211> LENGTH: 15
<212> TYPE: PRT
<213> ORGANISM: Homo sapiens

<400> SEQUENCE: 195

Leu Val Val Leu Asn Leu Phe Lys Arg Ile Pro Ala Glu Asp Val
1               5                   10                  15

<210> SEQ ID NO 196
<211> LENGTH: 15
<212> TYPE: PRT
<213> ORGANISM: Homo sapiens

<400> SEQUENCE: 196

Leu Phe Lys Arg Ile Pro Ala Glu Asp Val Pro Leu Leu Leu Met
1               5                   10                  15

<210> SEQ ID NO 197
<211> LENGTH: 15
<212> TYPE: PRT
<213> ORGANISM: Homo sapiens

<400> SEQUENCE: 197

Pro Ala Glu Asp Val Pro Leu Leu Leu Met Asn Pro Glu Ala Gly
1               5                   10                  15

<210> SEQ ID NO 198
<211> LENGTH: 15
<212> TYPE: PRT
<213> ORGANISM: Homo sapiens

<400> SEQUENCE: 198

Pro Leu Leu Leu Met Asn Pro Glu Ala Gly Lys Pro Ser Asp Leu
1               5                   10                  15

<210> SEQ ID NO 199
<211> LENGTH: 15
<212> TYPE: PRT
<213> ORGANISM: Homo sapiens

<400> SEQUENCE: 199

Asn Pro Glu Ala Gly Lys Pro Ser Asp Leu Ile Leu Thr Arg Leu
1               5                   10                  15

<210> SEQ ID NO 200
<211> LENGTH: 15
<212> TYPE: PRT
<213> ORGANISM: Homo sapiens

<400> SEQUENCE: 200

Lys Pro Ser Asp Leu Ile Leu Thr Arg Leu Leu Val Pro Pro Leu
1               5                   10                  15

<210> SEQ ID NO 201
<211> LENGTH: 15
<212> TYPE: PRT
<213> ORGANISM: Homo sapiens

<400> SEQUENCE: 201

Ile Leu Thr Arg Leu Leu Val Pro Pro Leu Cys Ile Arg Pro Ser
1               5                   10                  15

<210> SEQ ID NO 202
<211> LENGTH: 15
<212> TYPE: PRT
<213> ORGANISM: Homo sapiens

<400> SEQUENCE: 202

Leu Val Pro Pro Leu Cys Ile Arg Pro Ser Val Val Ser Asp Leu
1               5                   10                  15

<210> SEQ ID NO 203
<211> LENGTH: 15
<212> TYPE: PRT
<213> ORGANISM: Homo sapiens

<400> SEQUENCE: 203

Cys Ile Arg Pro Ser Val Val Ser Asp Leu Lys Ser Gly Thr Asn
1               5                   10                  15

<210> SEQ ID NO 204
<211> LENGTH: 15
<212> TYPE: PRT
<213> ORGANISM: Homo sapiens

<400> SEQUENCE: 204

Val Val Ser Asp Leu Lys Ser Gly Thr Asn Glu Asp Asp Leu Thr
1               5                   10                  15

<210> SEQ ID NO 205
<211> LENGTH: 15
<212> TYPE: PRT
<213> ORGANISM: Homo sapiens

<400> SEQUENCE: 205

Lys Ser Gly Thr Asn Glu Asp Asp Leu Thr Met Lys Leu Thr Glu

<210> SEQ ID NO 206
<211> LENGTH: 15
<212> TYPE: PRT
<213> ORGANISM: Homo sapiens

<400> SEQUENCE: 206

Glu Asp Asp Leu Thr Met Lys Leu Thr Glu Ile Ile Phe Leu Asn
1               5                   10                  15

<210> SEQ ID NO 207
<211> LENGTH: 15
<212> TYPE: PRT
<213> ORGANISM: Homo sapiens

<400> SEQUENCE: 207

Met Lys Leu Thr Glu Ile Ile Phe Leu Asn Asp Val Ile Lys Lys
1               5                   10                  15

<210> SEQ ID NO 208
<211> LENGTH: 15
<212> TYPE: PRT
<213> ORGANISM: Homo sapiens

<400> SEQUENCE: 208

Ile Ile Phe Leu Asn Asp Val Ile Lys Lys His Arg Ile Ser Gly
1               5                   10                  15

<210> SEQ ID NO 209
<211> LENGTH: 15
<212> TYPE: PRT
<213> ORGANISM: Homo sapiens

<400> SEQUENCE: 209

Asp Val Ile Lys Lys His Arg Ile Ser Gly Ala Lys Thr Gln Met
1               5                   10                  15

<210> SEQ ID NO 210
<211> LENGTH: 15
<212> TYPE: PRT
<213> ORGANISM: Homo sapiens

<400> SEQUENCE: 210

His Arg Ile Ser Gly Ala Lys Thr Gln Met Ile Met Glu Asp Trp
1               5                   10                  15

<210> SEQ ID NO 211
<211> LENGTH: 15
<212> TYPE: PRT
<213> ORGANISM: Homo sapiens

<400> SEQUENCE: 211

Ala Lys Thr Gln Met Ile Met Glu Asp Trp Asp Phe Leu Gln Leu
1               5                   10                  15

<210> SEQ ID NO 212
<211> LENGTH: 15
<212> TYPE: PRT
<213> ORGANISM: Homo sapiens

<400> SEQUENCE: 212

Ile Met Glu Asp Trp Asp Phe Leu Gln Leu Gln Cys Ala Leu Tyr
1               5                   10                  15

<210> SEQ ID NO 213
<211> LENGTH: 15
<212> TYPE: PRT
<213> ORGANISM: Homo sapiens

<400> SEQUENCE: 213

Asp Phe Leu Gln Leu Gln Cys Ala Leu Tyr Ile Asn Ser Glu Leu
1               5                   10                  15

<210> SEQ ID NO 214
<211> LENGTH: 15
<212> TYPE: PRT
<213> ORGANISM: Homo sapiens

<400> SEQUENCE: 214

Gln Cys Ala Leu Tyr Ile Asn Ser Glu Leu Ser Gly Ile Pro Leu
1               5                   10                  15

<210> SEQ ID NO 215
<211> LENGTH: 15
<212> TYPE: PRT
<213> ORGANISM: Homo sapiens

<400> SEQUENCE: 215

Ile Asn Ser Glu Leu Ser Gly Ile Pro Leu Asn Met Ala Pro Lys
1               5                   10                  15

<210> SEQ ID NO 216
<211> LENGTH: 15
<212> TYPE: PRT
<213> ORGANISM: Homo sapiens

<400> SEQUENCE: 216

Ser Gly Ile Pro Leu Asn Met Ala Pro Lys Lys Trp Thr Arg Gly
1               5                   10                  15

<210> SEQ ID NO 217
<211> LENGTH: 15
<212> TYPE: PRT
<213> ORGANISM: Homo sapiens

<400> SEQUENCE: 217

Asn Met Ala Pro Lys Lys Trp Thr Arg Gly Phe Val Gln Arg Leu
1               5                   10                  15

<210> SEQ ID NO 218
<211> LENGTH: 15
<212> TYPE: PRT
<213> ORGANISM: Homo sapiens

<400> SEQUENCE: 218

Lys Trp Thr Arg Gly Phe Val Gln Arg Leu Lys Gly Lys Gln Gly
1               5                   10                  15

<210> SEQ ID NO 219
<211> LENGTH: 15
<212> TYPE: PRT
<213> ORGANISM: Homo sapiens

<400> SEQUENCE: 219

Phe Val Gln Arg Leu Lys Gly Lys Gln Gly Arg Phe Arg Gly Asn
1               5                   10                  15

<210> SEQ ID NO 220

-continued

```
<211> LENGTH: 15
<212> TYPE: PRT
<213> ORGANISM: Homo sapiens

<400> SEQUENCE: 220

Lys Gly Lys Gln Gly Arg Phe Arg Gly Asn Leu Ser Gly Lys Arg
1               5                   10                  15

<210> SEQ ID NO 221
<211> LENGTH: 15
<212> TYPE: PRT
<213> ORGANISM: Homo sapiens

<400> SEQUENCE: 221

Arg Phe Arg Gly Asn Leu Ser Gly Lys Arg Val Asp Phe Ser Gly
1               5                   10                  15

<210> SEQ ID NO 222
<211> LENGTH: 15
<212> TYPE: PRT
<213> ORGANISM: Homo sapiens

<400> SEQUENCE: 222

Leu Ser Gly Lys Arg Val Asp Phe Ser Gly Arg Thr Val Ile Ser
1               5                   10                  15

<210> SEQ ID NO 223
<211> LENGTH: 15
<212> TYPE: PRT
<213> ORGANISM: Homo sapiens

<400> SEQUENCE: 223

Val Asp Phe Ser Gly Arg Thr Val Ile Ser Pro Asp Pro Asn Leu
1               5                   10                  15

<210> SEQ ID NO 224
<211> LENGTH: 15
<212> TYPE: PRT
<213> ORGANISM: Homo sapiens

<400> SEQUENCE: 224

Arg Thr Val Ile Ser Pro Asp Pro Asn Leu Arg Ile Asp Glu Val
1               5                   10                  15

<210> SEQ ID NO 225
<211> LENGTH: 15
<212> TYPE: PRT
<213> ORGANISM: Homo sapiens

<400> SEQUENCE: 225

Pro Asp Pro Asn Leu Arg Ile Asp Glu Val Ala Val Pro Val His
1               5                   10                  15

<210> SEQ ID NO 226
<211> LENGTH: 15
<212> TYPE: PRT
<213> ORGANISM: Homo sapiens

<400> SEQUENCE: 226

Arg Ile Asp Glu Val Ala Val Pro Val His Val Ala Lys Ile Leu
1               5                   10                  15

<210> SEQ ID NO 227
<211> LENGTH: 15
<212> TYPE: PRT
```

```
<213> ORGANISM: Homo sapiens

<400> SEQUENCE: 227

Ala Val Pro Val His Val Ala Lys Ile Leu Thr Phe Pro Glu Lys
1               5                   10                  15

<210> SEQ ID NO 228
<211> LENGTH: 15
<212> TYPE: PRT
<213> ORGANISM: Homo sapiens

<400> SEQUENCE: 228

Val Ala Lys Ile Leu Thr Phe Pro Glu Lys Val Asn Lys Ala Asn
1               5                   10                  15

<210> SEQ ID NO 229
<211> LENGTH: 15
<212> TYPE: PRT
<213> ORGANISM: Homo sapiens

<400> SEQUENCE: 229

Thr Phe Pro Glu Lys Val Asn Lys Ala Asn Ile Asn Phe Leu Arg
1               5                   10                  15

<210> SEQ ID NO 230
<211> LENGTH: 15
<212> TYPE: PRT
<213> ORGANISM: Homo sapiens

<400> SEQUENCE: 230

Val Asn Lys Ala Asn Ile Asn Phe Leu Arg Lys Leu Val Gln Asn
1               5                   10                  15

<210> SEQ ID NO 231
<211> LENGTH: 15
<212> TYPE: PRT
<213> ORGANISM: Homo sapiens

<400> SEQUENCE: 231

Ile Asn Phe Leu Arg Lys Leu Val Gln Asn Gly Pro Glu Val His
1               5                   10                  15

<210> SEQ ID NO 232
<211> LENGTH: 15
<212> TYPE: PRT
<213> ORGANISM: Homo sapiens

<400> SEQUENCE: 232

Lys Leu Val Gln Asn Gly Pro Glu Val His Pro Gly Ala Asn Phe
1               5                   10                  15

<210> SEQ ID NO 233
<211> LENGTH: 15
<212> TYPE: PRT
<213> ORGANISM: Homo sapiens

<400> SEQUENCE: 233

Gly Pro Glu Val His Pro Gly Ala Asn Phe Ile Gln Gln Arg His
1               5                   10                  15

<210> SEQ ID NO 234
<211> LENGTH: 15
<212> TYPE: PRT
<213> ORGANISM: Homo sapiens
```

<400> SEQUENCE: 234

Pro Gly Ala Asn Phe Ile Gln Gln Arg His Thr Gln Met Lys Arg
1               5                   10                  15

<210> SEQ ID NO 235
<211> LENGTH: 15
<212> TYPE: PRT
<213> ORGANISM: Homo sapiens

<400> SEQUENCE: 235

Ile Gln Gln Arg His Thr Gln Met Lys Arg Phe Leu Lys Tyr Gly
1               5                   10                  15

<210> SEQ ID NO 236
<211> LENGTH: 15
<212> TYPE: PRT
<213> ORGANISM: Homo sapiens

<400> SEQUENCE: 236

Thr Gln Met Lys Arg Phe Leu Lys Tyr Gly Asn Arg Glu Lys Met
1               5                   10                  15

<210> SEQ ID NO 237
<211> LENGTH: 15
<212> TYPE: PRT
<213> ORGANISM: Homo sapiens

<400> SEQUENCE: 237

Phe Leu Lys Tyr Gly Asn Arg Glu Lys Met Ala Gln Glu Leu Lys
1               5                   10                  15

<210> SEQ ID NO 238
<211> LENGTH: 15
<212> TYPE: PRT
<213> ORGANISM: Homo sapiens

<400> SEQUENCE: 238

Asn Arg Glu Lys Met Ala Gln Glu Leu Lys Tyr Gly Asp Ile Val
1               5                   10                  15

<210> SEQ ID NO 239
<211> LENGTH: 15
<212> TYPE: PRT
<213> ORGANISM: Homo sapiens

<400> SEQUENCE: 239

Ala Gln Glu Leu Lys Tyr Gly Asp Ile Val Glu Arg His Leu Ile
1               5                   10                  15

<210> SEQ ID NO 240
<211> LENGTH: 15
<212> TYPE: PRT
<213> ORGANISM: Homo sapiens

<400> SEQUENCE: 240

Tyr Gly Asp Ile Val Glu Arg His Leu Ile Asp Gly Asp Val Val
1               5                   10                  15

<210> SEQ ID NO 241
<211> LENGTH: 15
<212> TYPE: PRT
<213> ORGANISM: Homo sapiens

<400> SEQUENCE: 241

Glu Arg His Leu Ile Asp Gly Asp Val Val Leu Phe Asn Arg Gln
1               5                   10                  15

<210> SEQ ID NO 242
<211> LENGTH: 15
<212> TYPE: PRT
<213> ORGANISM: Homo sapiens

<400> SEQUENCE: 242

Asp Gly Asp Val Val Leu Phe Asn Arg Gln Pro Ser Leu His Lys
1               5                   10                  15

<210> SEQ ID NO 243
<211> LENGTH: 15
<212> TYPE: PRT
<213> ORGANISM: Homo sapiens

<400> SEQUENCE: 243

Leu Phe Asn Arg Gln Pro Ser Leu His Lys Leu Ser Ile Met Ala
1               5                   10                  15

<210> SEQ ID NO 244
<211> LENGTH: 15
<212> TYPE: PRT
<213> ORGANISM: Homo sapiens

<400> SEQUENCE: 244

Pro Ser Leu His Lys Leu Ser Ile Met Ala His Leu Ala Arg Val
1               5                   10                  15

<210> SEQ ID NO 245
<211> LENGTH: 15
<212> TYPE: PRT
<213> ORGANISM: Homo sapiens

<400> SEQUENCE: 245

Leu Ser Ile Met Ala His Leu Ala Arg Val Lys Pro His Arg Thr
1               5                   10                  15

<210> SEQ ID NO 246
<211> LENGTH: 15
<212> TYPE: PRT
<213> ORGANISM: Homo sapiens

<400> SEQUENCE: 246

His Leu Ala Arg Val Lys Pro His Arg Thr Phe Arg Phe Asn Glu
1               5                   10                  15

<210> SEQ ID NO 247
<211> LENGTH: 15
<212> TYPE: PRT
<213> ORGANISM: Homo sapiens

<400> SEQUENCE: 247

Lys Pro His Arg Thr Phe Arg Phe Asn Glu Cys Val Cys Thr Pro
1               5                   10                  15

<210> SEQ ID NO 248
<211> LENGTH: 15
<212> TYPE: PRT
<213> ORGANISM: Homo sapiens

<400> SEQUENCE: 248

Phe Arg Phe Asn Glu Cys Val Cys Thr Pro Tyr Asn Ala Asp Phe
1               5                   10                  15

```
<210> SEQ ID NO 249
<211> LENGTH: 15
<212> TYPE: PRT
<213> ORGANISM: Homo sapiens

<400> SEQUENCE: 249

Cys Val Cys Thr Pro Tyr Asn Ala Asp Phe Asp Gly Asp Glu Met
1               5                   10                  15

<210> SEQ ID NO 250
<211> LENGTH: 15
<212> TYPE: PRT
<213> ORGANISM: Homo sapiens

<400> SEQUENCE: 250

Tyr Asn Ala Asp Phe Asp Gly Asp Glu Met Asn Leu His Leu Pro
1               5                   10                  15

<210> SEQ ID NO 251
<211> LENGTH: 15
<212> TYPE: PRT
<213> ORGANISM: Homo sapiens

<400> SEQUENCE: 251

Asp Gly Asp Glu Met Asn Leu His Leu Pro Gln Thr Glu Glu Ala
1               5                   10                  15

<210> SEQ ID NO 252
<211> LENGTH: 15
<212> TYPE: PRT
<213> ORGANISM: Homo sapiens

<400> SEQUENCE: 252

Asn Leu His Leu Pro Gln Thr Glu Glu Ala Lys Ala Glu Ala Leu
1               5                   10                  15

<210> SEQ ID NO 253
<211> LENGTH: 15
<212> TYPE: PRT
<213> ORGANISM: Homo sapiens

<400> SEQUENCE: 253

Gln Thr Glu Glu Ala Lys Ala Glu Ala Leu Val Leu Met Gly Thr
1               5                   10                  15

<210> SEQ ID NO 254
<211> LENGTH: 15
<212> TYPE: PRT
<213> ORGANISM: Homo sapiens

<400> SEQUENCE: 254

Lys Ala Glu Ala Leu Val Leu Met Gly Thr Lys Ala Asn Leu Val
1               5                   10                  15

<210> SEQ ID NO 255
<211> LENGTH: 15
<212> TYPE: PRT
<213> ORGANISM: Homo sapiens

<400> SEQUENCE: 255

Val Leu Met Gly Thr Lys Ala Asn Leu Val Thr Pro Arg Asn Gly
1               5                   10                  15
```

-continued

```
<210> SEQ ID NO 256
<211> LENGTH: 15
<212> TYPE: PRT
<213> ORGANISM: Homo sapiens

<400> SEQUENCE: 256

Lys Ala Asn Leu Val Thr Pro Arg Asn Gly Glu Pro Leu Ile Ala
1               5                   10                  15

<210> SEQ ID NO 257
<211> LENGTH: 15
<212> TYPE: PRT
<213> ORGANISM: Homo sapiens

<400> SEQUENCE: 257

Thr Pro Arg Asn Gly Glu Pro Leu Ile Ala Ala Ile Gln Asp Phe
1               5                   10                  15

<210> SEQ ID NO 258
<211> LENGTH: 15
<212> TYPE: PRT
<213> ORGANISM: Homo sapiens

<400> SEQUENCE: 258

Glu Pro Leu Ile Ala Ala Ile Gln Asp Phe Leu Thr Gly Ala Tyr
1               5                   10                  15

<210> SEQ ID NO 259
<211> LENGTH: 15
<212> TYPE: PRT
<213> ORGANISM: Homo sapiens

<400> SEQUENCE: 259

Ala Ile Gln Asp Phe Leu Thr Gly Ala Tyr Leu Leu Thr Leu Lys
1               5                   10                  15

<210> SEQ ID NO 260
<211> LENGTH: 15
<212> TYPE: PRT
<213> ORGANISM: Homo sapiens

<400> SEQUENCE: 260

Leu Thr Gly Ala Tyr Leu Leu Thr Leu Lys Asp Thr Phe Phe Asp
1               5                   10                  15

<210> SEQ ID NO 261
<211> LENGTH: 15
<212> TYPE: PRT
<213> ORGANISM: Homo sapiens

<400> SEQUENCE: 261

Leu Leu Thr Leu Lys Asp Thr Phe Phe Asp Arg Ala Lys Ala Cys
1               5                   10                  15

<210> SEQ ID NO 262
<211> LENGTH: 15
<212> TYPE: PRT
<213> ORGANISM: Homo sapiens

<400> SEQUENCE: 262

Asp Thr Phe Phe Asp Arg Ala Lys Ala Cys Gln Ile Ile Ala Ser
1               5                   10                  15

<210> SEQ ID NO 263
<211> LENGTH: 15
```

<212> TYPE: PRT
<213> ORGANISM: Homo sapiens

<400> SEQUENCE: 263

Arg Ala Lys Ala Cys Gln Ile Ile Ala Ser Ile Leu Val Gly Lys
1               5                   10                  15

<210> SEQ ID NO 264
<211> LENGTH: 15
<212> TYPE: PRT
<213> ORGANISM: Homo sapiens

<400> SEQUENCE: 264

Gln Ile Ile Ala Ser Ile Leu Val Gly Lys Asp Glu Lys Ile Lys
1               5                   10                  15

<210> SEQ ID NO 265
<211> LENGTH: 15
<212> TYPE: PRT
<213> ORGANISM: Homo sapiens

<400> SEQUENCE: 265

Ile Leu Val Gly Lys Asp Glu Lys Ile Lys Val Arg Leu Pro Pro
1               5                   10                  15

<210> SEQ ID NO 266
<211> LENGTH: 15
<212> TYPE: PRT
<213> ORGANISM: Homo sapiens

<400> SEQUENCE: 266

Asp Glu Lys Ile Lys Val Arg Leu Pro Pro Thr Ile Leu Lys
1               5                   10                  15

<210> SEQ ID NO 267
<211> LENGTH: 15
<212> TYPE: PRT
<213> ORGANISM: Homo sapiens

<400> SEQUENCE: 267

Val Arg Leu Pro Pro Thr Ile Leu Lys Pro Val Thr Leu Trp
1               5                   10                  15

<210> SEQ ID NO 268
<211> LENGTH: 15
<212> TYPE: PRT
<213> ORGANISM: Homo sapiens

<400> SEQUENCE: 268

Pro Thr Ile Leu Lys Pro Val Thr Leu Trp Thr Gly Lys Gln Ile
1               5                   10                  15

<210> SEQ ID NO 269
<211> LENGTH: 15
<212> TYPE: PRT
<213> ORGANISM: Homo sapiens

<400> SEQUENCE: 269

Pro Val Thr Leu Trp Thr Gly Lys Gln Ile Phe Ser Val Ile Leu
1               5                   10                  15

<210> SEQ ID NO 270
<211> LENGTH: 15
<212> TYPE: PRT
<213> ORGANISM: Homo sapiens

<400> SEQUENCE: 270

Thr Gly Lys Gln Ile Phe Ser Val Ile Leu Arg Pro Ser Asp Asp
1               5                   10                  15

<210> SEQ ID NO 271
<211> LENGTH: 15
<212> TYPE: PRT
<213> ORGANISM: Homo sapiens

<400> SEQUENCE: 271

Phe Ser Val Ile Leu Arg Pro Ser Asp Asp Asn Pro Val Arg Ala
1               5                   10                  15

<210> SEQ ID NO 272
<211> LENGTH: 15
<212> TYPE: PRT
<213> ORGANISM: Homo sapiens

<400> SEQUENCE: 272

Arg Pro Ser Asp Asp Asn Pro Val Arg Ala Asn Leu Arg Thr Lys
1               5                   10                  15

<210> SEQ ID NO 273
<211> LENGTH: 15
<212> TYPE: PRT
<213> ORGANISM: Homo sapiens

<400> SEQUENCE: 273

Asn Pro Val Arg Ala Asn Leu Arg Thr Lys Gly Lys Gln Tyr Cys
1               5                   10                  15

<210> SEQ ID NO 274
<211> LENGTH: 15
<212> TYPE: PRT
<213> ORGANISM: Homo sapiens

<400> SEQUENCE: 274

Asn Leu Arg Thr Lys Gly Lys Gln Tyr Cys Gly Lys Gly Glu Asp
1               5                   10                  15

<210> SEQ ID NO 275
<211> LENGTH: 15
<212> TYPE: PRT
<213> ORGANISM: Homo sapiens

<400> SEQUENCE: 275

Gly Lys Gln Tyr Cys Gly Lys Gly Glu Asp Leu Cys Ala Asn Asp
1               5                   10                  15

<210> SEQ ID NO 276
<211> LENGTH: 15
<212> TYPE: PRT
<213> ORGANISM: Homo sapiens

<400> SEQUENCE: 276

Gly Lys Gly Glu Asp Leu Cys Ala Asn Asp Ser Tyr Val Thr Ile
1               5                   10                  15

<210> SEQ ID NO 277
<211> LENGTH: 15
<212> TYPE: PRT
<213> ORGANISM: Homo sapiens

<400> SEQUENCE: 277

```
Leu Cys Ala Asn Asp Ser Tyr Val Thr Ile Gln Asn Ser Glu Leu
1               5                   10                  15

<210> SEQ ID NO 278
<211> LENGTH: 15
<212> TYPE: PRT
<213> ORGANISM: Homo sapiens

<400> SEQUENCE: 278

Ser Tyr Val Thr Ile Gln Asn Ser Glu Leu Met Ser Gly Ser Met
1               5                   10                  15

<210> SEQ ID NO 279
<211> LENGTH: 15
<212> TYPE: PRT
<213> ORGANISM: Homo sapiens

<400> SEQUENCE: 279

Gln Asn Ser Glu Leu Met Ser Gly Ser Met Asp Lys Gly Thr Leu
1               5                   10                  15

<210> SEQ ID NO 280
<211> LENGTH: 15
<212> TYPE: PRT
<213> ORGANISM: Homo sapiens

<400> SEQUENCE: 280

Met Ser Gly Ser Met Asp Lys Gly Thr Leu Gly Ser Gly Ser Lys
1               5                   10                  15

<210> SEQ ID NO 281
<211> LENGTH: 15
<212> TYPE: PRT
<213> ORGANISM: Homo sapiens

<400> SEQUENCE: 281

Asp Lys Gly Thr Leu Gly Ser Gly Ser Lys Asn Asn Ile Phe Tyr
1               5                   10                  15

<210> SEQ ID NO 282
<211> LENGTH: 15
<212> TYPE: PRT
<213> ORGANISM: Homo sapiens

<400> SEQUENCE: 282

Gly Ser Gly Ser Lys Asn Asn Ile Phe Tyr Ile Leu Leu Arg Asp
1               5                   10                  15

<210> SEQ ID NO 283
<211> LENGTH: 15
<212> TYPE: PRT
<213> ORGANISM: Homo sapiens

<400> SEQUENCE: 283

Asn Asn Ile Phe Tyr Ile Leu Leu Arg Asp Trp Gly Gln Asn Glu
1               5                   10                  15

<210> SEQ ID NO 284
<211> LENGTH: 15
<212> TYPE: PRT
<213> ORGANISM: Homo sapiens

<400> SEQUENCE: 284

Ile Leu Leu Arg Asp Trp Gly Gln Asn Glu Ala Ala Asp Ala Met
```

-continued

```
1               5                   10                  15

<210> SEQ ID NO 285
<211> LENGTH: 15
<212> TYPE: PRT
<213> ORGANISM: Homo sapiens

<400> SEQUENCE: 285

Trp Gly Gln Asn Glu Ala Ala Asp Ala Met Ser Arg Leu Ala Arg
1               5                   10                  15

<210> SEQ ID NO 286
<211> LENGTH: 15
<212> TYPE: PRT
<213> ORGANISM: Homo sapiens

<400> SEQUENCE: 286

Ala Ala Asp Ala Met Ser Arg Leu Ala Arg Leu Ala Pro Val Tyr
1               5                   10                  15

<210> SEQ ID NO 287
<211> LENGTH: 15
<212> TYPE: PRT
<213> ORGANISM: Homo sapiens

<400> SEQUENCE: 287

Ser Arg Leu Ala Arg Leu Ala Pro Val Tyr Leu Ser Asn Arg Gly
1               5                   10                  15

<210> SEQ ID NO 288
<211> LENGTH: 15
<212> TYPE: PRT
<213> ORGANISM: Homo sapiens

<400> SEQUENCE: 288

Leu Ala Pro Val Tyr Leu Ser Asn Arg Gly Phe Ser Ile Gly Ile
1               5                   10                  15

<210> SEQ ID NO 289
<211> LENGTH: 15
<212> TYPE: PRT
<213> ORGANISM: Homo sapiens

<400> SEQUENCE: 289

Leu Ser Asn Arg Gly Phe Ser Ile Gly Ile Gly Asp Val Thr Pro
1               5                   10                  15

<210> SEQ ID NO 290
<211> LENGTH: 15
<212> TYPE: PRT
<213> ORGANISM: Homo sapiens

<400> SEQUENCE: 290

Phe Ser Ile Gly Ile Gly Asp Val Thr Pro Gly Gln Gly Leu Leu
1               5                   10                  15

<210> SEQ ID NO 291
<211> LENGTH: 15
<212> TYPE: PRT
<213> ORGANISM: Homo sapiens

<400> SEQUENCE: 291

Gly Asp Val Thr Pro Gly Gln Gly Leu Leu Lys Ala Lys Tyr Glu
1               5                   10                  15
```

<210> SEQ ID NO 292
<211> LENGTH: 15
<212> TYPE: PRT
<213> ORGANISM: Homo sapiens

<400> SEQUENCE: 292

Gly Gln Gly Leu Leu Lys Ala Lys Tyr Glu Leu Leu Asn Ala Gly
1               5                   10                  15

<210> SEQ ID NO 293
<211> LENGTH: 15
<212> TYPE: PRT
<213> ORGANISM: Homo sapiens

<400> SEQUENCE: 293

Lys Ala Lys Tyr Glu Leu Leu Asn Ala Gly Tyr Lys Lys Cys Asp
1               5                   10                  15

<210> SEQ ID NO 294
<211> LENGTH: 15
<212> TYPE: PRT
<213> ORGANISM: Homo sapiens

<400> SEQUENCE: 294

Leu Leu Asn Ala Gly Tyr Lys Lys Cys Asp Glu Tyr Ile Glu Ala
1               5                   10                  15

<210> SEQ ID NO 295
<211> LENGTH: 15
<212> TYPE: PRT
<213> ORGANISM: Homo sapiens

<400> SEQUENCE: 295

Tyr Lys Lys Cys Asp Glu Tyr Ile Glu Ala Leu Asn Thr Gly Lys
1               5                   10                  15

<210> SEQ ID NO 296
<211> LENGTH: 15
<212> TYPE: PRT
<213> ORGANISM: Homo sapiens

<400> SEQUENCE: 296

Glu Tyr Ile Glu Ala Leu Asn Thr Gly Lys Leu Gln Gln Gln Pro
1               5                   10                  15

<210> SEQ ID NO 297
<211> LENGTH: 15
<212> TYPE: PRT
<213> ORGANISM: Homo sapiens

<400> SEQUENCE: 297

Leu Asn Thr Gly Lys Leu Gln Gln Gln Pro Gly Cys Thr Ala Glu
1               5                   10                  15

<210> SEQ ID NO 298
<211> LENGTH: 15
<212> TYPE: PRT
<213> ORGANISM: Homo sapiens

<400> SEQUENCE: 298

Leu Gln Gln Gln Pro Gly Cys Thr Ala Glu Glu Thr Leu Glu Ala
1               5                   10                  15

<210> SEQ ID NO 299

<211> LENGTH: 15
<212> TYPE: PRT
<213> ORGANISM: Homo sapiens

<400> SEQUENCE: 299

Gly Cys Thr Ala Glu Glu Thr Leu Glu Ala Leu Ile Leu Lys Glu
1               5                   10                  15

<210> SEQ ID NO 300
<211> LENGTH: 15
<212> TYPE: PRT
<213> ORGANISM: Homo sapiens

<400> SEQUENCE: 300

Glu Thr Leu Glu Ala Leu Ile Leu Lys Glu Leu Ser Val Ile Arg
1               5                   10                  15

<210> SEQ ID NO 301
<211> LENGTH: 15
<212> TYPE: PRT
<213> ORGANISM: Homo sapiens

<400> SEQUENCE: 301

Leu Ile Leu Lys Glu Leu Ser Val Ile Arg Asp His Ala Gly Ser
1               5                   10                  15

<210> SEQ ID NO 302
<211> LENGTH: 15
<212> TYPE: PRT
<213> ORGANISM: Homo sapiens

<400> SEQUENCE: 302

Leu Ser Val Ile Arg Asp His Ala Gly Ser Ala Cys Leu Arg Glu
1               5                   10                  15

<210> SEQ ID NO 303
<211> LENGTH: 15
<212> TYPE: PRT
<213> ORGANISM: Homo sapiens

<400> SEQUENCE: 303

Asp His Ala Gly Ser Ala Cys Leu Arg Glu Leu Asp Lys Ser Asn
1               5                   10                  15

<210> SEQ ID NO 304
<211> LENGTH: 15
<212> TYPE: PRT
<213> ORGANISM: Homo sapiens

<400> SEQUENCE: 304

Ala Cys Leu Arg Glu Leu Asp Lys Ser Asn Ser Pro Leu Thr Met
1               5                   10                  15

<210> SEQ ID NO 305
<211> LENGTH: 15
<212> TYPE: PRT
<213> ORGANISM: Homo sapiens

<400> SEQUENCE: 305

Leu Asp Lys Ser Asn Ser Pro Leu Thr Met Ala Leu Cys Gly Ser
1               5                   10                  15

<210> SEQ ID NO 306
<211> LENGTH: 15
<212> TYPE: PRT

<213> ORGANISM: Homo sapiens

<400> SEQUENCE: 306

Ser Pro Leu Thr Met Ala Leu Cys Gly Ser Lys Gly Ser Phe Ile
1               5                   10                  15

<210> SEQ ID NO 307
<211> LENGTH: 15
<212> TYPE: PRT
<213> ORGANISM: Homo sapiens

<400> SEQUENCE: 307

Ala Leu Cys Gly Ser Lys Gly Ser Phe Ile Asn Ile Ser Gln Met
1               5                   10                  15

<210> SEQ ID NO 308
<211> LENGTH: 15
<212> TYPE: PRT
<213> ORGANISM: Homo sapiens

<400> SEQUENCE: 308

Lys Gly Ser Phe Ile Asn Ile Ser Gln Met Ile Ala Cys Val Gly
1               5                   10                  15

<210> SEQ ID NO 309
<211> LENGTH: 15
<212> TYPE: PRT
<213> ORGANISM: Homo sapiens

<400> SEQUENCE: 309

Asn Ile Ser Gln Met Ile Ala Cys Val Gly Gln Gln Ala Ile Ser
1               5                   10                  15

<210> SEQ ID NO 310
<211> LENGTH: 15
<212> TYPE: PRT
<213> ORGANISM: Homo sapiens

<400> SEQUENCE: 310

Ile Ala Cys Val Gly Gln Gln Ala Ile Ser Gly Ser Arg Val Pro
1               5                   10                  15

<210> SEQ ID NO 311
<211> LENGTH: 15
<212> TYPE: PRT
<213> ORGANISM: Homo sapiens

<400> SEQUENCE: 311

Gln Gln Ala Ile Ser Gly Ser Arg Val Pro Asp Gly Phe Glu Asn
1               5                   10                  15

<210> SEQ ID NO 312
<211> LENGTH: 15
<212> TYPE: PRT
<213> ORGANISM: Homo sapiens

<400> SEQUENCE: 312

Gly Ser Arg Val Pro Asp Gly Phe Glu Asn Arg Ser Leu Pro His
1               5                   10                  15

<210> SEQ ID NO 313
<211> LENGTH: 15
<212> TYPE: PRT
<213> ORGANISM: Homo sapiens

<400> SEQUENCE: 313

Asp Gly Phe Glu Asn Arg Ser Leu Pro His Phe Glu Lys His Ser
1               5                   10                  15

<210> SEQ ID NO 314
<211> LENGTH: 15
<212> TYPE: PRT
<213> ORGANISM: Homo sapiens

<400> SEQUENCE: 314

Arg Ser Leu Pro His Phe Glu Lys His Ser Lys Leu Pro Ala Ala
1               5                   10                  15

<210> SEQ ID NO 315
<211> LENGTH: 15
<212> TYPE: PRT
<213> ORGANISM: Homo sapiens

<400> SEQUENCE: 315

Phe Glu Lys His Ser Lys Leu Pro Ala Ala Lys Gly Phe Val Ala
1               5                   10                  15

<210> SEQ ID NO 316
<211> LENGTH: 15
<212> TYPE: PRT
<213> ORGANISM: Homo sapiens

<400> SEQUENCE: 316

Lys Leu Pro Ala Ala Lys Gly Phe Val Ala Asn Ser Phe Tyr Ser
1               5                   10                  15

<210> SEQ ID NO 317
<211> LENGTH: 15
<212> TYPE: PRT
<213> ORGANISM: Homo sapiens

<400> SEQUENCE: 317

Lys Gly Phe Val Ala Asn Ser Phe Tyr Ser Gly Leu Thr Pro Thr
1               5                   10                  15

<210> SEQ ID NO 318
<211> LENGTH: 15
<212> TYPE: PRT
<213> ORGANISM: Homo sapiens

<400> SEQUENCE: 318

Asn Ser Phe Tyr Ser Gly Leu Thr Pro Thr Glu Phe Phe His
1               5                   10                  15

<210> SEQ ID NO 319
<211> LENGTH: 15
<212> TYPE: PRT
<213> ORGANISM: Homo sapiens

<400> SEQUENCE: 319

Gly Leu Thr Pro Thr Glu Phe Phe His Thr Met Ala Gly Arg
1               5                   10                  15

<210> SEQ ID NO 320
<211> LENGTH: 15
<212> TYPE: PRT
<213> ORGANISM: Homo sapiens

<400> SEQUENCE: 320

```
Glu Phe Phe Phe His Thr Met Ala Gly Arg Glu Gly Leu Val Asp
1               5                   10                  15
```

<210> SEQ ID NO 321
<211> LENGTH: 15
<212> TYPE: PRT
<213> ORGANISM: Homo sapiens

<400> SEQUENCE: 321

```
Thr Met Ala Gly Arg Glu Gly Leu Val Asp Thr Ala Val Lys Thr
1               5                   10                  15
```

<210> SEQ ID NO 322
<211> LENGTH: 15
<212> TYPE: PRT
<213> ORGANISM: Homo sapiens

<400> SEQUENCE: 322

```
Glu Gly Leu Val Asp Thr Ala Val Lys Thr Ala Glu Thr Gly Tyr
1               5                   10                  15
```

<210> SEQ ID NO 323
<211> LENGTH: 15
<212> TYPE: PRT
<213> ORGANISM: Homo sapiens

<400> SEQUENCE: 323

```
Thr Ala Val Lys Thr Ala Glu Thr Gly Tyr Met Gln Arg Arg Leu
1               5                   10                  15
```

<210> SEQ ID NO 324
<211> LENGTH: 15
<212> TYPE: PRT
<213> ORGANISM: Homo sapiens

<400> SEQUENCE: 324

```
Ala Glu Thr Gly Tyr Met Gln Arg Arg Leu Val Lys Ser Leu Glu
1               5                   10                  15
```

<210> SEQ ID NO 325
<211> LENGTH: 15
<212> TYPE: PRT
<213> ORGANISM: Homo sapiens

<400> SEQUENCE: 325

```
Met Gln Arg Arg Leu Val Lys Ser Leu Glu Asp Leu Cys Ser Gln
1               5                   10                  15
```

<210> SEQ ID NO 326
<211> LENGTH: 15
<212> TYPE: PRT
<213> ORGANISM: Homo sapiens

<400> SEQUENCE: 326

```
Val Lys Ser Leu Glu Asp Leu Cys Ser Gln Tyr Asp Leu Thr Val
1               5                   10                  15
```

<210> SEQ ID NO 327
<211> LENGTH: 15
<212> TYPE: PRT
<213> ORGANISM: Homo sapiens

<400> SEQUENCE: 327

```
Asp Leu Cys Ser Gln Tyr Asp Leu Thr Val Arg Ser Ser Thr Gly
1               5                   10                  15
```

```
<210> SEQ ID NO 328
<211> LENGTH: 15
<212> TYPE: PRT
<213> ORGANISM: Homo sapiens

<400> SEQUENCE: 328

Tyr Asp Leu Thr Val Arg Ser Ser Thr Gly Asp Ile Ile Gln Phe
1               5                   10                  15

<210> SEQ ID NO 329
<211> LENGTH: 15
<212> TYPE: PRT
<213> ORGANISM: Homo sapiens

<400> SEQUENCE: 329

Arg Ser Ser Thr Gly Asp Ile Ile Gln Phe Ile Tyr Gly Gly Asp
1               5                   10                  15

<210> SEQ ID NO 330
<211> LENGTH: 15
<212> TYPE: PRT
<213> ORGANISM: Homo sapiens

<400> SEQUENCE: 330

Asp Ile Ile Gln Phe Ile Tyr Gly Gly Asp Gly Leu Asp Pro Ala
1               5                   10                  15

<210> SEQ ID NO 331
<211> LENGTH: 15
<212> TYPE: PRT
<213> ORGANISM: Homo sapiens

<400> SEQUENCE: 331

Ile Tyr Gly Gly Asp Gly Leu Asp Pro Ala Ala Met Glu Gly Lys
1               5                   10                  15

<210> SEQ ID NO 332
<211> LENGTH: 15
<212> TYPE: PRT
<213> ORGANISM: Homo sapiens

<400> SEQUENCE: 332

Gly Leu Asp Pro Ala Ala Met Glu Gly Lys Asp Glu Pro Leu Glu
1               5                   10                  15

<210> SEQ ID NO 333
<211> LENGTH: 15
<212> TYPE: PRT
<213> ORGANISM: Homo sapiens

<400> SEQUENCE: 333

Ala Met Glu Gly Lys Asp Glu Pro Leu Glu Phe Lys Arg Val Leu
1               5                   10                  15

<210> SEQ ID NO 334
<211> LENGTH: 15
<212> TYPE: PRT
<213> ORGANISM: Homo sapiens

<400> SEQUENCE: 334

Asp Glu Pro Leu Glu Phe Lys Arg Val Leu Asp Asn Ile Lys Ala
1               5                   10                  15
```

-continued

<210> SEQ ID NO 335
<211> LENGTH: 15
<212> TYPE: PRT
<213> ORGANISM: Homo sapiens

<400> SEQUENCE: 335

Phe Lys Arg Val Leu Asp Asn Ile Lys Ala Val Phe Pro Cys Pro
1               5                   10                  15

<210> SEQ ID NO 336
<211> LENGTH: 15
<212> TYPE: PRT
<213> ORGANISM: Homo sapiens

<400> SEQUENCE: 336

Asp Asn Ile Lys Ala Val Phe Pro Cys Pro Ser Glu Pro Ala Leu
1               5                   10                  15

<210> SEQ ID NO 337
<211> LENGTH: 15
<212> TYPE: PRT
<213> ORGANISM: Homo sapiens

<400> SEQUENCE: 337

Val Phe Pro Cys Pro Ser Glu Pro Ala Leu Ser Lys Asn Glu Leu
1               5                   10                  15

<210> SEQ ID NO 338
<211> LENGTH: 15
<212> TYPE: PRT
<213> ORGANISM: Homo sapiens

<400> SEQUENCE: 338

Ser Glu Pro Ala Leu Ser Lys Asn Glu Leu Ile Leu Thr Thr Glu
1               5                   10                  15

<210> SEQ ID NO 339
<211> LENGTH: 15
<212> TYPE: PRT
<213> ORGANISM: Homo sapiens

<400> SEQUENCE: 339

Ser Lys Asn Glu Leu Ile Leu Thr Thr Glu Ser Ile Met Lys Lys
1               5                   10                  15

<210> SEQ ID NO 340
<211> LENGTH: 15
<212> TYPE: PRT
<213> ORGANISM: Homo sapiens

<400> SEQUENCE: 340

Ile Leu Thr Thr Glu Ser Ile Met Lys Lys Ser Glu Phe Leu Cys
1               5                   10                  15

<210> SEQ ID NO 341
<211> LENGTH: 15
<212> TYPE: PRT
<213> ORGANISM: Homo sapiens

<400> SEQUENCE: 341

Ser Ile Met Lys Lys Ser Glu Phe Leu Cys Lys Tyr Met Arg Ala
1               5                   10                  15

<210> SEQ ID NO 342
<211> LENGTH: 15

```
<212> TYPE: PRT
<213> ORGANISM: Homo sapiens

<400> SEQUENCE: 342

Ser Glu Phe Leu Cys Lys Tyr Met Arg Ala Gln Met Glu Pro Gly
1               5                   10                  15

<210> SEQ ID NO 343
<211> LENGTH: 15
<212> TYPE: PRT
<213> ORGANISM: Homo sapiens

<400> SEQUENCE: 343

Lys Tyr Met Arg Ala Gln Met Glu Pro Gly Ser Ala Val Gly Ala
1               5                   10                  15

<210> SEQ ID NO 344
<211> LENGTH: 15
<212> TYPE: PRT
<213> ORGANISM: Homo sapiens

<400> SEQUENCE: 344

Gln Met Glu Pro Gly Ser Ala Val Gly Ala Leu Cys Ala Gln Ser
1               5                   10                  15

<210> SEQ ID NO 345
<211> LENGTH: 15
<212> TYPE: PRT
<213> ORGANISM: Homo sapiens

<400> SEQUENCE: 345

Ser Ala Val Gly Ala Leu Cys Ala Gln Ser Ile Gly Glu Pro Gly
1               5                   10                  15

<210> SEQ ID NO 346
<211> LENGTH: 15
<212> TYPE: PRT
<213> ORGANISM: Homo sapiens

<400> SEQUENCE: 346

Leu Cys Ala Gln Ser Ile Gly Glu Pro Gly Thr Gln Met Thr Leu
1               5                   10                  15

<210> SEQ ID NO 347
<211> LENGTH: 15
<212> TYPE: PRT
<213> ORGANISM: Homo sapiens

<400> SEQUENCE: 347

Ile Gly Glu Pro Gly Thr Gln Met Thr Leu Lys Thr Phe His Phe
1               5                   10                  15

<210> SEQ ID NO 348
<211> LENGTH: 15
<212> TYPE: PRT
<213> ORGANISM: Homo sapiens

<400> SEQUENCE: 348

Thr Gln Met Thr Leu Lys Thr Phe His Phe Ala Gly Val Ala Ser
1               5                   10                  15

<210> SEQ ID NO 349
<211> LENGTH: 15
<212> TYPE: PRT
<213> ORGANISM: Homo sapiens
```

<400> SEQUENCE: 349

Lys Thr Phe His Phe Ala Gly Val Ala Ser Met Asn Ile Thr Leu
1               5                   10                  15

<210> SEQ ID NO 350
<211> LENGTH: 15
<212> TYPE: PRT
<213> ORGANISM: Homo sapiens

<400> SEQUENCE: 350

Ala Gly Val Ala Ser Met Asn Ile Thr Leu Gly Val Pro Arg Ile
1               5                   10                  15

<210> SEQ ID NO 351
<211> LENGTH: 15
<212> TYPE: PRT
<213> ORGANISM: Homo sapiens

<400> SEQUENCE: 351

Met Asn Ile Thr Leu Gly Val Pro Arg Ile Lys Glu Ile Ile Asn
1               5                   10                  15

<210> SEQ ID NO 352
<211> LENGTH: 15
<212> TYPE: PRT
<213> ORGANISM: Homo sapiens

<400> SEQUENCE: 352

Gly Val Pro Arg Ile Lys Glu Ile Ile Asn Ala Ser Lys Ala Ile
1               5                   10                  15

<210> SEQ ID NO 353
<211> LENGTH: 15
<212> TYPE: PRT
<213> ORGANISM: Homo sapiens

<400> SEQUENCE: 353

Lys Glu Ile Ile Asn Ala Ser Lys Ala Ile Cys Gln Asp Ser Phe
1               5                   10                  15

<210> SEQ ID NO 354
<211> LENGTH: 15
<212> TYPE: PRT
<213> ORGANISM: Homo sapiens

<400> SEQUENCE: 354

Ala Ser Lys Ala Ile Cys Gln Asp Ser Phe Leu Gln Glu Ile Lys
1               5                   10                  15

<210> SEQ ID NO 355
<211> LENGTH: 15
<212> TYPE: PRT
<213> ORGANISM: Homo sapiens

<400> SEQUENCE: 355

Cys Gln Asp Ser Phe Leu Gln Glu Ile Lys Lys Phe Ile Lys Gly
1               5                   10                  15

<210> SEQ ID NO 356
<211> LENGTH: 15
<212> TYPE: PRT
<213> ORGANISM: Homo sapiens

<400> SEQUENCE: 356

Leu Gln Glu Ile Lys Lys Phe Ile Lys Gly Val Ser Glu Lys Ile
1               5                   10                  15

<210> SEQ ID NO 357
<211> LENGTH: 15
<212> TYPE: PRT
<213> ORGANISM: Homo sapiens

<400> SEQUENCE: 357

Lys Phe Ile Lys Gly Val Ser Glu Lys Ile Lys Lys Thr Arg Asp
1               5                   10                  15

<210> SEQ ID NO 358
<211> LENGTH: 15
<212> TYPE: PRT
<213> ORGANISM: Homo sapiens

<400> SEQUENCE: 358

Val Ser Glu Lys Ile Lys Lys Thr Arg Asp Lys Tyr Gly Ile Asn
1               5                   10                  15

<210> SEQ ID NO 359
<211> LENGTH: 15
<212> TYPE: PRT
<213> ORGANISM: Homo sapiens

<400> SEQUENCE: 359

Lys Lys Thr Arg Asp Lys Tyr Gly Ile Asn Asp Asn Gly Thr Thr
1               5                   10                  15

<210> SEQ ID NO 360
<211> LENGTH: 15
<212> TYPE: PRT
<213> ORGANISM: Homo sapiens

<400> SEQUENCE: 360

Lys Tyr Gly Ile Asn Asp Asn Gly Thr Thr Glu Pro Arg Val Leu
1               5                   10                  15

<210> SEQ ID NO 361
<211> LENGTH: 15
<212> TYPE: PRT
<213> ORGANISM: Homo sapiens

<400> SEQUENCE: 361

Asp Asn Gly Thr Thr Glu Pro Arg Val Leu Tyr Gln Leu Asp Arg
1               5                   10                  15

<210> SEQ ID NO 362
<211> LENGTH: 15
<212> TYPE: PRT
<213> ORGANISM: Homo sapiens

<400> SEQUENCE: 362

Glu Pro Arg Val Leu Tyr Gln Leu Asp Arg Ile Thr Pro Thr Gln
1               5                   10                  15

<210> SEQ ID NO 363
<211> LENGTH: 15
<212> TYPE: PRT
<213> ORGANISM: Homo sapiens

<400> SEQUENCE: 363

Tyr Gln Leu Asp Arg Ile Thr Pro Thr Gln Val Glu Lys Phe Leu

```
1               5                   10                  15
```

<210> SEQ ID NO 364
<211> LENGTH: 15
<212> TYPE: PRT
<213> ORGANISM: Homo sapiens

<400> SEQUENCE: 364

```
Ile Thr Pro Thr Gln Val Glu Lys Phe Leu Glu Thr Cys Arg Asp
1               5                   10                  15
```

<210> SEQ ID NO 365
<211> LENGTH: 15
<212> TYPE: PRT
<213> ORGANISM: Homo sapiens

<400> SEQUENCE: 365

```
Val Glu Lys Phe Leu Glu Thr Cys Arg Asp Ser Thr Pro Ile Ile
1               5                   10                  15
```

<210> SEQ ID NO 366
<211> LENGTH: 15
<212> TYPE: PRT
<213> ORGANISM: Homo sapiens

<400> SEQUENCE: 366

```
Glu Thr Cys Arg Asp Ser Thr Pro Ile Ile Thr Ala Gln Leu Asp
1               5                   10                  15
```

<210> SEQ ID NO 367
<211> LENGTH: 15
<212> TYPE: PRT
<213> ORGANISM: Homo sapiens

<400> SEQUENCE: 367

```
Ser Thr Pro Ile Ile Thr Ala Gln Leu Asp Lys Asp Asp Ala
1               5                   10                  15
```

<210> SEQ ID NO 368
<211> LENGTH: 15
<212> TYPE: PRT
<213> ORGANISM: Homo sapiens

<400> SEQUENCE: 368

```
Thr Ala Gln Leu Asp Lys Asp Asp Ala Asp Tyr Ala Arg Leu
1               5                   10                  15
```

<210> SEQ ID NO 369
<211> LENGTH: 15
<212> TYPE: PRT
<213> ORGANISM: Homo sapiens

<400> SEQUENCE: 369

```
Lys Asp Asp Asp Ala Asp Tyr Ala Arg Leu Val Lys Gly Arg Ile
1               5                   10                  15
```

<210> SEQ ID NO 370
<211> LENGTH: 15
<212> TYPE: PRT
<213> ORGANISM: Homo sapiens

<400> SEQUENCE: 370

```
Asp Tyr Ala Arg Leu Val Lys Gly Arg Ile Glu Lys Thr Leu Leu
1               5                   10                  15
```

```
<210> SEQ ID NO 371
<211> LENGTH: 15
<212> TYPE: PRT
<213> ORGANISM: Homo sapiens

<400> SEQUENCE: 371

Val Lys Gly Arg Ile Glu Lys Thr Leu Leu Gly Glu Ile Ser Glu
1               5                   10                  15

<210> SEQ ID NO 372
<211> LENGTH: 15
<212> TYPE: PRT
<213> ORGANISM: Homo sapiens

<400> SEQUENCE: 372

Glu Lys Thr Leu Leu Gly Glu Ile Ser Glu Tyr Ile Glu Glu Val
1               5                   10                  15

<210> SEQ ID NO 373
<211> LENGTH: 15
<212> TYPE: PRT
<213> ORGANISM: Homo sapiens

<400> SEQUENCE: 373

Gly Glu Ile Ser Glu Tyr Ile Glu Glu Val Phe Leu Pro Asp Asp
1               5                   10                  15

<210> SEQ ID NO 374
<211> LENGTH: 15
<212> TYPE: PRT
<213> ORGANISM: Homo sapiens

<400> SEQUENCE: 374

Tyr Ile Glu Glu Val Phe Leu Pro Asp Asp Cys Phe Ile Leu Val
1               5                   10                  15

<210> SEQ ID NO 375
<211> LENGTH: 15
<212> TYPE: PRT
<213> ORGANISM: Homo sapiens

<400> SEQUENCE: 375

Phe Leu Pro Asp Asp Cys Phe Ile Leu Val Lys Leu Ser Leu Glu
1               5                   10                  15

<210> SEQ ID NO 376
<211> LENGTH: 15
<212> TYPE: PRT
<213> ORGANISM: Homo sapiens

<400> SEQUENCE: 376

Cys Phe Ile Leu Val Lys Leu Ser Leu Glu Arg Ile Arg Leu Leu
1               5                   10                  15

<210> SEQ ID NO 377
<211> LENGTH: 15
<212> TYPE: PRT
<213> ORGANISM: Homo sapiens

<400> SEQUENCE: 377

Lys Leu Ser Leu Glu Arg Ile Arg Leu Leu Arg Leu Glu Val Asn
1               5                   10                  15

<210> SEQ ID NO 378
```

```
<210> SEQ ID NO 378
<211> LENGTH: 15
<212> TYPE: PRT
<213> ORGANISM: Homo sapiens

<400> SEQUENCE: 378

Arg Ile Arg Leu Leu Arg Leu Glu Val Asn Ala Glu Thr Val Arg
1               5                   10                  15

<210> SEQ ID NO 379
<211> LENGTH: 15
<212> TYPE: PRT
<213> ORGANISM: Homo sapiens

<400> SEQUENCE: 379

Arg Leu Glu Val Asn Ala Glu Thr Val Arg Tyr Ser Ile Cys Thr
1               5                   10                  15

<210> SEQ ID NO 380
<211> LENGTH: 15
<212> TYPE: PRT
<213> ORGANISM: Homo sapiens

<400> SEQUENCE: 380

Ala Glu Thr Val Arg Tyr Ser Ile Cys Thr Ser Lys Leu Arg Val
1               5                   10                  15

<210> SEQ ID NO 381
<211> LENGTH: 15
<212> TYPE: PRT
<213> ORGANISM: Homo sapiens

<400> SEQUENCE: 381

Tyr Ser Ile Cys Thr Ser Lys Leu Arg Val Lys Pro Gly Asp Val
1               5                   10                  15

<210> SEQ ID NO 382
<211> LENGTH: 15
<212> TYPE: PRT
<213> ORGANISM: Homo sapiens

<400> SEQUENCE: 382

Ser Lys Leu Arg Val Lys Pro Gly Asp Val Ala Val His Gly Glu
1               5                   10                  15

<210> SEQ ID NO 383
<211> LENGTH: 15
<212> TYPE: PRT
<213> ORGANISM: Homo sapiens

<400> SEQUENCE: 383

Lys Pro Gly Asp Val Ala Val His Gly Glu Ala Val Val Cys Val
1               5                   10                  15

<210> SEQ ID NO 384
<211> LENGTH: 15
<212> TYPE: PRT
<213> ORGANISM: Homo sapiens

<400> SEQUENCE: 384

Ala Val His Gly Glu Ala Val Val Cys Val Thr Pro Arg Glu Asn
1               5                   10                  15

<210> SEQ ID NO 385
<211> LENGTH: 15
<212> TYPE: PRT
```

<213> ORGANISM: Homo sapiens

<400> SEQUENCE: 385

Ala Val Val Cys Val Thr Pro Arg Glu Asn Ser Lys Ser Ser Met
1               5                   10                  15

<210> SEQ ID NO 386
<211> LENGTH: 15
<212> TYPE: PRT
<213> ORGANISM: Homo sapiens

<400> SEQUENCE: 386

Thr Pro Arg Glu Asn Ser Lys Ser Ser Met Tyr Tyr Val Leu Gln
1               5                   10                  15

<210> SEQ ID NO 387
<211> LENGTH: 15
<212> TYPE: PRT
<213> ORGANISM: Homo sapiens

<400> SEQUENCE: 387

Ser Lys Ser Ser Met Tyr Tyr Val Leu Gln Phe Leu Lys Glu Asp
1               5                   10                  15

<210> SEQ ID NO 388
<211> LENGTH: 15
<212> TYPE: PRT
<213> ORGANISM: Homo sapiens

<400> SEQUENCE: 388

Tyr Tyr Val Leu Gln Phe Leu Lys Glu Asp Leu Pro Lys Val Val
1               5                   10                  15

<210> SEQ ID NO 389
<211> LENGTH: 15
<212> TYPE: PRT
<213> ORGANISM: Homo sapiens

<400> SEQUENCE: 389

Phe Leu Lys Glu Asp Leu Pro Lys Val Val Val Gln Gly Ile Pro
1               5                   10                  15

<210> SEQ ID NO 390
<211> LENGTH: 15
<212> TYPE: PRT
<213> ORGANISM: Homo sapiens

<400> SEQUENCE: 390

Leu Pro Lys Val Val Val Gln Gly Ile Pro Glu Val Ser Arg Ala
1               5                   10                  15

<210> SEQ ID NO 391
<211> LENGTH: 15
<212> TYPE: PRT
<213> ORGANISM: Homo sapiens

<400> SEQUENCE: 391

Val Gln Gly Ile Pro Glu Val Ser Arg Ala Val Ile His Ile Asp
1               5                   10                  15

<210> SEQ ID NO 392
<211> LENGTH: 15
<212> TYPE: PRT
<213> ORGANISM: Homo sapiens

<400> SEQUENCE: 392

Glu Val Ser Arg Ala Val Ile His Ile Asp Glu Gln Ser Gly Lys
1               5                   10                  15

<210> SEQ ID NO 393
<211> LENGTH: 15
<212> TYPE: PRT
<213> ORGANISM: Homo sapiens

<400> SEQUENCE: 393

Val Ile His Ile Asp Glu Gln Ser Gly Lys Glu Lys Tyr Lys Leu
1               5                   10                  15

<210> SEQ ID NO 394
<211> LENGTH: 15
<212> TYPE: PRT
<213> ORGANISM: Homo sapiens

<400> SEQUENCE: 394

Glu Gln Ser Gly Lys Glu Lys Tyr Lys Leu Leu Val Glu Gly Asp
1               5                   10                  15

<210> SEQ ID NO 395
<211> LENGTH: 15
<212> TYPE: PRT
<213> ORGANISM: Homo sapiens

<400> SEQUENCE: 395

Glu Lys Tyr Lys Leu Leu Val Glu Gly Asp Asn Leu Arg Ala Val
1               5                   10                  15

<210> SEQ ID NO 396
<211> LENGTH: 15
<212> TYPE: PRT
<213> ORGANISM: Homo sapiens

<400> SEQUENCE: 396

Leu Val Glu Gly Asp Asn Leu Arg Ala Val Met Ala Thr His Gly
1               5                   10                  15

<210> SEQ ID NO 397
<211> LENGTH: 15
<212> TYPE: PRT
<213> ORGANISM: Homo sapiens

<400> SEQUENCE: 397

Asn Leu Arg Ala Val Met Ala Thr His Gly Val Lys Gly Thr Arg
1               5                   10                  15

<210> SEQ ID NO 398
<211> LENGTH: 15
<212> TYPE: PRT
<213> ORGANISM: Homo sapiens

<400> SEQUENCE: 398

Met Ala Thr His Gly Val Lys Gly Thr Arg Thr Thr Ser Asn Asn
1               5                   10                  15

<210> SEQ ID NO 399
<211> LENGTH: 15
<212> TYPE: PRT
<213> ORGANISM: Homo sapiens

<400> SEQUENCE: 399

Val Lys Gly Thr Arg Thr Thr Ser Asn Asn Thr Tyr Glu Val Glu
1               5                   10                  15

<210> SEQ ID NO 400
<211> LENGTH: 15
<212> TYPE: PRT
<213> ORGANISM: Homo sapiens

<400> SEQUENCE: 400

Thr Thr Ser Asn Asn Thr Tyr Glu Val Glu Lys Thr Leu Gly Ile
1               5                   10                  15

<210> SEQ ID NO 401
<211> LENGTH: 15
<212> TYPE: PRT
<213> ORGANISM: Homo sapiens

<400> SEQUENCE: 401

Thr Tyr Glu Val Glu Lys Thr Leu Gly Ile Glu Ala Ala Arg Thr
1               5                   10                  15

<210> SEQ ID NO 402
<211> LENGTH: 15
<212> TYPE: PRT
<213> ORGANISM: Homo sapiens

<400> SEQUENCE: 402

Lys Thr Leu Gly Ile Glu Ala Ala Arg Thr Thr Ile Ile Asn Glu
1               5                   10                  15

<210> SEQ ID NO 403
<211> LENGTH: 15
<212> TYPE: PRT
<213> ORGANISM: Homo sapiens

<400> SEQUENCE: 403

Glu Ala Ala Arg Thr Thr Ile Ile Asn Glu Ile Gln Tyr Thr Met
1               5                   10                  15

<210> SEQ ID NO 404
<211> LENGTH: 15
<212> TYPE: PRT
<213> ORGANISM: Homo sapiens

<400> SEQUENCE: 404

Thr Ile Ile Asn Glu Ile Gln Tyr Thr Met Val Asn His Gly Met
1               5                   10                  15

<210> SEQ ID NO 405
<211> LENGTH: 15
<212> TYPE: PRT
<213> ORGANISM: Homo sapiens

<400> SEQUENCE: 405

Ile Gln Tyr Thr Met Val Asn His Gly Met Ser Ile Asp Arg Arg
1               5                   10                  15

<210> SEQ ID NO 406
<211> LENGTH: 15
<212> TYPE: PRT
<213> ORGANISM: Homo sapiens

<400> SEQUENCE: 406

Val Asn His Gly Met Ser Ile Asp Arg Arg His Val Met Leu Leu
1               5                   10                  15

<210> SEQ ID NO 407
<211> LENGTH: 15
<212> TYPE: PRT
<213> ORGANISM: Homo sapiens

<400> SEQUENCE: 407

Ser Ile Asp Arg Arg His Val Met Leu Leu Ser Asp Leu Met Thr
1               5                   10                  15

<210> SEQ ID NO 408
<211> LENGTH: 15
<212> TYPE: PRT
<213> ORGANISM: Homo sapiens

<400> SEQUENCE: 408

His Val Met Leu Leu Ser Asp Leu Met Thr Tyr Lys Gly Glu Val
1               5                   10                  15

<210> SEQ ID NO 409
<211> LENGTH: 15
<212> TYPE: PRT
<213> ORGANISM: Homo sapiens

<400> SEQUENCE: 409

Ser Asp Leu Met Thr Tyr Lys Gly Glu Val Leu Gly Ile Thr Arg
1               5                   10                  15

<210> SEQ ID NO 410
<211> LENGTH: 15
<212> TYPE: PRT
<213> ORGANISM: Homo sapiens

<400> SEQUENCE: 410

Tyr Lys Gly Glu Val Leu Gly Ile Thr Arg Phe Gly Leu Ala Lys
1               5                   10                  15

<210> SEQ ID NO 411
<211> LENGTH: 15
<212> TYPE: PRT
<213> ORGANISM: Homo sapiens

<400> SEQUENCE: 411

Leu Gly Ile Thr Arg Phe Gly Leu Ala Lys Met Lys Glu Ser Val
1               5                   10                  15

<210> SEQ ID NO 412
<211> LENGTH: 15
<212> TYPE: PRT
<213> ORGANISM: Homo sapiens

<400> SEQUENCE: 412

Phe Gly Leu Ala Lys Met Lys Glu Ser Val Leu Met Leu Ala Ser
1               5                   10                  15

<210> SEQ ID NO 413
<211> LENGTH: 15
<212> TYPE: PRT
<213> ORGANISM: Homo sapiens

<400> SEQUENCE: 413

Met Lys Glu Ser Val Leu Met Leu Ala Ser Phe Glu Lys Thr Ala
1               5                   10                  15

```
<210> SEQ ID NO 414
<211> LENGTH: 15
<212> TYPE: PRT
<213> ORGANISM: Homo sapiens

<400> SEQUENCE: 414

Leu Met Leu Ala Ser Phe Glu Lys Thr Ala Asp His Leu Phe Asp
1               5                   10                  15

<210> SEQ ID NO 415
<211> LENGTH: 15
<212> TYPE: PRT
<213> ORGANISM: Homo sapiens

<400> SEQUENCE: 415

Phe Glu Lys Thr Ala Asp His Leu Phe Asp Ala Ala Tyr Phe Gly
1               5                   10                  15

<210> SEQ ID NO 416
<211> LENGTH: 15
<212> TYPE: PRT
<213> ORGANISM: Homo sapiens

<400> SEQUENCE: 416

Asp His Leu Phe Asp Ala Ala Tyr Phe Gly Gln Lys Asp Ser Val
1               5                   10                  15

<210> SEQ ID NO 417
<211> LENGTH: 15
<212> TYPE: PRT
<213> ORGANISM: Homo sapiens

<400> SEQUENCE: 417

Ala Ala Tyr Phe Gly Gln Lys Asp Ser Val Cys Gly Val Ser Glu
1               5                   10                  15

<210> SEQ ID NO 418
<211> LENGTH: 15
<212> TYPE: PRT
<213> ORGANISM: Homo sapiens

<400> SEQUENCE: 418

Gln Lys Asp Ser Val Cys Gly Val Ser Glu Cys Ile Ile Met Gly
1               5                   10                  15

<210> SEQ ID NO 419
<211> LENGTH: 15
<212> TYPE: PRT
<213> ORGANISM: Homo sapiens

<400> SEQUENCE: 419

Cys Gly Val Ser Glu Cys Ile Ile Met Gly Ile Pro Met Asn Ile
1               5                   10                  15

<210> SEQ ID NO 420
<211> LENGTH: 15
<212> TYPE: PRT
<213> ORGANISM: Homo sapiens

<400> SEQUENCE: 420

Cys Ile Ile Met Gly Ile Pro Met Asn Ile Gly Thr Gly Leu Phe
1               5                   10                  15

<210> SEQ ID NO 421
<211> LENGTH: 15
```

```
<212> TYPE: PRT
<213> ORGANISM: Homo sapiens

<400> SEQUENCE: 421

Ile Pro Met Asn Ile Gly Thr Gly Leu Phe Lys Leu Leu His Lys
1               5                   10                  15

<210> SEQ ID NO 422
<211> LENGTH: 15
<212> TYPE: PRT
<213> ORGANISM: Homo sapiens

<400> SEQUENCE: 422

Gly Thr Gly Leu Phe Lys Leu Leu His Lys Ala Asp Arg Asp Pro
1               5                   10                  15

<210> SEQ ID NO 423
<211> LENGTH: 15
<212> TYPE: PRT
<213> ORGANISM: Homo sapiens

<400> SEQUENCE: 423

Lys Leu Leu His Lys Ala Asp Arg Asp Pro Asn Pro Pro Lys Arg
1               5                   10                  15

<210> SEQ ID NO 424
<211> LENGTH: 15
<212> TYPE: PRT
<213> ORGANISM: Homo sapiens

<400> SEQUENCE: 424

Ala Asp Arg Asp Pro Asn Pro Pro Lys Arg Pro Leu Ile Phe Asp
1               5                   10                  15

<210> SEQ ID NO 425
<211> LENGTH: 15
<212> TYPE: PRT
<213> ORGANISM: Homo sapiens

<400> SEQUENCE: 425

Asn Pro Pro Lys Arg Pro Leu Ile Phe Asp Thr Asn Glu Phe His
1               5                   10                  15

<210> SEQ ID NO 426
<211> LENGTH: 15
<212> TYPE: PRT
<213> ORGANISM: Homo sapiens

<400> SEQUENCE: 426

Pro Leu Ile Phe Asp Thr Asn Glu Phe His Ile Pro Leu Val Thr
1               5                   10                  15

<210> SEQ ID NO 427
<211> LENGTH: 15
<212> TYPE: PRT
<213> ORGANISM: Homo sapiens

<400> SEQUENCE: 427

Pro Cys Phe His Val Gly Tyr Phe Arg Ala Val Ile Gly Thr Leu
1               5                   10                  15

<210> SEQ ID NO 428
<211> LENGTH: 15
<212> TYPE: PRT
<213> ORGANISM: Homo sapiens
```

```
<400> SEQUENCE: 428

Gly Tyr Phe Arg Ala Val Ile Gly Thr Leu Gln Met Ile Cys Lys
1               5                   10                  15

<210> SEQ ID NO 429
<211> LENGTH: 15
<212> TYPE: PRT
<213> ORGANISM: Homo sapiens

<400> SEQUENCE: 429

Val Ile Gly Thr Leu Gln Met Ile Cys Lys Thr Cys Cys His Ile
1               5                   10                  15

<210> SEQ ID NO 430
<211> LENGTH: 15
<212> TYPE: PRT
<213> ORGANISM: Homo sapiens

<400> SEQUENCE: 430

Tyr Gln Leu Asp Arg Ile Thr Pro Thr Gln Val Gln Lys Phe Leu
1               5                   10                  15

<210> SEQ ID NO 431
<211> LENGTH: 15
<212> TYPE: PRT
<213> ORGANISM: Homo sapiens

<400> SEQUENCE: 431

Ile Thr Pro Thr Gln Val Gln Lys Phe Leu Glu Thr Cys Arg Asp
1               5                   10                  15

<210> SEQ ID NO 432
<211> LENGTH: 15
<212> TYPE: PRT
<213> ORGANISM: Homo sapiens

<400> SEQUENCE: 432

Val Gln Lys Phe Leu Glu Thr Cys Arg Asp Ser Thr Pro Ile Ile
1               5                   10                  15

<210> SEQ ID NO 433
<211> LENGTH: 15
<212> TYPE: PRT
<213> ORGANISM: Homo sapiens

<400> SEQUENCE: 433

Ile Pro Met Asn Ile Gly Thr Gly Leu Phe Lys Leu Leu His Asn
1               5                   10                  15

<210> SEQ ID NO 434
<211> LENGTH: 15
<212> TYPE: PRT
<213> ORGANISM: Homo sapiens

<400> SEQUENCE: 434

Gly Thr Gly Leu Phe Lys Leu Leu His Asn Ala Asp Arg Asp Pro
1               5                   10                  15
```

```
<210> SEQ ID NO 435
<211> LENGTH: 15
<212> TYPE: PRT
<213> ORGANISM: Homo sapiens

<400> SEQUENCE: 435

Lys Leu Leu His Asn Ala Asp Arg Asp Pro Asn Pro Pro Lys Arg
1               5                   10                  15
```

US 10,874,726 B2

AUTOIMMUNE ANTIGENS AND CANCER

CROSS-REFERENCE TO RELATED APPLICATIONS

This application is a 371 application of International Application PCT/US14/68635 filed Dec. 4, 2014, which claims priority to U.S. Provisional Application Ser. No. 61/911,626, filed on Dec. 4, 2013, the entire contents of which are hereby incorporated by reference.

STATEMENT OF FEDERALLY SPONSORED RESEARCH

This invention was made with government support under CA043460, CA057345, CA062924, AR061439, and AR053503 awarded by the National Institutes of Health. The government has certain rights in the invention.

TECHNICAL FIELD OF THE INVENTION

This invention is related to the area of immunotherapy. In particular, it relates to the area of immunotherapy and cancer.

BACKGROUND OF THE INVENTION

Systemic sclerosis (scleroderma) is a chronic autoimmune rheumatic disease associated with widespread obliterative vasculopathy and tissue fibrosis (1, 2). One of the most striking features of this disease is the temporal clustering of scleroderma and cancer that has been observed in patients with autoantibodies to RPC1 but not in patients with autoantibodies to topoisomerase 1 (TOP1) or centromere protein B (CENPB) (3). A variety of potential mechanisms could explain the occurrence of cancers in scleroderma patients with autoantibodies to RPC1 (4). For example, it is possible that a defective immune system responsible for the autoimmune disease predisposes to neoplasia, and that this effect is more prominent in patients with antibodies to RPC1 than in the other subgroups. Alternatively, it is possible that the cytotoxic, mutagenic therapies used to treat scleroderma patients with more fulminant disease leads to cancer in these individuals; patients with RPC1 antibodies tend to have more severe disease than those with other antibodies. Finally, the reverse scenario is possible: cancer might trigger scleroderma in patients with antibodies to RPC1. In particular, we considered the possibility that occasional cancers might harbor missense mutations in the POLR3A gene. If the altered protein encoded by the mutant POLR3A gene were recognized by the patient's immune system, an immune response against the tumor could theoretically be generated. If cross-reactive with the normal RPC1 protein, this immune response could in turn injure selected tissues thereby inducing scleroderma.

There is a continuing need in the art to develop successful therapies for preventing and treating cancers.

SUMMARY OF THE INVENTION

According to one embodiment of the invention a method is provided. A peptide of 10-40 contiguous amino acid residues of an antigen is administered to a patient. The antigen is one to which humans can raise an autoimmune response, i.e., a human autoimmune antigen. The peptide comprises a variant residue relative to the wild-type antigen and binds with high affinity to an HLA protein of the patient.

According to another embodiment, an isolated peptide of 10-40 contiguous amino acid residues of an antigen is provided. The antigen is one to which humans can raise an autoimmune response, i.e., a human autoimmune antigen. The peptide comprises a variant residue relative to the wild-type antigen and binds with high affinity to an human HLA protein.

These and other embodiments which will be apparent to those of skill in the art upon reading the specification provide the art with new tools for combatting cancers in humans.

BRIEF DESCRIPTION OF THE DRAWINGS

FIG. 1 Mutant and wild type peptide-specific CD4+ T cells in patients SCL4 and SCL42. CD154 expression on CD4+ T cells was assayed after stimulation (18 hr) with patient-specific wild type or mutant RPC1 peptides, PAD4 peptide (negative control), or a pool of peptides from infectious agent antigens (CEFT, positive control). Healthy donors matched for one HLA-DR allele were used as controls. Experiments on SCL-4 (A) and SCL-42 (B) were repeated on separate blood draws, three and two times, respectively, with similar results. Gate frequencies are expressed as percentage of CD4+ T cells. (C) Frequency of peptide-reactive CD4 T cells expressed as fold change over CD154+ CD4 T cells in the unstimulated negative control.

FIG. 3. (Table 1.) Selected clinical and genetic characteristics of the scleroderma patients evaluated in this study FIG. 4. (Table 2.) Allelic ratios of SNP loci within and closely surrounding the POLR3A gene.

FIG. 5. (Table 3) Dominant TCR sequences (SEQ ID NO: 97-102, respectively) identified by massively parallel sequencing after stimulation with wt or mutant peptides FIG. 6. (Fig. S1.) Immunoprecipitations of wt and mutant RPC proteins by sera from scleroderma cancer patients. $^{35}$S-methionine-labeled wt and mutated RPC1 proteins were generated by IVTT ("IVTT Input"). For each radiolabeled RPC1 protein, the amount used for the input gel samples was $\frac{1}{20}$ of the amount used for immunoprecipitation. Immunoprecipitates were electrophoresed on SDS-polyacrylamide gels and visualized by fluorography. (A) Immunoprecipitations (performed in duplicate) with patient sera SCL-2, 4 and 42 ("IVTT IP"). The levels of anti-RPC1 antibodies in each of the sera (assayed by ELISA) is listed; values >80 units denote high levels of these antibodies. (B) Immunoprecipitations were performed with the indicated scleroderma patient and control sera (right panel, "IVTT IP").

FIG. 11. (Table S1.) Demographic and clinical characteristics grouped by autoantibody status FIG. 12. (Table S2.) Primers (forward, reverse, SEQ ID NO: 7-94, respectively) used for loss of heterozygosity analysis.

FIG. 13. (Table S3.) Allelic ratios of SNP loci within and closely surrounding the TOP1 gene.

FIG. 14. (Table S4.) Synthetic peptides (SEQ ID NO: 151-435, respectively) assessed for antibody reactivity.

FIG. 15. (Table S5.) MHC types of the patients with RPOL3A mutations.

FIG. 16. (Table S6.) Patient-specific MHC class I and class II peptides (wild-type, SEQ ID NO: 103-109, 111-117, 119-124, respectively; mutant, SEQ ID NO: 127-133, 135-141, 143-148, respectively) with highest predicted binding affinity

DETAILED DESCRIPTION OF THE INVENTION

Figures 2A, 2B, 2C, 2D, 2E, 2F:
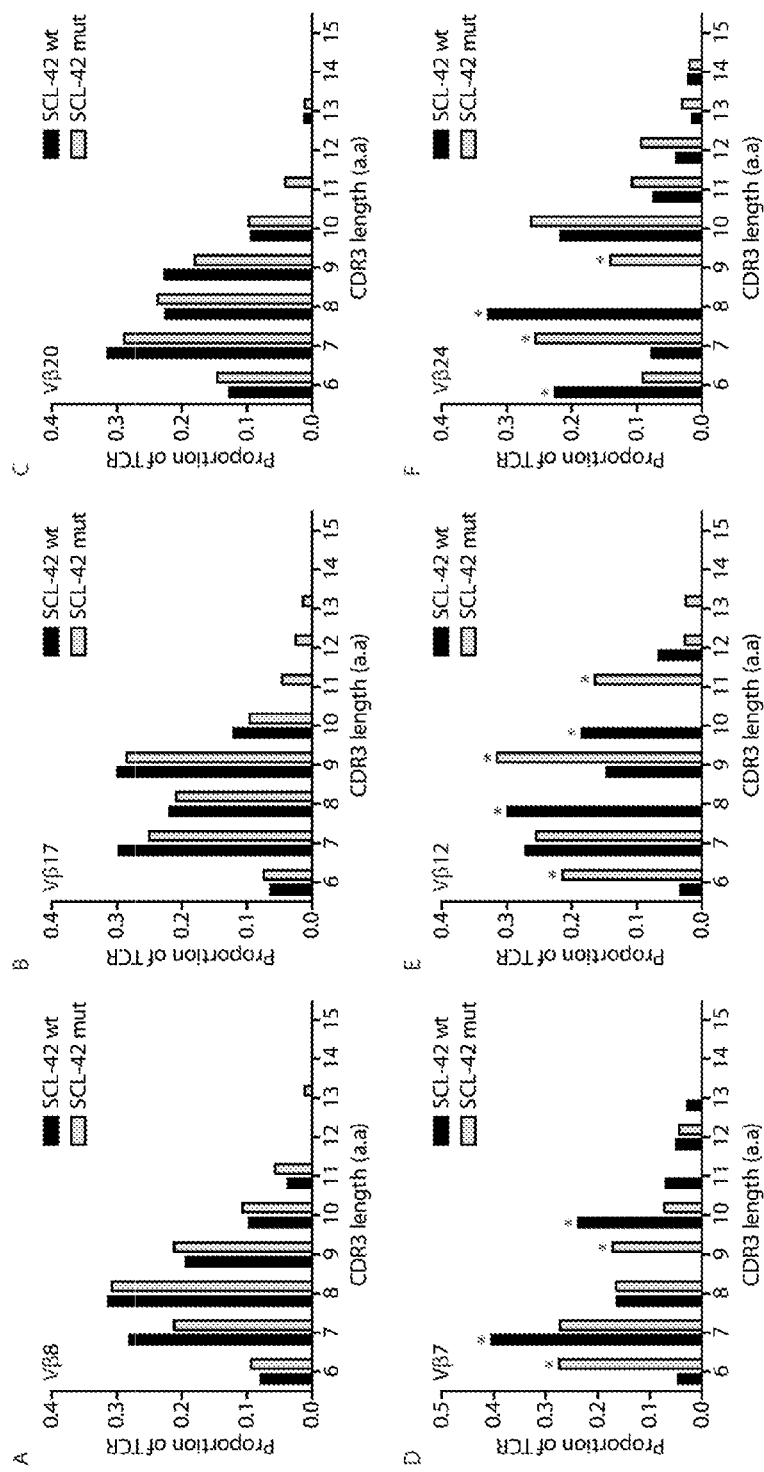
FIG. 2. Vβ-family usage and CDR3 length in patient SCL-42 PBMCs stimulated with wild type (wt) or mutant peptides. SCL-42 PBMCs (peripheral blood mononuclear cells) were stimulated for 6 days with patient-specific mutant (gray bars) and corresponding wt (black bars) RPC1 peptides. No appreciable differences in TCR diversity were observed in Vβ8 (A), Vβ17 (B), and Vβ20 (C) TCR families. Skewing of the CDR3 length distribution in Vβ7 (D), Vβ12 (E), and Vβ24 (F) TCR families was observed and CDR3 lengths that differed by >15% between wt and mutant stimulated PBMCs are indicated (*). CDR3 length is expressed in amino acids (a.a).
Figures 6A, 6B:
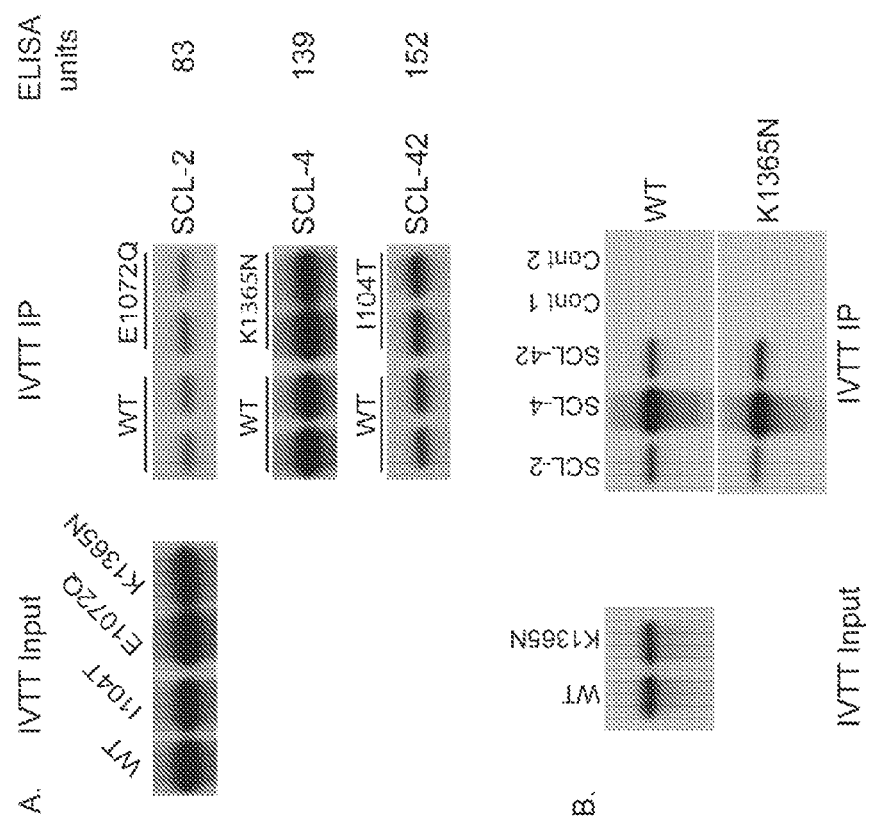
Figure 7:
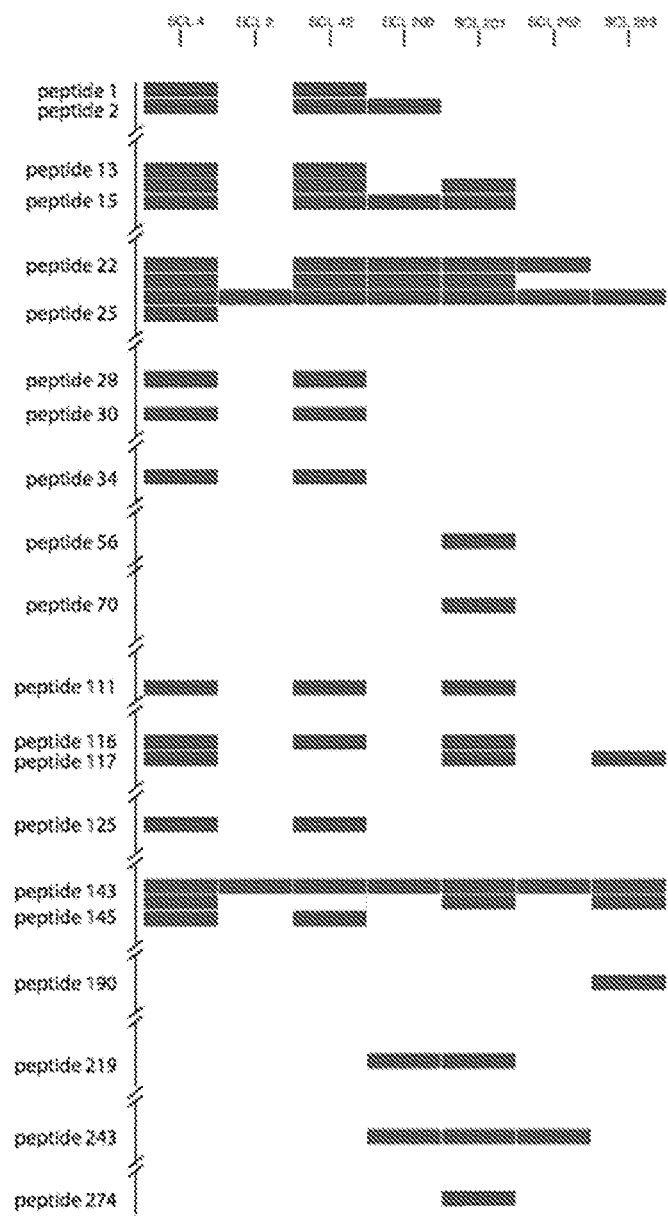
FIG. 7. (Fig. S2.) Peptide array. Peptides determined to be positive binders (see Methods) are shown in blue. Only peptides that bound to the sera of at least one patient are displayed, however all 276 peptides (table S4) spanning the entire wt RPC sequence, as well as peptides spanning the identified POLR3A mutations, were included on the array.
Figure 8:
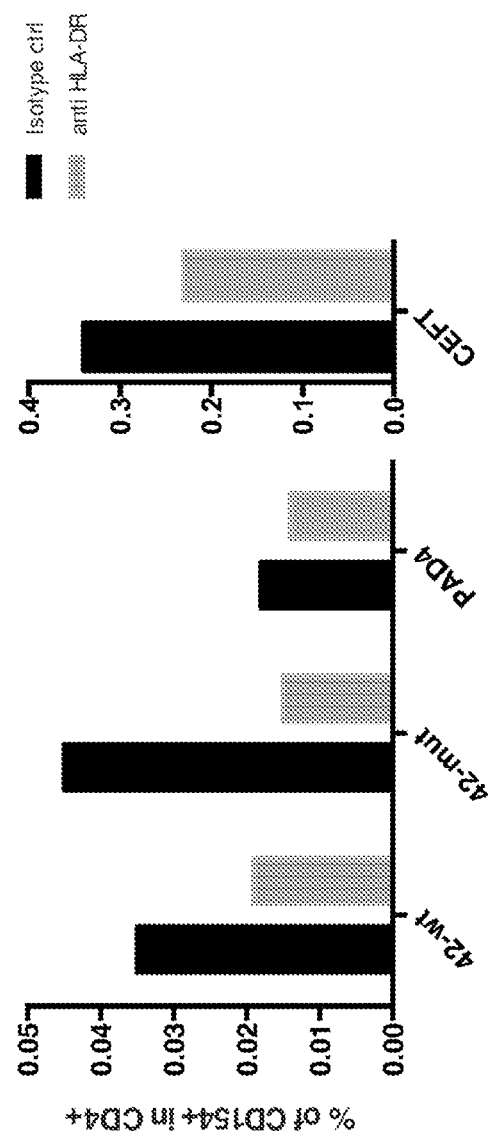
FIG. 8. (Fig. S3.) The effect of HLA-DR blocking antibodies on activation of CD4+ T cells. PBMCs from patient SCL-42 were stimulated with patient-matched mutant and corresponding wild-type RPC1 peptides. The PAD4 peptide and the CEFT pool were used as negative and positive controls, respectively. CD4+ T cell responses to RPC1 peptides were reduced by the presence of HLA-DR blocking antibodies (1 ug/ml) but not by an isotype control antibody used at the same concentration.
Figure 9B:
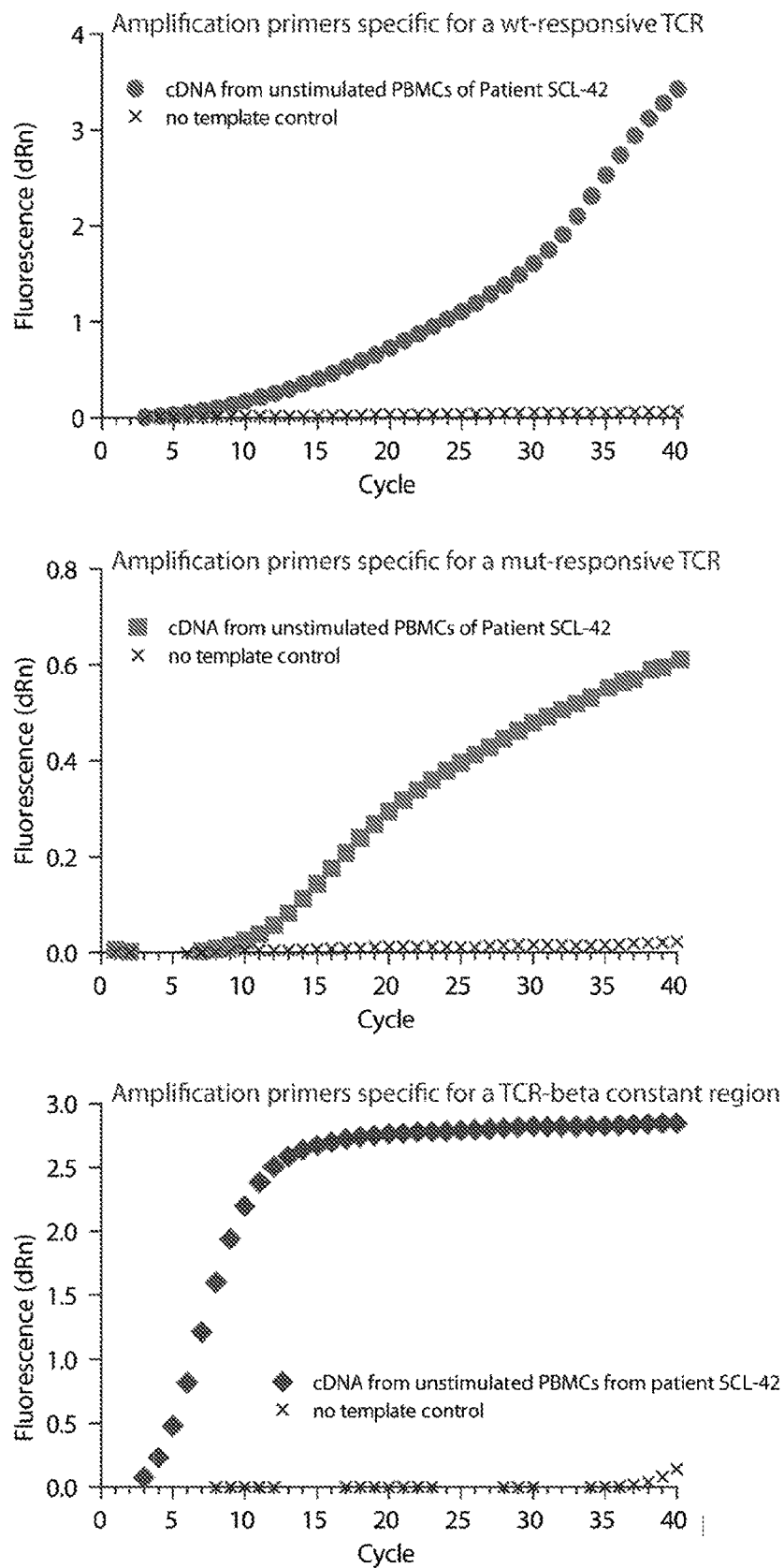
FIG. 9. (Fig. S4.) Detection of wt and mutant-specific TCRs by qPCR. (A) Patient SCL-4 or SCL-42 PBMCs were cultured with patient-specific wt and mutant peptides for six days prior to cDNA isolation and amplification with Vβ24-based primers specific for the TCRs recognizing the wt or mutant forms of POLR3A found in patient SCL-42. As indicated in the lower panel, the relative expression levels of the SCL-42 TCRs following stimulation with the indicated peptides were compared to those of GAPDH and displayed as $2^{-\Delta ct}$ (lower panel). (B) Unstimulated patient SCL-42 PBMCs were used to generate cDNA which was then amplified with Vβ24-based primers specific for the TCRs recognizing the wt or mutant forms of POLR3A found in patient SCL-42. In the lower panel, the same cDNA was used to amplify the TCR-β constant region as a positive control.
Figure 10:
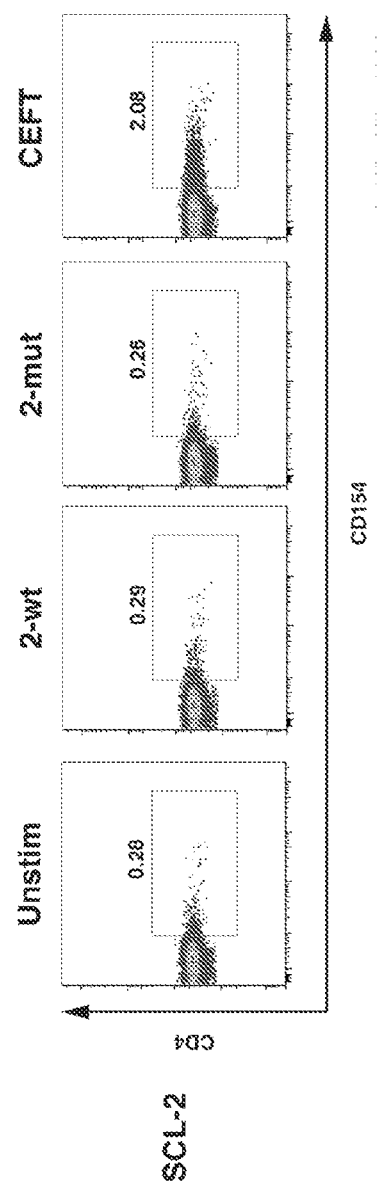
FIG. 10. (Fig. S5.) Mutant and wild type peptide-specific CD4+ T cells in patient SCL2. CD154 expression on CD4+ T cells was assayed by flow cytometry after stimulation (18 h) with patient-specific wild type or mutant RPC1 peptides, or a pool of peptides from infectious agent antigens (CEFT, positive control). Gate frequencies are expressed as percentage of CD4+ T cells.

The inventors have found somatic mutations in autoimmune protein targets in cancer cells in patients that have both an autoimmune disease and a cancer. Patient sera contain T cells specific for the autoimmune protein targets and antibodies specific for the autoimmune protein targets. The autoantibodies do not distinguish between mutant and wild-type forms of the antigen and do not bind to peptides containing the mutant or wild-type residue. However, some CD4+ T cells are reactive with such mutant peptides. Moreover, the cancer cells containing the somatic mutations appear to comprise only a subset of the cancer cells in the patient, i.e., they are subclonal. These findings have implications for the pathogenesis of autoimmune diseases and for the immunological control of naturally occurring cancers.

Autoantigens are antigens to which humans can raise an autoimmune response. Autoantigens are a family of proteins that have been found to be targets of an anti-self immune response associated with diseases. Examples of such diseases are scleroderma, auoimmune rheumatic diseases, such as myositis, vasculitis, and SLE, Sjogren's syndrome, and lupus. Autoantigens known to be involved in such diseases include, but are not limited to the following:

| Lupus | |
|---|---|
| PARP1 | P09874.4 GI: 130781 |
| Histone H1 | NP_005309.1 GI: 4885371 |
| Histone H2 | NP_003505.1 GI: 4504249 |
| Histone H3 | NP_001005464.1 GI: 53793688 |
| Histone H4 | NP_778224.1 GI: 28173560 |
| SmB | Q05856.1 GI: 10720262 |
| SmD | P63162.1 GI: 52783794 |
| SmG | P24715.1 GI: 134126 |
| U1-70k | Q62376.2 GI: 83305641 |
| Ro52 | P19474.1 GI: 133250 |
| Ro60 | P10155.2 GI: 52788235 |
| La | AAH20818.1 GI: 18089160 |
| Ribosomal P2 | NP_000995.1 GI: 4506671 |
| Ribosomal P0 | NP_444505.1 GI: 16933546 |
| Ribosomal P1 | P05386.1 GI: 133051 |
| Ki-67 | P46013.2 GI: 118572663 |
| PCNA | P61074.1 GI: 46576879 |
| NPM1 | P06748.2 GI: 114762 |
| Defensin beta | Large Gene family . . . |
| Defensin a-4 | P12838.2 GI: 399352 |
| Defensin a-3 | P59666.1 GI: 30316323 |
| Defensin a-1 | P59665.1 GI: 30316322 |
| LL37 | NP_004336.3 GI: 348041314 |
| ASF/SF2 | Q07955.2 GI: 730773 |
| SR proteins | NP_006702.1 GI: 6857826 |

| Additional in Sjogren's snndrome | |
|---|---|
| IFI-16 | Q16666.3 GI: 118572657 |
| AQP4 | P55087.2 GI: 2506859 |
| M3R | NP_000731.1 GI: 4502819 |
| Fodrin alpha | Q13813.3 GI: 94730425 |
| Golgin-160 | Q08378.2 GI: 32470610 |
| GM130 | Q08379.3 GI: 294862511 |
| NuMA | Q14980.2 GI: 145559510 |
| Giantin | NP_001243415.1 GI: 374532817 |

| Myositis | |
|---|---|
| RBBP7 | Q16576.1 GI: 2494891 |
| CHD4 | Q14839.2 GI: 311033360 |
| RBBP4 (NuRD) | Q09028.3 1172846 |
| MBD3 | O95983.1 GI: 50400820 |
| SWI/SNF-related | O60264.1 GI: 57014128 |
| CHD3 | Q12873.3 GI: 88911273 |
| HDAC1 | Q13547.1 GI: 2498443 |
| PMS1 | P54277.1 GI: 1709683 |
| PMS2 | P54278.2 GI: 317373266 |
| DNA-PK | P78527.3 GI: 38258929 |
| RNA helicase DHX15 | O43143.2 GI: 13124667 |
| XRCC4 | Q13426.2 GI: 44888352 |
| TIF-1g/TRIM 24 | O15164.3 GI: 12746552 |
| TIF-1b | Q13263.5 GI: 3183179 |
| Ku-70 | P12956.2 GI: 125729 |
| Ku-86 | P13010.3 GI: 125731 |
| NXP2/MORC3 | AAI32732.1 GI: 124375864 |
| HMGCR | P16237.1 GI: 123345 |
| PUF-60 | Q9UHX1.1 GI: 74761960 |
| FUBP1 | Q96AE4.3 GI: 116241370 |
| PM SCL 100k | Q01780.2 GI: 8928564 |
| PM SCL 40k | NP_001029366.1 GI: 77812672 |
| Histidyl tRNA synthetase | P12081.2 GI: 135123 |
| Alanyl tRNA synthetase | P49588.2 GI: 115502460 |
| Lysyl tRNA synthetase | Q15046.3 GI: 20178333 |
| Threonyl tRNA synthetase | P26639.3 GI: 60267755 |
| Asparaginyl tRNA synth | O43776.1 GI: 3915059 |
| MDA5 | Q9BYX4.3 GI: 134047802 |
| SRP54 | P61011.1 GI: 46577650 |
| SRP 72 | O76094.3 GI: 6094347 |
| SRP19 | P09132.3 GI: 115502457 |
| PALLD | Q8WX93.3 GI: 313104206 |
| SAE1 | NP_005491.1 GI: 4885585 |
| SAE2 | NP_005490.1 GI: 4885649 |

| Scleroderma | |
|---|---|
| TOP1 | |
| CENP-A | P49450.1 GI: 1345726 |
| CENP-B | NP_001801.1 GI: 21735415 |
| CENP-C | NP_001803.2 GI: 68508961 |
| Fibrillarin | CAA39935.1 GI: 31395 |
| RPP30 | P783461.1 GI: 13124514 |
| RPP40 | O75818.3 GI: 238054370 |
| RPB1 | P24928.2 GI: 281185484 |
| RPB2 | P30876.1 GI: 401012 |
| POLR3A (RPC1) | O14802.2 GI: 206729892 |
| POLR3C (RPC3) | Q9BUI4.1 GI: 60393871 |
| POLR3B (RPC2) | Q9NW08.2 GI: 29428029 |
| POLR3D (RPC4) | P05423.2 GI: 29429159 |
| RPC5 | Q9NVU0.1 GI: 29428028 |
| RPC6 | Q9H1D9.1 GI: 20139728 |
| RPC7 | O15318.2 GI: 218511818 |
| RPC8 | Q9Y535.1 GI: 29428071 |
| RPC9 | O75575.1 GI: 20532033 |
| RPC10 | Q9Y2Y1.2 GI: 116242768 |
| P80 coilin | P38432.1 GI: 585632 |
| UBF | P17480.1 GI: 136652 |
| Nucleolin | NP_005372.2 GI: 55956788 |
| Centrosomal colon cancer antigen | Q86SQ7.1 GI: 74713839 |
| CEP250 centrosomal | Q9BV73.2 GI: 30580364 |
| PCM1 | AAA60120.1 GI: 450277 |

| Vasculitis | |
|---|---|
| Pr3 | NP_002768.3 GI: 71361688 |
| MPO | NP_000241.1 GI: 4557759 |
| LAMP2 | NP_054701.1 GI: 7669503 |

| General/RA/other | |
|---|---|
| Vimentin | NP_003371.2 GI: 62414289 Q9UM07.2 |
| PAD4 | GI: 296439260 |
| IL-1RA | P18510.1 GI: 124312 |

Mutant peptides may display any change in amino acid sequence from the wild type. This can be conveniently determined with regard to the patient's own normal tissues. Alternatively, wild type found in reference data bases can be used to compare to potential mutant peptides. A mutant peptide may have one or more single nucleotide substitutions, deletions, or insertions. Typically the peptide will have a single nucleotide substitution, deletion, or insertion. In general, it will have less than four, less than three, or less than two nucleotide substitutions, deletions, or insertions. Other than the substitution, deletion, or insertion, the sequence of the peptide will be that of a contiguous stretch of amino acid residues of an autoimmune target antigen. The contiguous stretch will typically be less than 50, less than 40, less than 30, less than 20, less than 18, less than 17, or less than 16 amino acid residues. The contiguous stretch will typically be at least 8, at least 10, at least 12, or at least 13, or at least 14 amino acid residues. An isolated peptide may be made by any means that is practical, including by chemical synthesis, enzymatic synthesis, or in vivo biosynthesis. Isolated peptides are not in a cell or in a whole cell lysate. Typically an isolated peptide is a predominant constituent in a composition, i.e., greater than 10, 20, 30, 40, or 50% of the active ingredients in a composition. A mutant peptide may also be in admixture with a full length protein of the autoimmune antigen. In such case the peptide and the protein may collectively be the predominant constituents in the composition. A peptide may have other moieties attached to the contiguous stretch of autoimmune target antigen sequence. Such moieties may be, for example, radioactive, fluorescent, enzymatic, or adjuvant moieties.

Cancers which can be treated by use of the mutant peptides include any to which humans are subject. These include solid and hematological cancers, such as breast, lung, ovarian, colorectal, and B cell lymphoma. Other cancers which can be treated include Adenoid Cystic Carcinoma, Adrenal Gland Tumor, Amyloidosis, Anal Cancer, Appendix Cancer, Astrocytoma—Childhood, Ataxia-Telangiectasia, Attenuated Familial Adenomatous Polyposis, Beckwith-Wiedemann Syndrome, Bile Duct Cancer, Birt-Hogg-Dube Syndrome, Bladder Cancer, Bone Cancer, Brain Stem Glioma—Childhood, Brain Tumor, Breast Cancer, Breast Cancer—Inflammatory, Breast Cancer—Male, Breast Cancer—Metaplastic, Carcinoid Tumor, Carney Complex, Central Nervous System—Childhood, Cervical Cancer, Childhood Cancer, Colorectal Cancer, Cowden Syndrome, Craniopharyngioma—Childhood, Desmoplastic Infantile Ganglioglioma—Childhood Tumor, Endocrine Tumor, Ependymoma—Childhood, Esophageal Cancer, Ewing Family of Tumors—Childhood, Eye Cancer, Eyelid Cancer, Fallopian Tube Cancer, Familial Adenomatous Polyposis, Familial Malignant Melanoma, Familial Non-VHL Clear Cell Renal Cell Carcinoma, Gallbladder Cancer, Gardner Syndrome, Gastrointestinal Stromal Tumor—GIST, Germ Cell Tumor—Childhood, Gestational Trophoblastic Tumor, Head and Neck Cancer, Hereditary Breast and Ovarian Cancer, Hereditary Diffuse Gastric Cancer, Hereditary Leiomyomatosis and Renal Cell Cancer, Hereditary Mixed Polyposis Syndrome, Hereditary Pancreatitis, Hereditary Papillary Renal Cell Carcinoma, HIV and AIDS-Related Cancer, Islet Cell Tumor, Juvenile Polyposis Syndrome, Kidney Cancer, Lacrimal Gland Tumor, Laryngeal and Hypopharyngeal Cancer, Leukemia—Acute Lymphoblastic—ALL—Childhood, Leukemia—Acute Lymphocytic—ALL, Leukemia—Acute Myeloid—AML, Leukemia—Acute Myeloid—AML—Childhood, Leukemia—B—cell Prolymphocytic Leukemia and Hairy Cell Leukemia, Leukemia—Chronic Lymphocytic—CLL, Leukemia—Chronic Myeloid—CML, Leukemia—Chronic T-Cell Lymphocytic, Leukemia—Eosinophilic, Li-Fraumeni Syndrome, Liver Cancer, Lung Cancer, Lymphoma—Hodgkin, Lymphoma—Hodgkin—Childhood, Lymphoma—Non-Hodgkin, Lymphoma—Non-Hodgkin—Childhood, Lynch Syndrome, Mastocytosis, Medulloblastoma—Childhood, Melanoma, Meningioma, Mesothelioma, Muir-Torre Syndrome, Multiple Endocrine Neoplasia Type 1, Multiple Endocrine Neoplasia Type 2, Multiple Myeloma, Myelodysplastic Syndromes—MDS, MYH-Associated Polyposis, Nasal Cavity and Paranasal Sinus Cancer, Nasopharyngeal Cancer, Neuroblastoma—Childhood, Neuroendocrine Tumor, Neurofibromatosis Type 1, Neurofibromatosis Type 2, Nevoid Basal Cell Carcinoma Syndrome, Oral and Oropharyngeal Cancer, Osteosarcoma—Childhood, Ovarian Cancer, Pancreatic Cancer, Parathyroid Cancer, Penile Cancer, Peutz-Jeghers Syndrome, Pituitary Gland Tumor, Pleuropulmonary Blastoma—Childhood, Prostate Cancer, Retinoblastoma—Childhood, Rhabdomyosarcoma—Childhood, Salivary Gland Cancer, Sarcoma, Sarcoma—Alveolar Soft Part and Cardiac, Sarcoma—Kaposi, Skin Cancer (Non-Melanoma), Small Bowel Cancer, Stomach Cancer, Testicular Cancer, Thymoma, Thyroid Cancer, Tuberous Sclerosis Syndrome, Turcot Syndrome, Unknown Primary, Uterine Cancer, Vaginal Cancer, Von Hippel-Lindau Syndrome, Vulvar Cancer, Waldenstrom's Macroglobulinemia, Werner Syndrome, Wilms Tumor—Childhood, and Xeroderma Pigmentosum.

Binding to human HLA proteins and measurement of the binding can be performed according to any methods known in the art. One method which can be employed uses in silico tools such as Immune Epitope Database (IEDB) analysis resource Consensus tools (7-9). High affinity binding is assessed when the $IC_{50}$ is <50 nM. Moderately high affinity binding is assessed when the $IC_{50}$ is <125 nM. Extremely high affinity binding is assessed when the $IC_{50}$ is <10 nM. Ascertainment of the type of HLA proteins present in a human can be performed using any methods known in the art. Exemplary methods include serotyping, cellular typing, gene sequencing, and phenotyping.

A subset of patients with scleroderma and other autoimmune rheumatic diseases manifest cancer around the time of autoimmune disease diagnosis, suggesting that the two processes might be linked mechanistically (3), (4), (17). In scleroderma, this temporal clustering of scleroderma and cancer appears limited to the subgroup of patients with antibodies to RPC1 (3). In the current work, we demonstrated that the POLR3A locus is genetically altered (by somatic mutation or LOH) in six of eight cancers of patients with antibodies to RPC1, but not in cancers from scleroderma patients with other autoantibody specificities. Moreover, T cells reactive with the mutant forms of RPC1 could be identified in the peripheral blood of two of the three patients tested. These T cells did not simply cross-react with the wild-type form of the peptides, because T cells from subject SCL-4 were not stimulated by the wild type form, and the sequence of the TCRs conferring responsiveness to the wild type and mutant peptides in SCL-42 were largely unrelated.

These genetic and immunologic findings suggest mutation in POLR3A as the initiator of the immune response to RPC1 in an important subset of scleroderma patients. The only tenable alternative to this conclusion is that the onset of scleroderma and the cancer genomes of these patients were unrelated and that the missense mutations and T cell responses directed against the same mutations were coincidental. We believe this alternative is unlikely given the rarity of POLR3A mutations in cancer in general (0.7%, p<10', cosmic database. (18), and the absence of alterations at this locus in scleroderma patients without RPC antibodies (p<0.01). Additionally, in patient SCL-42, there were multiple different nucleotide sequences encoding TCRs with the identical amino acid sequence in T cells stimulated by the mutant peptide (Table 3). This provides strong support for the conclusion that the mutant POLR3A gene product acted as an immunogen initiating the anti-RPC1 immune response in vivo.

Antibodies from all patients with POLR3A mutations recognized wild type and mutant versions of RPC1 similarly, and no antibodies directed specifically against the wild type or mutant peptides could be demonstrated. This suggests that the humoral response does not directly target the area of the mutation or discriminate between mutant and wild type versions of RPC1. The inability of autoantibodies to discriminate between the mutant and wt forms of the antigen is consistent with previous studies showing that a crossreactive humoral response is typical when a novel form of an antigen initially stimulates T cells that specifically recognize the modified antigen (19, 20). The antibody cross-reactivity might contribute to B cell-mediated diversification of autoimmunity, spreading T cell responses to the wild type autoantigen (21, 22).

Our data therefore suggest that the "foreign" antigen triggering the autoimmune response in scleroderma patients is actually a tumor antigen. This complements previous observations indicating cancers can elicit immune responses. It is known that some cases of paraneoplastic syndrome are caused by autoimmunity to proteins expressed in tumors (23); these responses are directed exclusively to the normal protein and there is no evidence that the gene(s) are mutated in the tumors. Conversely, it has been shown that mutant genes in human tumors can elicit an immune response against the mutant gene product (24-26); these immune responses have not been shown to elicit a crossreactive response to the normal gene product that could result in autoimmunity. Finally, it has been shown that an in vitro-generated protein containing multiple (but not single) mutations, when injected into mice, can elicit a broad, cross-reactive immune response against the normal protein that results in autoimmunity (27). In these mice, tumor cells expressing only the wt protein can also be targeted by the subsequent immune response. Our results show that an analogous situation appears to occur in humans when a single, strongly immunogenic epitope is created by somatic mutation in a patient with an appropriate MHC type. However, the generation of an autoreactive immune response alone may not be sufficient to generate the self-sustaining tissue injury seen in scleroderma, and additional factors (genetic, environmental, or target tissue-specific) may be required (28).

Our cohort included cancer patients without anti-RPC1 antibodies (Table 1). While the interval between scleroderma and cancer onset for patients in these patients was long (median of 14.2 years), there were two, patients (SCL-8 and SCL-32) who had relatively short intervals. We did not identify genetic alterations of TOPO1 or CENPB in these two patients. Whether their cancers were adventitious, related to therapy, or due to mutations in genes encoding homologs of TOPO1 or CENPB or proteins that interact with them is unknown but are intriguing hypotheses for future study. Similar factors could also explain the absence of genetic alterations of POLR3A in two of the eight patients with antibodies to RPC1.

The relatively low fraction of neoplastic cells with genetic alterations in the cancers from some of these patients (Tables 1 and 2) suggests that immunoediting of the cancer had occurred, with cells containing these mutations selected against during tumor growth (29). The emergence of cancer in RPC1-positive scleroderma patients may thereby represent escape of the tumor from immune pressure. We speculate that cancers harboring POLR3A mutations had stimulated scleroderma in most patients with the RPC1 form of the disease. However, in the majority of these patients, the immune response had eradicated the cancer by the time scleroderma developed. Patients with a short cancer-autoimmune disease interval have also been described for other autoimmune rheumatic disease phenotypes (e.g. myositis, vasculitis, SLE) and similar mechanisms may be operative in these diseases (17, 30, 31). Given the ubiquitous presence of somatic mutations in solid tumors (32), these new data add credence to the idea that immunoediting could play a major role in limiting the incidence of human cancer—an old hypothesis (33, 34) that has recently garnered more attention (35-37). The data also suggest that this family of autoantigens might be used to generate biologically effective anti-tumor immunity.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Genetic Analysis

We began by searching for missense mutations in the POLR3A gene in tumors from scleroderma patients. We were able to collect tumor and normal tissue samples from eight scleroderma patients who had autoantibodies to RPC1. We also evaluated eight scleroderma patients who had autoantibodies to TOP1 or to CENPB and developed cancers (Table 1). Five of the patients with antibodies to RPC1 developed cancer prior to scleroderma (median of 0.4 years before scleroderma onset), while the remaining 3 developed cancer 0.3-2.5 years after the onset of scleroderma (Table 1). In contrast, patients with autoantibodies to CENPB or TOP1 who developed cancers only did so a median of 14.2 years after the onset of their scleroderma (Table 1). The characteristics of the 16 scleroderma patients, including tumor type, age of diagnosis of cancer, cancer-scleroderma interval, and autoantibody status, are listed in Table 1; additional clinical information is provided in table S1 and (5).

Formalin-fixed, paraffin-embedded tumors from each of the 16 patients were microdissected to enrich for neoplastic cell content, and DNA was purified, blunt-ended, and ligated to adapters suitable for library preparation (5). Libraries from peripheral blood cells of each patient were similarly prepared. Following amplification of the 32 libraries (16 tumor, 16 matched normal), the PCR products were captured using PCR-generated fragments containing all coding sequences of the POLR3A, TOP1, and CENPB genes (5). The captured fragments were evaluated by sequencing on an Illumina instrument, achieving an average coverage of 516 reads per base of the 53 coding-exons of the three genes (range 95- to 2011-fold).

This sequence revealed three somatic, missense variants in POLR3A and none in TOP1 or CENPB (Table 1). All three variants were in the patients with autoantibodies to RPC1. The three somatic mutations were each validated by massively parallel sequencing of PCR products generated from the regions surrounding the mutations (5). Of note, both the capture approach and the direct-PCR sequencing approach showed that one of the three somatic mutations was decidedly subclonal, that is, was present in only a subset of the neoplastic cells: the fraction of mutant alleles in the lung cancer from patient SCL-2 was only 4.3%, far less than the estimated fraction of neoplastic cells in the microdissected sample used for DNA purification (Table 1) (5).

In light of the subclonal nature of one of these mutations, we considered the possibility that cells containing these mutations were selected against during tumor growth, perhaps even disappearing as a result of an immune response. The most frequent way to lose a mutant allele in human cancers is through a gross chromosomal event that results in loss of the entire gene and the surrounding chromosomal region (loss of heterozygosity, LOH) (6). To search for such losses, we designed 19 primer pairs that could each amplify a small fragment containing at least one common single nucleotide polymorphism (SNP) within or surrounding the POLR3A gene (table S2). These primer pairs were used in a multiplexed protocol to evaluate all 16 tumors (5). Five of the eight tumors from scleroderma patients with autoantibodies to RPC1 exhibited LOH (Table 2). These five tumors included three that did not contain a detectable somatic mutation of POLR3A (Table 1). The fraction of neoplastic cells that had undergone LOH could be estimated from the allelic ratios of the SNP data, and in four of the five cases, was subclonal (Table 2). Importantly, none of the tumors from patients with antibodies to TOP1 or CENPB exhibited LOH of the region containing POLR3A (Table 2). As an additional control, we evaluated 21 SNPs within or surrounding the TOP1 locus on chromosome 20 (table S2) and found that none of the 16 tumors from scleroderma patients, regardless of autoantibody status, had undergone LOH of this region (table S3).

In summary, six of eight tumors from scleroderma patients with autoantibodies to RPC1 harbored genetic alterations affecting the POLR3A locus compared to zero of eight tumors from scleroderma patients without anti-RPC1 antibodies (p<0.01, Fisher Exact Probability Test, two-tailed).

Example 2

Immunological Analysis

We began the immunological analysis of these patients by addressing whether RPC1 autoantibodies recognized the mutated protein differently from the wild type (wt) form of the protein. Each of the three abnormal forms of the protein found in scleroderma patients was synthesized by in vitro transcription-translation (IVTT) (5). Wild type and patient-matched mutant RPC1 were then subjected to immunoprecipitation analysis with sera from patients or from normal individuals (control sera). In each case, mutant and wt proteins were precipitated similarly by patient serum, but not precipitated by control sera (Fig. S1), demonstrating that the autoantibodies do not discriminate between wild type and mutant versions of the antigen.

We next constructed a custom peptide microarray to comprehensively identify linear antigenic regions of the RPC1 protein. We synthesized 276 overlapping peptides of 15 amino acids in length, each offset by five amino acids from the previous peptide and covering the entire length of RPC1 (table S4). Peptides that contained each of the three somatic mutations described above were also synthesized (three peptides for each mutant; table S4). These peptides were printed on microarrays and used to assess serum from the three patients with antibodies to RPC1 (SCL-02, SCL-04, and SCL-42) whose cancers harbored POLR3A mutations, and four control patients (SCL-200, SCL-201, SCL-202, SCL-203) who had scleroderma and antibodies to RPC1 but who did not have cancers. Each of the seven serum samples displayed reactivity with at least two of the peptides on the array (Fig. S2). Notably, there was no reactivity to the mutant peptides or their wild type counterparts (i.e., wt amino acids in place of mutant amino acids) in sera from the patients whose cancers harbored these mutations (or in the other patients).

Having shown that there was no demonstrable humoral immune response specific to the mutant RPC1 proteins, we sought to determine if there was a cellular immune response directed against the mutants. We first performed high-resolution class I and II HLA typing on the three scleroderma patients in whom somatically mutated POLR3A genes were identified (table S5) IEDB analysis resource Consensus tools (7-9) were then used to determine whether peptides containing the specific mutations in individual patients were likely to bind with high affinity to that patient's HLA alleles. In patient SCL-42, both wild type and mutant epitopes were predicted to bind with high affinity to both alleles of the patient's class II DR HLA (table S6). This was particularly dramatic for HLA-DR*0701, where the predicted $IC_{50}$ was <1 nM for both the mutant (FHVGYFRAV-IGTLQMI; SEQ ID NO: 95) and wild type peptides (FHV-GYFRAVIGILQMI; SEQ ID NO: 96; table S6). High affinity binding of the wild type and mutant peptides to this patient's other DR allele (HLA-DR*1001) was also predicted (table S6). In patient SCL-4, the mutant peptide was predicted to bind to this patient's HLA-DR*0101 allele with an affinity of 4 nM, 18-fold higher than the affinity of the wt peptide (table S6). The wild type peptide in this region was also predicted to bind, albeit less strongly, to this patient's second allele (26 nM to HLA-DR*1101). Neither wild type nor mutant peptides were predicted to bind with high affinity to the class II molecules of patient SCL-2 (table S6). The algorithms also predicted binding of patient-matched wild type and mutant peptides to a single HLA class I allele in each patient, though the binding affinities were only moderate (27 to 78 nM, table S6).

CD4 cells are known to recognize peptides presented by MHC class II alleles and play central roles in both tumor immunity and autoimmunity (10, 11). In light of this knowledge and our finding that the predicted affinities for class II peptides were much higher than for class I peptides, we searched for CD4 T cells recognizing the predicted peptides in PBMCs from patients whose tumors contained POLR3A mutations. CD154 expression at 18 hours after peptide stimulation was used to identify peptide-activated CD4+ T cells (12, 13). In patient SCL-4, CD4 T cell activation was observed in response to the patient-matched mutant peptide but not to the wt peptide (FIG. 1A, C). Moreover, no CD4 T cell responses to these peptides were observed in T cells from a healthy control matched with SCL-4 at HLA-DR*1101 (FIG. 1A). Thus, the experimental data confirmed the in silico predictions.

The experimental data also confirmed the predicted reactivity of T cells from patient SCL-42, with a 2-fold increase in the number of CD4+ CD154+ T cells in response to both the wt and mutant SCL-42 peptides over control conditions. The frequency of responding cells was about a log lower in SCL-42 compared to SCL-4, with ~1:5,000 CD4 T cells responding (FIG. 1B, C). The CD4 T cell responses to wt and mutant SCL-42 peptides were abolished by treatment with anti-HLA-DR antibodies but not by an isotype control (Fig. S3). As in patient SCL-4, no response to RPC1 peptides was observed in T cells from a healthy control matched with SCL-42 at HLA-DR*0701 (FIG. 1B). As predicted by the in silico binding algorithms (table S6), patient SCL-2 did not respond to either wild type or mutant peptides, but did express CD154 in response to the positive control stimulus, demonstrating that her cells were immune competent (Fig. S5).

These data document the existence of CD4 T cells reactive with peptides containing the RPC1 mutations in two of the three patients studied. The reactivity was patient, peptide, and HLA-type specific. The frequencies of mutant peptide-reactive CD4 T cells observed in these scleroderma patients (~1:600 to ~1:5000, FIG. 1) were in the range observed for antigen-specific CD4+ T cells observed in other autoimmune processes (14). SCL-4 responded only to the mutant peptide, while patient SCL-42 responded to the mutant as well as to the wt peptides (FIG. 1C).

It was possible that the CD4 T cells that were activated in response to the mutant peptide in SCL-42 were the same as those responding to the wt peptide. To evaluate this issue, we performed TCR spectratyping of T cells stimulated by either wt or mutant peptides. Out of the 22 Vβ families analyzed, 12 displayed a similar distribution of their CDR3 lengths in response to wt and mutant peptides including Vβ8, Vβ17, and Vβ20 (FIG. 2A-C). In contrast, significant differences in the distribution of CDR3 lengths were observed for several other Vβs (Vβ3, Vβ5, Vβ7, Vβ12, Vβ16 and Vβ24) (FIG. 2D-F). For some Vβs, marked skewing in CDR3 lengths was observed, with >25% of TCRs from cells-treated with either the mutant or the wt form of the peptide represented by a single CDR3 length. These data suggested that the T cells responding to the mutant peptides were not, in general, those responding to the wt peptides.

To characterize the TCRs in more detail, we determined the sequence of the CDR3 regions in the Vβ7, Vβ12 and Vβ24 PCR products (5). Two striking findings were revealed by massively parallel sequencing of these regions. First, the sequences of the dominant TCRs generated from Tcells stimulated with the wt peptide were completely distinct from those stimulated by the mutant peptide (Table 3). In 5 of 6 dominant TCR's identified by sequencing, the wt- and mutant-specific CDR3 sequences were precisely the lengths predicted by the spectratype analysis (Table 3). The sequencing results therefore strongly supported the conclusion from spectratyping that the mutant and wt peptides had stimulated many distinct T cell clones. Second, there was a high degree of redundancy among the amino acid sequences—but not the nucleotide sequences—of the TCRs identified in this experiment. For example, we identified 17 different nucleotide sequences (represented by 2066 clusters on the sequencing instrument) that encoded the identical CDR3 amino acid sequence in T cells stimulated by the mutant peptide (Table 3). As T cells, unlike B-cells, do not undergo continued evolution once a successful VDJ rearrangement has occurred (15, 16), these data document the existence of multiple, independent T cell clones responding, and presumably binding, to the same mutant peptide.

Finally, we developed CDR3-specific Taqman assays to verify that distinct populations of wt and mutant-specific T cells were present in the peripheral blood of SCL-42 prior to the short-term cultures used in the experiments described above. The Vβ24 TCRs were chosen for this experiment because their CDR3 sequences were the most abundant in the sequencing analysis and were each encoded by multiple distinct nucleotide sequences (Table 3). The TCRs expected to bind the mutant and wild type peptides were detected in uncultured SCL-42 PBMCs (Fig. S4). Neither TCR was detectable in the PMBCs of patient SCL-4, used as a control.

Example 3

Materials and Methods
Clinical Methods

Consenting scleroderma patients with confirmed cancer diagnoses were recruited from the Johns Hopkins Scleroderma Center. Scleroderma patients met the American College of Rheumatology criteria for scleroderma (38). Existing cancer pathology specimens were obtained from prior surgical procedures performed as part of routine clinical care. The closest serum sample to cancer diagnosis was studied in all patients, and DNA and PBMC samples were obtained in consenting participants. The Johns Hopkins Institutional Review Board approved the acquisition of clinical data and all biological samples for this study.

Demographic and clinical data were abstracted from the Johns Hopkins Scleroderma Center database and careful medical record review. Cancer diagnosis dates and histology were determined by review of the initial diagnostic pathology report. The clinical onset of scleroderma was defined by the first scleroderma symptom, either Raynaud's or non-Raynaud's. The interval between scleroderma onset and cancer diagnosis was calculated for each subject (cancer date—scleroderma onset date). The scleroderma cutaneous subtype and modified Rodnan skin score were defined by established criteria (39, 40). All sera were tested for autoantibodies against RPC1, TOP1, and CENPB as previously described (3). Demographic and clinical data were compared across autoantibody groups, and differences in continuous and dichotomous/categorical variables were assessed by the Kruskal-Wallis and Fisher's exact tests, respectively.

The clinical features and cancer types of the 16 patients evaluated in this study are listed in Table 1. Eight patients were positive for anti-RPC1 antibodies, five for anti-TOP1 antibodies and three for anti-CENPB antibodies. Enhanced nucleolar staining with the anti-RPC1 antibodies (3) was observed in the tumors of all eight patients. No subject was positive for more than one autoantibody. Clinical phenotypic characteristics were representative of those expected in each autoantibody group (e.g. severe diffuse disease in RPC1-positive patients), and patients with RPC1 autoantibodies had a shorter interval between scleroderma onset and cancer diagnosis (median of −0.1 years vs. 13.4 years for patients with TOP1 autoantibodies and 34.0 years for patients with CENPB autoantibodies; p=0.05). Seven of the 16 patients had a short interval (+/−2 years) between scleroderma onset and cancer diagnosis, and 6 of these 7 patients (85.7%) were positive for anti-RNA polymerase III antibodies.

Preparation of Illumina Genomic DNA Libraries

Genomic DNA libraries were prepared following Illumina's (Illumina, San Diego, Calif.) suggested protocol with the following modifications. (1) 50 to 75 microliters (μl) of genomic DNA from tumor or normal cells in a total volume of 100 μl TE was fragmented in a Covaris sonicator (Covaris, Woburn, Mass.) to a size of 100 to 500 bp. DNA was purified with a Nucleospin Extract II kit (Cat #740609, Macherey-Nagel, Germany) and eluted in 50 μl of elution buffer included in the kit. (2) 45 μl of purified, fragmented DNA was mixed with 40 μl of H$_2$O, 10 μl End repair reaction buffer and 5 μl of End Repair enzyme. All reagents used for this step and those described below were from New England Biolabs (NEB cat # E6040, Ipswich, Mass.) unless otherwise specified. The 100 μl end-repair mixture was incubated at 20° C. for 30 min, purified by a PCR purification kit (Cat #28104, Qiagen) and eluted with 42 μl of elution buffer (EB). (3) To A-tail, all 42 μl of end-repaired DNA was mixed with 5 μl of 10×dA-Tailing Reaction buffer and 3 μl of Klenow Fragment (3' to 5' exo–). The 50 μl mixture was incubated at 37° C. for 30 min before DNA was purified with a MinElute PCR purification kit (Cat #28004, Qiagen). Purified DNA was eluted with 27 μl of 70° C. EB. (4) For adaptor ligation, 25 μl of A-tailed DNA was mixed with 10 μl of PE-adaptor (Illumina), 10 μl of 5× Ligation buffer and 5 μl of Quick T4 Ligase. The ligation mixture was incubated at room temperature (RT) or 20° C. for 15 min. (5) To purify adaptor-ligated DNA, 50 μl of ligation mixture from step (4) was mixed with 200 μl of NT buffer from NucleoSpin Extract II kit (cat #636972, Clontech, Mountain View, Calif.) and loaded into a NucleoSpin column. The column was centrifuged at 14000 g in a desktop centrifuge for 1 min, washed once with 600 μl of wash buffer (NT3 from Clontech), and centrifuged again for 2 min to dry completely. DNA was eluted in 50 μl elution buffer included in the kit. (6) To obtain an amplified library, ten or twenty PCRs of 50 μl each were set up, each including 30 μl of H$_2$O, 2.5 μl dimethyl sulfoxide (DMSO), 10 μl of 5× Phusion HF buffer, 1.0 μl of a dNTP mix containing 10 mM of each dNTP, 0.5 μl of Illumina PE primer #1, 0.5 μl of Illumina PE primer #2, 0.5 μl of Hot Start Phusion polymerase, and 2.5 or 5 μl of the DNA from step (5). The PCR program used was: 98° C. 1 minute; 10 to 16 cycles of 98° C. for 20 seconds, 65° C. for 30 seconds, 72° C. for 30 seconds; and 72° C. for 5 min. To purify the PCR product, 250 μl PCR mixture (from the ten PCR reactions) was mixed with 500 μl NT buffer from a NucleoSpin Extract II kit and purified as described in step (5). Library DNA was eluted with 70° C. elution buffer and the DNA concentration was estimated by absorption at 260 nm.

Target DNA Enrichment

The targeted regions included all 53 exons of CENPB, POLR3A, TOP1. Capture probes were designed (41) to capture both the plus and the minus strand of the DNA and had a 33-base overlap and were custom-synthesized by Agilent Technologies en masse on a solid phase and used for capture, essentially as described (42). Approximately 3 μg of library DNA was used per capture. After washing, the captured libraries were ethanol-precipitated and redissolved in 20 μl of Tris-EDTA (TE) buffer. The DNA was then amplified in a PCR mix containing 51 μl of distilled water (dH$_2$O), 20 μl of 5× Phusion buffer, 5 μl of dimethyl sulfoxide (DMSO), 2 μl of 10 mM dNTPs, 50 pmol of Illumina forward and reverse primers, and 1 μl of HotStart Phusion enzyme (New England Biolabs) with the following cycling program: 98° C. for 30 s; 15 cycles of 98° C. for 25 s, 65° C. for 30 s, 72° C. for 30 s; and 72° C. for 5 min. The amplified PCR product was purified with a NucleoSpin column (Macherey Nagel Inc.) according to the manufacturer's suggested protocol, except that the NT buffer was not diluted and the DNA bound to the column was eluted in 45 μl of elution buffer. The captured libraries were quantified using an Agilent BioAnalyzer.

Somatic Mutation Identification and LOH Analysis

Captured DNA libraries were sequenced with the Illumina GAIIx Genome Analyzer. Sequencing reads were analyzed and aligned to human genome hg18 with the Eland algorithm in CASAVA 1.6 software (Illumina). A mismatched base was identified as a mutation only when (i) it was identified by ten or more distinct pairs; (ii) the number of distinct tags containing a particular mismatched base was at least 2.5% of the total distinct tags; and (iii) it was not present in >0.5% of the tags in the matched normal sample. Mutations were confirmed by amplification of the relevant region with a single primer pair and evaluated as described in (43). LOH analysis was performed in a similar way, using the primer pairs described in table S3. A patient was considered "informative" for the SNP if DNA from the normal tissue of that patient was heterozygous for the SNP. A tumor was determined to have undergone LOH if >75% of the informative primer pairs in that patient had an allelic ratio less than the mean minus 2 standard deviations of those measured in control individuals without scleroderma. Note that this analysis can only assess allelic imbalance, i.e., a gain in one allele or a loss in the other allele, though it is often (including in the current study) interpreted as LOH, i.e., loss of an allele.

Peptide Microarray

All experiments with the peptide microarray were performed at ProImmune Inc. (Oxford, UK). Peptides were synthesized as 15-mers with 10 overlapping amino acids from the previous peptide, spanning the entire RPC1 protein. Peptides were printed on glass slides with multiple arrays per slide separated with gaskets, allowing for multiple donor sera to be tested per slide. Donor serum was diluted 1:100, 1:500 and 1:1000 and incubated on the array. A fluorescent anti-Human IgG antibody was used as a secondary antibody, results were detected using a CCD camera and analysis was done using MS Excel. Peptides were determined to be potential binders if the normalized average signal intensity was greater than 4× the respective background negative control. Binding was considered positive if the signal intensity was 4× background for all three serum dilutions.

Autoantibody Analysis

RPC1 antibodies were assayed by ELISA using a commercially available kit (Inova Diagnostics). CENP and TOP1 autoanitibody assays were performed as described in (3). To define whether patient antibodies recognized patient-specific mutated forms of RPC1, full-length wild type human POLR3A cDNA was purchased from Origene, and site-directed mutagenesis was performed to generate the three different RPC1 mutants, each with a single point mutation: E1072Q, K1365N and I104T, corresponding to the tumor mutations detected in patients SCL-2, SCL-4 and SCL-42, respectively. All were sequence verified before use. $^{35}$S-methionine-labeled products were generated from the wild type and mutant DNAs by IVTT reactions (Promega kit). Prior to use in immunoprecipitations, the radiolabeled proteins were electrophoresed on SDS-PAGE gels and visualized by fluorography. The radiolabeled signal generated by each of these products was similar (1 μl of E1072Q equivalent to: 1.1, 1.2 and 1.7 μl of I104T, wt and K1365N, respectively). Equivalent radioactive amounts $^{35}$S-methionine-labeled wt and mutated RPC1 proteins were used in immunoprecipitations performed as described in (44) with sera from three cancer scleroderma patients. One μl of each serum was used to immunoprecipitate the wild-type form of RPC1 as well as the specific RPC1 mutation found in the tumor from that patient.

Cell Culture, Stimulation and Flow Cytometry

PBMCs were freshly isolated from whole blood by density-gradient centrifugation (Ficoll-Paque Plus, GE Healthcare), and were used fresh (SCL-42) or frozen (SCL4 and SCL2). For each patient, PBMCs from a donor expressing one matching HLA-DRB1 allele was selected and used as a control. Cells were resuspended to a concentration of $1.5 \times 10^6$ cells/150 µl in RPMI medium supplemented with serum, 2 mM L-glutamine, 100 U/ml penicillin, and 100 µg/ml streptomycin, and were plated onto 96-well flat bottom plates. 1 µg/ml anti-human CD40 blocking antibody (G28.5, Biolegend) was added, and after 30 minutes, cells were stimulated for 18 hours as indicated: 4 µg/ml wild-type or mutant patient-matched RPC1 peptide, 4 µg/ml of peptidyl arginine deiminase 4 (PAD4) peptide as a negative control, or 4 µg/ml of a pool of class-II peptides from infectious agents antigens (CEFT) (Axxora) as a positive control. Peptide storage buffer was used for the unstimulated control. HLA restriction was assessed by stimulating cells in the presence of 1 µg/ml anti-HLA-DR blocking antibody (L243, Biolegend) or 1 µg/ml IgG-2a κ isotype control (MOPC-173, Biolegend).

Cells were washed with PBS after stimulation, stained with live/dead fixable blue dead cell stain (Molecular Probes), and then stained with BV510-conjugated CD3 antibody (OKT3, BioLegend), Pacific Blue-conjugated anti-CD4 antibody (RPA-T4, BD Pharmingen), APC-H7-conjugated anti-CD8 (SK1, BD), and PE-conjugated anti-CD154 antibody (TRAP1, BD Pharmingen). FACS analysis was performed on FACSAria flow cytometer-cell-sorter using FACSDiva (Becton Dickinson) and FlowJo software (Tree Star Inc. Ashland, Oreg., USA).

TCR Spectratyping

The diversity of CDR3 regions for 22 TCR Vβ regions was assessed using the TCRExpress Quantitative Analysis Kit (Biomed Immunotech, Tampa Fla.). Briefly, RNA was isolated from SCL-42 PBMCs after culture for 6 days with wt or mutant peptides (Invitrogen, Carlsbad Calif.), and cDNA was generated using random hexamers (Invitrogen) and You Prime First Strand Beads (GE, Buckinghamshire UK) following the manufacturers protocols. CDR3 regions were amplified from cDNA using two rounds of PCR with Vβ-family specific PCR primers as per the manufacturer's instructions. Fragment length analysis was performed by the Johns Hopkins DNA analysis facility. The distribution of CDR3 lengths for each Vβ-family was determined and expressed as "proportion of TCR". Peaks were considered to be antigen-driven when the observed proportion of a given fragment size differed by more than 10% between wt and mutant-stimulated cells.

TCR Sequencing

TCR libraries were prepared for sequencing using a Truseq sample preparation kit following the manufacturer's suggestions with the following modifications. Input DNA was prepared from the PCR products obtained from spectratyping analysis. Product from wells using primers specific to the CDR3 regions of Vβ3, Vβ5, Vβ7, Vβ12, Vβ16 and Vβ24 were purified using a Qiagen PCR purification kit. DNA was eluted in 30 ul of 65° C. elution buffer. After A-tailing and igation to adaptors, the library was amplified in six reactions with a PCR mix containing 10 ul H$_2$O, 1.5 ul DMSO, 6 ul 5× Phusion buffer, 6 ul dNTPs, 3 ul each of Forward and Reverse Primers, 3 ul Phusion polymerase (2 U/ul) and 2 ul ligation reactions, and cycled using the following program, 98° C. for 30 s; 14 cycles of 98° C. for 10 s, 65° C. for 30 s, 72° C. for 30 s; and 72° C. for 5 min. The resulting product was purified using Ampure beads, quantified with an Agilent Bioanalyzer, and sequenced using an Illumina instrument.

qPCR Detection of Specific TCRs

Custom Taqman assays for specific TCRs were developed using Primer express v2.0 software and synthesized by Applied Biosystems. For detection of the Vβ24 Jβ1.1 wt TCR, a FAM-labeled probe (ACTGAAGCTTTCTTTG-GAC; SEQ ID NO: 1), forward primer (GCACCGGGACA-GTGATGAA; SEQ ID NO: 2), and reverse primer (GGTC-CTCTACAACTGTGAGTTTGGT; SEQ ID NO: 3) were synthesized. For detection of the Vβ24 Jβ1.5 mutant TCR, a FAM-labeled probe (ACAGTAAATCAGCCCCAGC; SEQ ID NO: 4), forward primer (TGTGTGCCACCAGCA-GAGA; SEQ ID NO: 5), and reverse primer (AGTC-GAGTCCCATCACCAAAA; SEQ ID NO: 6) were synthesized. cDNA from Day 0 SCL-42 PBMCs was prepared as described and was amplified by one round of PCR using Vβ24-family specific PCR primers (Biomed Immunotech, Tampa Fla.). Expression of the specific Vβ24 TCRs was determined in triplicate using standard ABI chemistry and reagents.

Example 4

Clinical Descriptions of Anti-RPC1 Positive Patients

As detailed below, the anti-PRC1 positive scleroderma patients with cancer shared many features, including a short interval between the first clinical signs of scleroderma and cancer diagnosis, aggressive cutaneous disease, and a high risk of scleroderma renal crisis.

Patient SCL-1

Patient 1 palpated a breast mass in the summer of 2005 and was diagnosed with a breast invasive ductal carcinoma on 7/26/05. Around the time of her diagnosis, she developed hypertension, thrombocytopenia, seizures, and renal failure that progressed despite blood pressure control. She ultimately initiated peritoneal dialysis. Her breast cancer was treated with lumpectomy, radiation therapy, and doxorubicin. In October of 2005, she began to notice Raynaud's phenomenon, and in October of 2007, she developed skin thickening. When first seen in our Center on Feb. 4, 2008, she was noted to have extensive and severe scleroderma skin thickening with a modified Rodnan skin score (mRSS) of 41 (range is 0-51 with 51 representing most severe disease possible).

Patient SCL-2

Patient 2 was noted to have a mass on a chest radiograph, leading to a diagnosis of a small cell carcinoma of the lung on Mar. 22, 2006. She clearly had Raynaud's phenomenon by April 2006. She was treated with chemotherapy (completed July 2006) and radiation therapy with prophylactic brain irradiation (completed September 2006). By April of 2007, she began to notice worsening of her Raynaud's phenomenon and swelling of her hands followed by the onset of rapid, diffuse skin thickening. She was initially treated for her cutaneous disease with mycophenolate mofetil and was noted to have a mRSS of 47 on her visit to our Center on Sep. 6, 2007. She later required therapy with cyclophosphamide due to concern for interstitial lung disease, and by Dec. 13, 2011, her mRSS had decreased significantly to 5.

Patient SCL-4

Patient 4 had a known BRCA1 mutation and underwent a prophylactic oophorectomy based on her genetic risk. During this procedure, she was found to have stage III ovarian adenocarcinoma with papillary serous features (Apr. 5, 2006). She completed 6 cycles of paclitaxel and cisplatin in August 2006, and around this time developed Raynaud's phenomenon. Her chemotherapy course was complicated by the development of pericarditis with tamponade physiology requiring drainage and a pericardial window, and there was no evidence of an infected or malignant effusion. When first seen here on Jan. 10, 2008, she was noted to have significant skin disease (mRSS 21), numerous tendon friction rubs, a myopathy, and scleroderma renal crisis with a Cr of 1.9. In 2008-2009, she was treated with a number of immunosuppressive agents targeting her cutaneous, muscle, and joint disease including mycophenolate, methotrexate, azathioprine and hydroxychloroquine, and her skin disease was significantly improved by August 2008. In October 2011, she developed a small bowel obstruction with imaging findings consistent with serosal implants in the context of a rising CA 125 level. She began weekly carboplatin, and her CA 125 level had normalized by April 2012.

Patient SCL-13

Patient 13 noticed bilateral hand and ankle swelling in May 2005 and Raynaud's phenomenon in August 2005. She was diagnosed with invasive ductal carcinoma of the breast on Aug. 24, 2005. She was treated with a mastectomy followed by doxorubicin and cyclophosphamide from October-December 2005. In January 2006, she developed worsening skin thickening in her hands, arthralgias and myalgias and began therapy with d-penicillamine and later methotrexate. She also initiated paclitaxel and trastuzumab for her cancer in January 2006. She was seen at our Center Apr. 16, 2007 and was noted to have progressive skin disease (mRSS 30); she was transitioned to mycophenolate for her cutaneous disease and gradually had an improvement in her skin disease (mRSS in 2012 was 2).

Patient SCL-35

Patient 35 was diagnosed with breast ductal carcinoma in situ on Aug. 16, 2004, treated with a mastectomy. In April 2006, she developed symptoms consistent with carpal tunnel syndrome, and by August 2006, she had lower extremity skin thickening and tendon friction rubs. Raynaud's phenomenon developed in January 2007. When first seen at our Center in June 2007, her mRSS was 48, and she was on letrozole for her malignancy. After therapy with cyclophosphamide and mycophenolate, her cutaneous disease significantly improved (mRSS 3 by March 2011).

Patient SCL-42

Patient 42 developed arthralgias and skin thickening in her fingers in March 2007 that rapidly progressed to diffuse skin thickening. In April 2007 she developed Raynaud's phenomenon also. By October 2007, she developed hypertension requiring ACE-inhibitor therapy, and her mRSS was 18. Despite therapy with mycophenolate, her cutaneous disease progressed, and by March 2008, her mRSS had increased to 37. In April 2008, methotrexate was added to her regimen with some improvement in flexibility and new hair growth; however her mRSS remained at 35 in July 2008. In September 2008, in the setting of increased cutaneous activity, she was diagnosed with a stage II, triple negative, invasive ductal cancer of the breast. She was treated with mastectomy (October 2008) and chemotherapy with cyclophosphamide and docetaxel (December 2008-February 2009). Her cutaneous symptoms gradually improved in the setting of IVIG therapy, and by December 2011 her mRSS was 8.

Patient SCL-81

Patient 81 was diagnosed with an adenocarcinoma of the colon with positive lymph nodes in May 2005 requiring bowel resection and 5-FU and platinum chemotherapy. In July 2009, he developed diffuse cutaneous skin disease and by November 2009 had Raynaud's phenomenon. In March 2010, his mRSS was 46.

Patient SCL-82

Patient 82 developed Raynaud's phenomenon and hand swelling in January 2008 and was noted to have a mRSS of 14 in August 2008 while on methotrexate therapy. By January 2009, the patient was on combination mycophenolate and methotrexate therapy for a mRSS of 18. By January 2010, her skin disease was significant improved (mRSS 5), but she was diagnosed with a ductal carcinoma in situ (DCIS) of the breast on Jun. 28, 2010 and treated with a mastectomy.

REFERENCES

The disclosure of each reference cited is expressly incorporated herein.
1. A. Gabrielli, E. V. Avvedimento, T. Krieg, Scleroderma. *The New England journal of medicine* 360, 1989 (2009).
2. M. L. Harris, A. Rosen, Autoimmunity in scleroderma: the origin, pathogenetic role, and clinical significance of autoantibodies. *Current opinion in rheumatology* 15, 778 (2003).
3. A. A. Shah, A. Rosen, L. Hummers, F. Wigley, L. Casciola-Rosen, Close temporal relationship between onset of cancer and scleroderma in patients with RNA polymerase I/III antibodies. *Arthritis and rheumatism* 62, 2787 (2010).
4. A. A. Shah, A. Rosen, Cancer and systemic sclerosis: novel insights into pathogenesis and clinical implications. *Current opinion in rheumatology* 23, 530 (2011).
5. Materials and methods are available as supplementary materials on *Science* Online.
6. A. G. Knudson, Hereditary cancer: two hits revisited. *Journal of cancer research and clinical oncology* 122, 135 (1996).
7. Y. Kim, J. Ponomarenko, Z. Zhu, D. Tamang, P. Wang, J. Greenbaum, C. Lundegaard, A. Sette, O. Lund, P. E. Bourne, M. Nielsen, B. Peters, Immune epitope database analysis resource. *Nucleic acids research* 40, W525 (2012).
8. P. Wang, J. Sidney, C. Dow, B. Mothe, A. Sette, B. Peters, A systematic assessment of MHC class II peptide binding predictions and evaluation of a consensus approach. *PLoS computational biology* 4, e1000048 (2008).
9. P. Wang, J. Sidney, Y. Kim, A. Sette, O. Lund, M. Nielsen, B. Peters, Peptide binding predictions for HLA DR, DP and DQ molecules. *BMC bioinformatics* 11, 568 (2010).
10. Z. C. Ding, G. Zhou, Cytotoxic chemotherapy and CD4+ effector T cells: an emerging alliance for durable antitumor effects. *Clinical & developmental immunology* 2012, 890178 (2012).
11. I. Mellman, G. Coukos, G. Dranoff, Cancer immunotherapy comes of age. *Nature* 480, 480 (2011).
12. P. K. Chattopadhyay, J. Yu, M. Roederer, A live-cell assay to detect antigen-specific CD4+ T cells with diverse cytokine profiles. *Nature medicine* 11, 1113 (2005).
13. M. Frentsch, O. Arbach, D. Kirchhoff, B. Moewes, M. Worm, M. Rothe, A. Scheffold, A. Thiel, Direct access to CD4+ T cells specific for defined antigens according to CD154 expression. *Nature medicine* 11,1118 (2005).
14. G. T. Nepom, J. H. Buckner, E. J. Novak, S. Reichstetter, H. Reijonen, J. Gebe, R. Wang, E. Swanson, W. W. Kwok, HLA class II tetramers: tools for direct analysis of antigen-specific CD4+ T cells. *Arthritis and rheumatism* 46, 5 (2002).
15. K. J. Jackson, M. J. Kidd, Y. Wang, A. M. Collins, The Shape of the Lymphocyte Receptor Repertoire: Lessons from the B Cell Receptor. *Frontiers in immunology* 4, 263 (2013).
16. M. G. McHeyzer-Williams, M. M. Davis, Antigen-specific development of primary and memory T cells in vivo. *Science* 268, 106 (1995).
17. R. Buchbinder, A. Forbes, S. Hall, X. Dennett, G. Giles, Incidence of malignant disease in biopsy-proven inflammatory myopathy. A population-based cohort study. *Annals of internal medicine* 134, 1087 (2001).
18. S. A. Forbes, N. Bindal, S. Bamford, C. Cole, C. Y. Kok, D. Beare, M. Jia, R. Shepherd, K. Leung, A. Menzies, J. W. Teague, P. J. Campbell, M. R. Stratton, P. A. Futreal, COSMIC: mining complete cancer genomes in the Catalogue of Somatic Mutations in Cancer. *Nucleic acids research* 39, D945 (2011).
19. H. A. Doyle, M. J. Mamula, Posttranslational modifications of self-antigens. *Annals of the New York Academy of Sciences* 1050, 1 (2005).
20. M. J. Mamula, R. J. Gee, J. I. Elliott, A. Sette, S. Southwood, P. J. Jones, P. R. Blier, Isoaspartyl posttranslational modification triggers autoimmune responses to self-proteins. *The Journal of biological chemistry* 274, 22321 (1999).
21. R. H. Lin, M. J. Mamula, J. A. Hardin, C. A. Janeway, Jr., Induction of autoreactive B cells allows priming of autoreactive T cells. *The Journal of experimental medicine* 173, 1433 (1991).
22. M. J. Mamula, S. Fatenejad, J. Craft, B cells process and present lupus autoantigens that initiate autoimmune T cell responses. *Journal of immunology* 152, 1453 (1994).
23. M. L. Albert, R. B. Darnell, Paraneoplastic neurological degenerations: keys to tumour immunity. *Nature reviews. Cancer* 4, 36 (2004).
24. C. Gaudin, F. Kremer, E. Angevin, V. Scott, F. Triebel, A hsp70-2 mutation recognized by CTL on a human renal cell carcinoma. *Journal of immunology* 162, 1730 (1999).
25. R. F. Wang, X. Wang, A. C. Atwood, S. L. Topalian, S. A. Rosenberg, Cloning genes encoding MHC class II-restricted antigens: mutated CDC27 as a tumor antigen. *Science* 284, 1351 (1999).
26. T. Wolfel, M. Hauer, J. Schneider, M. Serrano, C. Wolfel, E. Klehmann-Hieb, E. De Plaen, T. Hankeln, K. H. Meyer zum Buschenfelde, D. Beach, A p16INK4a-insensitive CDK4 mutant targeted by cytolytic T lymphocytes in a human melanoma. *Science* 269, 1281 (1995).
27. M. E. Engelhorn, J. A. Guevara-Patino, G. Noffz, A. T. Hooper, O. Lou, J. S. Gold, B. J.
Kappel, A. N. Houghton, Autoimmunity and tumor immunity induced by immune responses to mutations in self. *Nature medicine* 12, 198 (2006).
28. L. Casciola-Rosen, K. Nagaraju, P. Plotz, K. Wang, S. Levine, E. Gabrielson, A. Corse, A. Rosen, Enhanced autoantigen expression in regenerating muscle cells in idiopathic inflammatory myopathy. *The Journal of experimental medicine* 201, 591 (2005).
29. R. D. Schreiber, L. J. Old, M. J. Smyth, Cancer immunoediting: integrating immunity's roles in cancer suppression and promotion. *Science* 331, 1565 (2011).
30. S. Bernatsky, J. F. Boivin, L. Joseph, R. Rajan, A. Zoma, S. Manzi, E. Ginzler, M. Urowitz, D. Gladman, P. R. Fortin, M. Petri, S. Edworthy, S. Barr, C. Gordon, S. C. Bae, J. Sibley, D. Isenberg, A. Rahman, C. Aranow, M. A. Dooley, K. Steinsson, O. Nived, G. Sturfelt, G. Alarcon, J. L. Senecal, M. Zummer, J. Hanly, S. Ensworth, J. Pope, H. El-Gabalawy, T. McCarthy, Y. St Pierre, R. Ramsey-Goldman, A. Clarke, An international cohort study of cancer in systemic lupus erythematosus. *Arthritis and rheumatism* 52, 1481 (2005).
31. E. Tatsis, E. Reinhold-Keller, K. Steindorf, A. C. Feller, W. L. Gross, Wegener's granulomatosis associated with renal cell carcinoma. *Arthritis and rheumatism* 42, 751 (1999).
32. B. Vogelstein, N. Papadopoulos, V. E. Velculescu, S. Zhou, L. A. Diaz, K. W. Kinzler, Cancer Genome Landscapes. *Science* 339, 1546 (2013).
33. M. Burnet, Cancer—A Biological Approach. *BMJ* 1, 841 (1957).
34. F. M. Burnet, The concept of immunological surveillance. *Progress in experimental tumor research* 13, 1 (1970).
35. S. A. Quezada, K. S. Peggs, Exploiting CTLA-4, PD-1 and PD-L1 to reactivate the host immune response against cancer. *British journal of cancer* 108, 1560 (2013).
36. M. DuPage, C. Mazumdar, L. M. Schmidt, A. F. Cheung, T. Jacks, Expression of tumour-specific antigens underlies cancer immunoediting. *Nature* 482, 405 (2012).
37. H. Matsushita, M. D. Vesely, D. C. Koboldt, C. G. Rickert, R. Uppaluri, V. J. Magrini, C. D. Arthur, J. M. White, Y. S. Chen, L. K. Shea, J. Hundal, M. C. Wendl, R. Demeter, T. Wylie, J. P. Allison, M. J. Smyth, L. J. Old, E. R. Mardis, R. D. Schreiber, Cancer exome analysis reveals a T-cell-dependent mechanism of cancer immunoediting. *Nature* 482, 400 (2012).
38. Preliminary criteria for the classification of systemic sclerosis (scleroderma).
Subcommittee for scleroderma criteria of the American Rheumatism Association Diagnostic and Therapeutic Criteria Committee. *Arthritis and rheumatism* 23, 581 (1980).
39. P. J. Clements, P. A. Lachenbruch, J. R. Seibold, B. Zee, V. D. Steen, P. Brennan, A. J. Silman, N. Allegar, J. Varga, M. Massa, et al., Skin thickness score in systemic sclerosis: an assessment of interobserver variability in 3 independent studies. *The Journal of rheumatology* 20, 1892 (1993).
40. E. C. LeRoy, C. Black, R. Fleischmajer, S. Jablonska, T. Krieg, T. A. Medsger, Jr., N. Rowell, F. Wollheim, Scleroderma (systemic sclerosis): classification, subsets and pathogenesis. *The Journal of rheumatology* 15, 202 (1988).
41. J. Wu, H. Matthaei, A. Maitra, M. Dal Molin, L. D. Wood, J. R. Eshleman, M. Goggins, M. I. Canto, R. D. Schulick, B. H. Edil, C. L. Wolfgang, A. P. Klein, L. A. Diaz, P. J. Allen, C. M. Schmidt, K. W. Kinzler, N. Papadopoulos, R. H. Hruban, B. Vogelstein, Recurrent GNAS Mutations Define an Unexpected Pathway for Pancreatic Cyst Development. *Science Translational Medicine* 3, 92ra66 (2011).
42. D. S. Herman, G. K. Hovingh, O. Iartchouk, H. L. Rehm, R. Kucherlapati, J. G. Seidman, C. E. Seidman, Filter-based hybridization capture of subgenomes enables resequencing and copy-number detection. *Nat. Methods* 6, 507 (2009).
43. I. Kinde, J. Wu, N. Papadopoulos, K. W. Kinzler, B. Vogelstein, Detection and quantification of rare mutations with massively parallel sequencing. *Proceedings of the National Academy of Sciences of the United States of America* 108, 9530 (2011).
44. L. A. Casciola-Rosen, A. F. Pluta, P. H. Plotz, A. E. Cox, S. Morris, F. M. Wigley, M. Petri, A. C. Gelber, A. Rosen, The DNA mismatch repair enzyme PMS1 is a myositis-specific autoantigen. *Arthritis and rheumatism* 44, 389 (2001).

We claim:

1. A method, comprising:
    administering to a patient having an epithelial cancer a peptide comprising at least 8 and less than 50 contiguous amino acid residues of a human, autoimmune RPC1 antigen,
    wherein the peptide binds with high affinity to an HLA protein of the patient,
    wherein the peptide comprises a variant residue relative to the wild-type antigen,
    wherein the variant residue is E1072Q, K1365N, or I104T of RPC1, and
    wherein administering the peptide raises an immune response in the patient.

2. The method of claim 1, wherein prior to the step of administering the patient sample is tested to ascertain the patient's HLA type.

3. The method of claim 1, wherein a full-length version of the antigen is co-administered with the peptide.

4. The method of claim 1, wherein a full-length, wild-type version of the antigen is co-administered with the peptide.

5. The method of claim 1, wherein a full-length, mutant version of the antigen is co-administered with the peptide, wherein the antigen and the peptide comprise the variant residue.

6. The method of claim 1, wherein the epithelial cancer is breast cancer, lung cancer, ovarian cancer, or colorectal cancer.

7. The method of claim 1, wherein the peptide comprises at least 10 and less than 50 contiguous amino acid residues of the antigen.

8. The method of claim 1, wherein the peptide comprises at least 12 and less than 50 contiguous amino acid residues of the antigen.

9. The method of claim 1, wherein the peptide comprises at least 14 and less than 50 contiguous amino acid residues of the antigen.

10. A composition comprising a peptide comprising at least 8 and less than 50 contiguous amino acid residues of a human, autoimmune RPC1 antigen and an adjuvant,
    wherein the adjuvant is attached to the peptide,
    wherein the peptide binds with high affinity to a human HLA protein,
    wherein the peptide comprises a variant residue relative to the wild-type antigen,
    wherein the variant residue is E1072Q, K1365N, or I104T of RPC1, and
    wherein an immune response is raised in a patient when the composition is administered to the patient.

11. The composition of claim 10, wherein the peptide comprises at least 10 and less than 50 contiguous amino acid residues of the antigen.

12. The composition of claim 10, wherein the peptide comprises at least 12 and less than 50 contiguous amino acid residues of the antigen.

13. The composition of claim 10, wherein the peptide comprises at least 14 and less than 50 contiguous amino acid residues of the antigen.

14. The composition of claim 10, which is in admixture with a full-length version of the antigen.

15. The composition of claim 14, wherein the full-length version of the antigen is a wild-type antigen.

* * * * *